US008415343B2

(12) United States Patent
Glick et al.

(10) Patent No.: US 8,415,343 B2
(45) Date of Patent: *Apr. 9, 2013

(54) COMPOSITIONS AND METHODS FOR INHIBITING THE PROLIFERATION OF CELLS

(75) Inventors: Gary D. Glick, Ann Arbor, MI (US); Anthony W. Opipari, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1026 days.

This patent is subject to a terminal disclaimer.

(21) Appl. No.: 11/643,614

(22) Filed: Dec. 21, 2006

(65) Prior Publication Data
US 2007/0135418 A1  Jun. 14, 2007

Related U.S. Application Data

(60) Division of application No. 10/427,211, filed on May 1, 2003, now Pat. No. 7,572,788, which is a continuation-in-part of application No. 10/217,878, filed on Aug. 13, 2002, now abandoned, which is a continuation of application No. 09/767,283, filed on Jan. 22, 2001, now Pat. No. 7,220,739, which is a continuation of application No. 09/700,101, filed as application No. PCT/US00/11599 on Apr. 27, 2000, now Pat. No. 7,125, 866.

(60) Provisional application No. 60/131,761, filed on Apr. 30, 1999, provisional application No. 60/165,511, filed on Nov. 15, 1999, provisional application No. 60/191,855, filed on Mar. 24, 2000, provisional application No. 60/312,560, filed on Aug. 15, 2001, provisional application No. 60/313,689, filed on Aug. 20, 2001, provisional application No. 60/396,670, filed on Jul. 18, 2002.

(51) Int. Cl.
*A61K 31/55* (2006.01)
*A61K 31/59* (2006.01)
*A61K 31/05* (2006.01)

(52) U.S. Cl.
USPC .......................... 514/221; 514/167; 514/731

(58) Field of Classification Search .................. 514/167, 514/221, 731
See application file for complete search history.

(56) References Cited

U.S. PATENT DOCUMENTS

| | | |
|---|---|---|
| 3,261,828 A | 7/1966 | Uskokovic |
| 3,374,264 A | 3/1968 | Uskokovic |
| 3,384,635 A | 5/1968 | Calabateas |
| 3,415,814 A | 12/1968 | Calabateas |
| 3,847,905 A | 11/1974 | Bub |
| 4,076,823 A | 2/1978 | Wade |
| 4,088,756 A | 5/1978 | Voorhees |
| 4,108,852 A | 8/1978 | Bub |
| 4,110,337 A | 8/1978 | Szarvasi |
| 4,495,101 A | 1/1985 | Klaubert |
| 4,551,480 A | 11/1985 | Stiefel |
| 4,560,684 A | 12/1985 | Sugasawa |
| 4,623,646 A | 11/1986 | Casals-Stenzel |
| 4,751,223 A | 6/1988 | Glambowski |
| 4,820,834 A | 4/1989 | Evans |
| 4,894,366 A | 1/1990 | Okuhara |
| 4,898,861 A | 2/1990 | Morgan |
| 4,916,138 A | 4/1990 | Ueda |
| 4,929,611 A | 5/1990 | Okuhara |
| 4,946,778 A | 8/1990 | Ladner |
| 5,004,741 A | 4/1991 | Evans |
| 5,041,438 A | 8/1991 | Hsu |
| 5,141,930 A | 8/1992 | Nakao |
| 5,147,872 A | 9/1992 | Golwyn |
| 5,216,148 A | 6/1993 | Klaus |
| 5,288,514 A | 2/1994 | Ellman |
| 5,324,726 A | 6/1994 | Bock |
| 5,391,566 A | 2/1995 | Chakravarty |
| 5,444,092 A | 8/1995 | Collins |
| 5,521,170 A | 5/1996 | Setoi |
| 5,545,568 A | 8/1996 | Ellman |
| 5,559,230 A | 9/1996 | Ogawa |
| 5,591,227 A | 1/1997 | Dihn |
| 5,597,915 A | 1/1997 | Chambers |
| 5,599,352 A | 2/1997 | Dihn |
| 5,633,251 A | 5/1997 | Claremon |
| 5,697,967 A | 12/1997 | Dihn |

(Continued)

FOREIGN PATENT DOCUMENTS

| | | |
|---|---|---|
| CA | 2372150 | 11/2000 |
| CA | 2457405 | 2/2003 |

(Continued)

OTHER PUBLICATIONS

Covelli et al. (Immunopharmacology Immunotoxicology, 20(2), 199-209 (1998).*
Jones, The non-conalent interaction of pyrrolo[2, 1-c][benzodiazepines-5, 11-diones with DNA, Anti-Cancer Drug Design, 5:249-264 (1990).
Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.
Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.

(Continued)

*Primary Examiner* — Shirley V Gembeh
(74) *Attorney, Agent, or Firm* — Casimir Jones SC

(57) ABSTRACT

The present invention relates to chemical compounds, methods for their discovery, and their therapeutic use. In particular, the present invention provides benzodiazepine derivatives and methods of using benzodiazepine derivatives as therapeutic agents to treat a number of conditions associated with the faulty regulation of the processes of programmed cell death, autoimmunity, inflammation, and hyperproliferation, and the like.

9 Claims, 55 Drawing Sheets

U.S. PATENT DOCUMENTS

| | | | |
|---|---|---|---|
| 5,763,437 | A | 6/1998 | Sato |
| 5,776,946 | A | 7/1998 | McGeer |
| 5,861,380 | A | 1/1999 | Gyorkos |
| 5,962,337 | A | 10/1999 | Ohlmeyer |
| 6,004,942 | A | 12/1999 | Firestein |
| 6,074,859 | A | 6/2000 | Hirokawa |
| 6,080,588 | A | 6/2000 | Glick |
| 6,100,254 | A | 8/2000 | Budde |
| 6,277,844 | B1 | 8/2001 | Spector |
| 6,319,931 | B1 | 11/2001 | Kroemer |
| 6,506,744 | B1 | 1/2003 | Alig |
| 6,524,623 | B1 | 2/2003 | Hodosh |
| 6,524,832 | B1 | 2/2003 | Kufe |
| 2,457,405 | A1 | 3/2003 | Glick |
| 6,579,854 | B1 | 6/2003 | Mitchell |
| 6,605,593 | B1 | 8/2003 | Naicker |
| 6,613,739 | B1 | 9/2003 | Naicker |
| 6,767,533 | B1 | 7/2004 | Casellas |
| 6,824,561 | B2 | 11/2004 | Soykan |
| 6,916,813 | B2 | 7/2005 | Atwal |
| 7,125,866 | B1 | 10/2006 | Glick |
| 7,144,880 | B2 | 12/2006 | Glick |
| 7,150,433 | B2 | 12/2006 | Healy |
| 7,220,739 | B2 | 5/2007 | Glick |
| 7,250,410 | B2 | 7/2007 | Bourguignon |
| 7,276,348 | B2 | 10/2007 | Glick |
| 7,351,241 | B2 | 4/2008 | Bendett |
| 7,572,788 | B2 | 8/2009 | Glick |
| 7,638,624 | B2 | 12/2009 | Glick |
| 7,683,046 | B2 | 3/2010 | Glick |
| 7,851,465 | B2 | 12/2010 | Glick |
| 2002/0025946 | A1 | 2/2002 | Buchanan |
| 2002/0048566 | A1 | 4/2002 | El-Deiry |
| 2002/0128208 | A1 | 9/2002 | Snyder |
| 2003/0044776 | A1 | 3/2003 | Dykens |
| 2003/0119029 | A1 | 6/2003 | Glick |
| 2004/0009972 | A1 | 1/2004 | Ding |
| 2004/0087489 | A1 | 5/2004 | Ruiz |
| 2004/0157833 | A1 | 8/2004 | Harris |
| 2004/0176358 | A1 | 9/2004 | Glick |
| 2005/0113460 | A1 | 5/2005 | Glick |
| 2005/0261176 | A1 | 11/2005 | Glick |
| 2005/0272723 | A1 | 12/2005 | Glick |
| 2006/0025388 | A1 | 2/2006 | Glick |
| 2006/0052369 | A1 | 3/2006 | Glick |
| 2007/0135418 | A1 | 6/2007 | Glick |
| 2007/0299059 | A1 | 12/2007 | Glick |

FOREIGN PATENT DOCUMENTS

| | | |
|---|---|---|
| DE | 1810423 | 10/1969 |
| EP | 0227539 | 5/1990 |
| EP | 0 349 949 | 10/1990 |
| EP | 0 906 907 | 7/1999 |
| EP | 1143946 | 10/2001 |
| EP | 1423122 | 2/2003 |
| EP | 1398033 | 3/2004 |
| EP | 1622684 | 2/2006 |
| EP | 1742640 | 7/2006 |
| EP | 1778204 | 5/2007 |
| EP | 1786429 | 5/2007 |
| EP | 1845996 | 10/2007 |
| GB | 1363735 | 8/1974 |
| RU | 2096044 | 11/1997 |
| WO | 90/05305 | 5/1990 |
| WO | 90/13332 | 11/1990 |
| WO | 91/12779 | 9/1991 |
| WO | 92/01683 | 2/1992 |
| WO | 94/08234 | 4/1994 |
| WO | 97/01560 | 1/1997 |
| WO | 97/30992 | 8/1997 |
| WO | 98/14192 | 4/1998 |
| WO | 98/57161 | 12/1998 |
| WO | 99/19306 | 4/1999 |
| WO | 99/29347 | 6/1999 |
| WO | 99/58117 | 11/1999 |
| WO | 99/66958 | 12/1999 |
| WO | 00/19200 | 6/2000 |
| WO | 00/66106 | 11/2000 |
| WO | 01/51922 | 7/2001 |
| WO | 02/67988 | 9/2002 |
| WO | 02/098865 | 12/2002 |
| WO | 03/015703 | 2/2003 |
| WO | WO 03015703 A3 | 2/2003 |
| WO | 03/041658 | 5/2003 |
| WO | 03/045901 | 6/2003 |
| WO | 03 050261 | 6/2003 |
| WO | 03/106628 | 12/2003 |
| WO | 2005/004988 | 1/2005 |
| WO | 99/67220 | 7/2006 |
| WO | 2006/029245 | 8/2006 |
| WO | 2008/133635 | 11/2008 |
| WO | 2009/061916 | 5/2009 |

OTHER PUBLICATIONS

Bono et al., "Peripheral benzodiazepine receptor agonists exhibit potent antiapoptotic activities," Biochemical and Biophysical Research Communications, 1999, 265, pp. 457-461.

Bunin et al., "Synthesis and evaluation of 1,4-benzodiazepine libraries", Methods in Enzymology, 1996, 267, pp. 448-465.

Dichek, David A., et al., "Seeding of intravascular stents with genetically engineered endothelial cells," Laboratory Investigation, 80:5 pp. 1347-1353 (1989).

Gupta et al., "Psychitripic drugs in dermatology . . . " Database:EMbase (AN:86111413), Journal of the American Academy of Dermatology, 1986, vol. 14, No. 4, pp. 633-645.

Karle Jesper et al., "Diazepam protects against rat hippocampal neuronal cell death induced by antisense oligodeoxynucleotide to GABA-A receptor gamma-2 subunit" Brain Research, vol. 765, No. 1, 1997, pp. 21-29.

Lewis et al., "Editors' view: Cancer pharmacotherapy: 21st century 'magic bullets' and changing paradigms", British Journal of Clinical Pharmacology, 2006, 62:1,pp. 1-4.

Miernik et al., "The antimitotic activities of some benzodiazepines", Experientia, 1986, 42, pp. 956-958.

Koopman, W.J., et al., "The MRL-lpr/lpr Mouse. A Model for the Study of Rheumatoid Arthritis," Scan& J. Rheumatolo Suppl 75:284-o289 (1988).

Korsmeyer, S.J., "Bcl-2 Initiates a New Category of Oncogenes: Regulators of Cell Death," Blood 80(4):879-886 (1992).

Kozbor, et al.• "The production of monoclonal antibodies from human lymphocytes", Immunol. Today, 4:72 [1983].

Liu, J.R., et al., "Bclox•. is Expressed in Ovarian Carcinoma and Modulates Chemotherapy-induced Apoptosis," Gynecologic Oncology 70:398-403 (1998).

Los, M., et al., The Role of Caspases in Development, Immunity, and Apoptotic Signal Transduction: Immunity-10:629-639 (1999).

Lowman, et al., "Mutational analysis and protein engineering of receptor-binding determinants in human placental lactogen", J. Biol. Chem. 266:10982 [1991].

Luria,et al., "Tumor Viruses", General Viology 3rd edition,. 436-446 (1978)—Eds. John Wile & Sons, New York.

Malgrange, B., et al., "I•-Carbolines Induce Apoptotic Death of Cerebellar Granule Neurones in Cultures," NeuroReport 7(18):3041-3045 (1996).

Marino, M., et al., "Prevention of Systemic Lupus Erythematosus in MRL/lpr Mice by Administration of an Immunoglobulin . . . ," Nature Biotechnology—18:735-739 (2000).

McDonnell'—349:254-256T'J et al., Progression from Lymphoid Hyperplasia to High-Grade . . . Nature—349:254-256 (1991).

Miccoli, et al., "Potentiation of Lonidamine and Diazepam . . . ", Journal of the National Cancer Institute, vol. 90, No. 18, pp. 1400-1406, Sep. 1998.

Miller, K.A., et al., "Benzodiazepines Prevent Neuronal Death by Apoptosis & Necrosis . . . ,"Society for Neuroscience Abstracts—24(1-2):979 (1998).

Monks, A., et., Feasibility of High-Flux Anticancer Drug Screen Using a Diverse Panel of Cultured Human Tumor Cell Lines, Journal of the National Cancer Institute, 83:757-766 (1991).

Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).

Okuyama, H., et al., "Analysis of Defective Delayed-Type Hypersensitivity in Autoimmune Mice Bearing lpr Gene," Clln. Ex p. ImmunoL 63:87-94 1986.
Okuyama, H., et al., "Effect of Cyclophosphamide Pretreatment on Defective Delayed-Type Hypersensitivity . . . ," Int Arch. Allergy Appl. Immunol. 88:394-40.
Ozols, R.F., "Paclitaxel Plus Carboplatin in the Treatment of Ovarian Cancer," Seminars in Oncology 26(1) (Supp.2:84-89 (1999).
Paola Costantini et al., "Mitochondrion as Novel Target of Anticancer Chemotherapy", JNCI Journal of the National Cancer Institute 2000 92(13): 1042-1053; doi:10. 1093/jnci/92. 13. 1042.
Parks, Daniel J. "1,4-benzodiazepine-2,5-diones as small molecule antagonists of the HDM2-p53 interaction . . . " Bioorg Med Chem. Ltrs,. 15,(2005), 765-770.
Paull, K.D., et al., "Display and analysis of patterns of differential activity of drugs against human tumor . . . ", J. Natl. Cancer Inst., 81:1088-1092 [1989] (Abstract only).
Pestell, K.E., et al., "Charactehsation of the P53 Status, BCL-2 Expression and Radiation and Platinum Drug Sensitivity of . . . ," Int J. Cancer—77:913-918 (1998).
Raboisson, P. "Structure-based design, synthesis and biological evaluative of novel 1,4-diazepines as HDM2 antagonists," Bioorg Med Chem. Ltrs., 15,(2005), 1857-1861.
Ramdas et al., "Benzodiazepine compounds as inhibitors of the Src protein tyrosine kinase . . . " Archives of Biochemistry and Biophysics 368 (1999) 394-400.
Raynaud, F.I., et al., "Intracellular Metabolism of the Orally Active Platinum Drug JM216: Influence of Glutathione Levels," Br. J. Cancer 74(3) :380-?386 (1996).
Russell, J.H., et al., "Mature T Cells of Autoimmune lpr/lpr Mice have a Defect in Antigen-Stimulated Suicide," Proc. Nat. Acad. Sci. USA 90:4409-4413 (1993).
Sakata, K., et al., "Role of Fas/FasL Interaction in Physiology and Pathology: The Good and the Bad," Clinical Immunology and Immunopathology 87(1):1-7 (1998).
Sandstrom, P.A., et al., Autocrine Production of Extracellular Catalase Prevents Apoptosis.. Proc. Natl. Acad. Sci. USA—90:4708-4712 (1993).
Schlumpf, M., et al., "Delayed Developmental Immunotoxicity of Prenatal Benzodiazepines," Toxic. In Vitro13 8 (5):1061-1065(1994).
Schoemaker, H., et al., "Specific High-?Affinity Binding Sites for [3H]Ro5—4864 in Rat Brain and Kidney," The J. of Pharm and Experimental Therapeutics—225(1)61-69.
Schwab, M., et al., "Amplified DNA with Limited Homology to myc Cellular Oncogene is Shared by Human Neuroblastoma Cell Lines and . . . ," Nature—305:245-248 (1983).
Scott, C.F., et al., "Comparison of Antigen-Specific T Cell Responses in Autoimmune MRL/mp-lpr/lpr and MRUMp-++ Mice," The Journal of Immunology—1322:633-639 (1.
Sentman, C.L., et al., "bcl-2 Inhibits Multiple Forms of Apoptosis but not Negative Selection in Thymocytes," Cell 67:879-886 (1991).
Sheppard, R.C., et al., "Acid-Labile Resin Linkage Agents for Use in Solid Phase Peptide Synthesis;" Int J. Peptide Protein Res. 20:451-454 (1982).
Snyder, Jane R., et al, "Dissection of melanogenesis with small molecules identifies prohibition as a regulator", Chemistry & Biol. 12:477-484, 4(2005).
Stevens, S.Y., et al., "Non Nucleic Acid Inhibitors of Protein-DNA Interactions Identified Through Combinatorial Chemistry," J. Am. Chem.Soc.—118:10650-10651 (1996).
Sugimoto, T., et al., Determination of Cell Surface Membrane Antigens . . . JNCI—73: (1):51-57 (1984).
Swanson et al, "Ligand recognition by anti-DNA Autoantibodies," Biochemistry, 35:1624-1633 [1996] (Abstract only).
Swanson, P.C., et al., "Ligand Recognition by Murine Anti-DNA Autoantibodies," J. Clin. Invest 97(7):1748-1760 (1996).
Swanson, P.C.,et al., "High Resolution Ephope Mapping of an Anti-DNA Autoantibody Using Model DNA Ligands," J. Immunology 71 152(5):2601-2612 (1994).
Takahashi, T., et al., "Generalized Lymphoproliferative Disease in Mice, Caused by a Point Mutation in the Fas Ligand;" Cell 76:969-976 (1994).

Tanimoto, Y., et al., Benzodiazepine Receptor Agonists Modulate Thymocyte Apoptosis Through Reduction of the Mitochondrial . . . Jpn. J. Pharmacol. 79:177-183 (1999).
Taupin, V., et al., Endogenous Anxiogenic peptide, ODN-Diazepam-Binding Inhibitor, and Benzodiazepines.. Lymphokine and Cytoklne Research 10(1):7-13 (1991).
Theoffopoulous, AN, et al., "Murine Models of Systemic Lupus Erythematosus," Advances in Immunology 37:269-390 (1985).
Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.
Walser, et al., "Quinazolines and 1,4-benzodiazepines. LILX. Preparation of Pyrrolo[2,1-c]-1,4-benzodiazepin-2-ones", J. Org. Chem. 38:3502-3507 (1973).
Watanabe-Fukunaga, R., et al., "Lymphoproliferation Disorder in Mice Explained by Defects in Fas Antigen that Mediates Apoptosia,"Nature 356:314-317 (199.
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G. Y., et al., "Receptor-Mediated in Vitro Gene Transformation by a Soluble DNA Carrier System," The Journal of Biological Chemistry 262(10):4429-4432 (1987).
Wyllie, A.H., "The Genetic Regulation of Apoptosis," Current Opinion in Genetics & Development 5:97-104 (1995).
Zamzami, N., et al., "Mitochondrial Control of Nuclear Apoptosis," J. Exp. Med. 183:1533-1544 1996.
Zoratti, M., et al., "The Mitochondrial Permeability Transition," Biochimica et Biophysica Acta 1241:139-176 (1995).
EP Search, EP Patent Application No. 05856659.7 mailed Dec. 9, 2008.
EP Search, EP Patent Application No. 04 775 923.8, dated Dec. 15, 2008.
Appleby, et al., "Murine chronic graft-versus-host disease as a model of osystemic lupus erythematosus: effect of immunosuppressive drugs on disease development," Clin. Exp. Immunol. (1989) 78, 449-453.
Bastian, et al., "Casein Interference in Bovine Plasmin Assays Using a Synthetic Substrate," (1991) J Dairy Sci 74:4119-4124.
Johnson, et al., "Mechanistic Basis for Therapeutic Targeting of the Mitochondrial FF-ATPase", downloaded from http://pubs.acs.org on Dec. 5, 2008, ASC Chem. Biol. 1 (5), 304-308, Publication Date (WEB): Jun. 9, 2006.
Piedimonte, et al., "Association of Tyrosine Protein Kinase Activity With Mitochondria in Human Fibroblasts," Journal of Cellular Biochemistry 32:113-123 (1986).
Iiangumaran, et al., "CD44 Selectively Associates with Active Src Family Protein Tyrosine Kinases Lck and Lyn in Glycosphingolipid-Rich . . . ", Blood, vol. 91, No. 10 (May 15, 1998), pp. 3901-3908.
Sato, et al., "CD22 negatively and positively regulates signal transduction through the B lymphocyte antigen receptor," seminars in Immunology, vol. 10, 1998, pp. 287-297.
Joshi, et al., "Oligomycin Sensitivety-conferring Protein (OSCP) of Mitochodrial ATP Synthase," The Journal of Biological Chemistry, vol. 267, No. 18,m Issue of Jun. 25, pp, 12860-12867, 1992.
Otto, Michael W., Ph.D., et al., "Benzodiazepine Use, Cognitive Impairment, and Cognitive-Behavioral Therapy for Anxiety Disorders: Issues in the Treatment of a Patient in Need," J. Clin. Psychiatry, 2005, 66 (supp 2).
Yoshi, M., et al., (2005) Nippon Yakurigaku Zasshi 125(1):33-36 (English Abstract attached).
Yasuda, K., (2004) Nippon Rinsho. 62 Suppl. 12:360-363. Abstract not available.
Decaudin, Didier, "Peripheral benzodiazepine receptor and its clinical targeting," Anti-Cancer Drugs, 2004, vol. 15, No. 8.
Bonnot, O., et al., "Exposition in utero au lorazepam et atresie anale: signal epidemiologique," (2003) Encephale. 29 (6):553-559.

Lacapere, Jean-Jacques, Vassilios Papadopoulos, "Peripheral-type benzodiazepine receptor: structure and function of a cholesterol-binding protein in steroid and bile acid biosynthesis," Steroids, 68 (2003) 569-585.

Galiegue, S., et al., "The Peripheral Benzodiazepine Receptor: A Promising Therapeutic Drug Target," (2003) Curr. Med. Chem (10(16):1563-1572.

Papadopoulo, V. (2003), Lecture: Peripheral benzodiazepine receptor: structure and function in health and disease, Ann. Pharm. Fr. 61(1):30-50.

Goethals, Ingeborg, et al., "Is central benzodiazepine receptor imaging useful for the identification of epileptogenic foci in localization-related epilepsies?" European Journal of Nuclear Medicine and Molecular Imaging vol. 30, No. 2, Feb. 2003.

Castedo, Marian, et al., "Mitochondrial Apoptosis and the Peripheral Benzodiazepine Receptor: a Novel Target for Viral and Pharmacological Manipulation," The Journal of Experimental Medicine, vol. 196, No. 9, Nov. 4, 2002.

Buffett-Jerrott S.E. et al., "Cognitive and Sedative Effects of Benzodiazepine Use," Current Pharmaceutical Design, 2002, 8, 45-48.

Smyth, W.F., et al. (1998), "A critical evaluation of the application of capillary electrophoresis to the detection and determination of 1,4-benzodiazepine tranquilizers in formulations and body materials," Electrophoresis 19 (16-17):2870-2882.

Yoshii, M., et al. (1998) Nihon Shinkeo Seishin Yakurigaku Zasshi, 18(2):49-54.

Varani, et al., (1994), "All-trans Retinoic Acid (RA) Stimulates Events in Organ-cultured Human Skin that Underlie Repair," J. Clin. Invest., 94:1747-1753.

Griffith, C.E., "Editorial Comment: Ascomycin: an advance in the management of atopic dermatitis," Br. J. Dermatol., Apr. 2001, 144(4):679-81.

Stern, R.S. (1995), "Epidemiology of Psoriasis," Dermatologic Clinics, 13:717-722.

Fry, L (1988), "Psoriasis," Brit. J. Dermatol., 119:445-461.

Krueger GC, et al., (1984), "Psoriasis," J. Am. Acad. Dermatol., 11:937-947.

Varani, J., et al. (2001), "Heparin-Binding Epidermal-Growth-Factor-Like Growth Factor Activation of Keratinocyte ErbB . . . ", J. Invest. Dermatol., 117:1335-1341.

Varani, J., et al., "A Novel Benzodiazepine Selectively Inhibits Keratinocyte Proliferation . . . ", The Journal of Pharmacology and Experimental Therapeutics, 2005, vol. 313, No. 1, pp. 56-63.

International Search Report and Written Opinion, PCT/US2008/082629, mailed Jun. 1, 2009.

Laupacis, et al., "Cyclosporin A: a powerful immunosuppressant", CMA Journal, May 1, 1982, vol. 126, pp. 1041-1046.

Lowe, "Systemic treatment of severe psoriasis," The New England Journal of Medicine, 324 (5), Feb. 7, 1991, pp. 333-334.

EP Supplementary Search Report, EP Application No. 02794914.8 dated Nov. 6, 2008.

EP Patent Application No. 05 80 4417 Supplementary European Search Report dated Mar. 26, 2009.

Chinese Office Action, CN Patent Application No. 200580029827.4, dated Apr. 17, 2009.

Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).

EP Supplementary Search Report mailed Nov. 6, 2008, EP Patent Application No. 02794914.8.

Lee, Sunwoo, et al., "Improved Catalysts for the Palladium-Catalyzed Synthesis of Oxindoles by . . . ", J. Org. Chem. 2001, 66, pp. 3402-3415.

Shaughnessy, Kevin, H., et al., "Palladium-Catalyzed Inter- and Intramolecular . . . " J. Org. Chem. 1998, 63, pp. 6546-6553.

Puodziunaite, B., et al., "Bromination of Aromatic Ring of Tetrahydro-1,5-Benzodiazepin-2-Ones", Chemistry of Heterocyclic Compounds, vol. 36, No. 6, 2000.

Wolvetang, et al., FEBS Letters (1994), 339, 40-44.

Nawrocka, et al., Arch. Pharm. (Weinheim) Jan. 2001, 334(1), 3-10.

International Search Report and Written Opinion of PCT/US2008/057827 dated Oct. 6, 2008.

International Search Report, PCT/US2006/042753, dated May 6, 2008.

Written Opinion of the International Searching Authority, PCT/US06/21561, dated Aug. 17, 2007.

International Preliminary Report on Patentability, PCT/US2006/041446, mailed May 8, 2008.

International Search Report and Written Opinion, PCT/US2006/00442, mailed May 12, 2006.

International Report on Patentability, PCT/US2006/000442 mailed Jul. 12, 2007.

AU Examiner's Report, AU Patent App. No. 2005323519 dated Nov. 27, 2007.

International Search Report and Written Opinion, PCT/US08/56231, mailed Jun. 24, 2008.

International Search Report and Written Opinion, PCT/US05/14463, mailed Dec. 4, 2006.

International Search Report and Written Opinion, PCT/US07/11422, mailed Nov. 15, 2007.

International Search Report and Written Opinion, PCT/US07/13576, mailed Nov. 23, 2007.

Godic, "New approaches to psoriasis treatment. A review." 2004, Acta Dermatoven APA, vol. 13, No. 2, pp. 50-57.

International Search Report, PCT/US06/042753, mailed Apr. 19, 2007.

Desjardins, P and Stephanie Ledoux, "The Role of Apoptosis in Neurodegenerative Disease," Metabolic Brian Disease, vol. 13, No. 2, pp. 79-96 (1998).

International Search Report, PCT/US06/41446, mailed Aug. 1, 2007.

AU Patent Application No. 2006203946 Examiner's Report dated Sep. 10, 2008.

Bhagavathula, Narasimharao, et al., "7-Chloro-t-(4-hydroxyphenyl_-1-methyl-3-(naphthalen-2-ylmethyl) . . . ", J Pharmacol & Exp Ther 324: 938-947 (2008).

Borea, "Stereochemical Features Controlling Binding and Intrinsic Activity Properties of Benzodiazepine Receptor Ligands", Molecular Pharmacology, Apr. 1987, 31 (4), pp. 334-344, p. 344, Abstract.

EP Search Report dated Aug. 10, 2010, EP Patent Application No. 08731682.4.

EP Search Report dated Jun. 23, 2010, EP Patent Application No. 10 003 823.1.

EP Search Report dated Nov. 26, 2009, EP Patent Application No. 09003224.4.

Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68, pp. 2844-2852.

Reddy, Pavan, et al., "Interleukin-18 Regulates Acute Graft-Versus-Host Disease by Enhancing Fas-mediated Donor T Cell Apoptosis," J. Exp. Med., 2001, 194: 1433-1440.

Bossu, et al., "IL-18 cDNA vaccination protects mice from spontaneous lupus-like autoimmune disease," PNAS 2003, 100: 14181-14186.

De Bandt, et al., "Systemic lupus erythematosus induced by anti-tumour necrosis factor alpha therapy: a French national survey," Arthritis Res. & Ther., 2005, 7: R545-R551.

Abunasser, et al., "Etanercept-Induced Lupus Erythematosus Presenting as a Unilateral Pleural Effusion," Chest 2008, 134: 850-853.

Busca, et al., "Recombinant human soluble tumor necrosis factor receptor fusion protein as treatment for steroid refractory graft-versus-host disease following allogeneic hematopoietic stem cell transplatation," Am. J. Hematol., 2007, 82: 45-52.

Kyungjin, Kim, Steven K. Volkkan, and Jonathan A. Ellman, Synthesis of 3-Substituted 1,4-Benzodiazepin-2-ones, J. Braz. Chem. Soc. vol. 9(4), 375-379 (1998).

Tarpley, et al., J. Chroni Diseases (1965), 18 (abstract only).

Dourlat, et al., "Novel 1,4-benzodiazepine derivaties with antiproliferative properties on tumor cell lines," Bioorganic & Medicinal Chemistry Letters, 2007, vol. 17, Issue 9, pp. 2527-2530.

Elz et al., 1989 Eur. J. Med Chem. 259-262.

Atwal et al., Tet Lett. 30, 1989, 7313.

Johnson, K.M., et al., Chemistry & Biology, 2005, 12:486-496.
Francis, T.M., et al., "Identification of cytotoxic, T-cell-selective 1,4-benzodiazepine-2,5-diones," Bioorganic & Medicinal Chemistry Letters, Pergamon, Elsevier Science, GB, vol. 16, No. 9, May 1, 2006, pp. 2423-2427.
Akssira, M., et al., "New Routes to 1,4-benzodiazepin-2,5-diones," Tetrahedron (1994), vol. 50, No. 30, pp. 9051-9060.
Mohiuddin, G., et al., "A Versatile Synthesis of 3H-1(H), 4(H)-Benzodiazepin-2,5-diones," Indian Journal of Chenmistry, 1985, vol. 24B, pp. 905-907.
Boojamra, Constantine G., et al., "An Expedient and High-Yielding Method for the Solid-Phase Synthesis of Diverse 1,4-Benzodiazepine-2, 5-diones," Journal of Organic Chemistry, 1995, vol. 60, No. 18, pp. 5742-5743.
Keating, Thomas A., et al., "A Remarkable Two-Step Synthesis of Diverse 1, 4-Benzodiazepine-2, 5-diones Using the Ugi Four-Component Condensation," Journal of Organic Chemistry, 1996, vol. 61, No. 25, pp. 8935-8939.
Juaristi, Eusebio, et al., "Enantioselective Synthesis of α-Amino Acides from Chiral 1, 4-enzodiazepine-2, 5-diones Contianing the α-Phenethyl Group," Journal of Organic Chemistry, Mar. 26, 1999, vol. 64, No. 8, pp. 2914-2918.
Marc, Gasper, et al., "High Yield Phase Transfer N-Alkylation of Some Benzodiazepinese by Esters of ω-Halo Acids," Synthetic Communications, 1998, vol. 28, No. 7, pp. 1143-1157.
Bolli, M.H., et al., "Novel Benzo[1,4]diazepin-2-one-Derivatives as Endothelin Receptor Antagonists", Journal of Medicinal Chemistry, vol. 47, No. 11, Apr. 23, 2004, pp. 2776-2795.
International Search Report, International Patent Application No. PCT/US05/24060, dated Dec. 13, 2006.
International Search Report, International Patent Application No. PCT/US02/26171 dated Aug. 8, 2003.
International Search Report, International Patent Application No. PCT/US01/11599 dated May 2, 2002.
International Search Report, International Patent Application No. PCT/US05/31942 dated Sep. 21, 2006.
International Search Report, International Patent Application No. PCT/US04/013455 dated Jan. 6, 2006.
European Search Report, EP Patent Application No. 03 027 484.9-2117 dated May 3, 2004.
European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
Adachi, M., et al., "Aberrant Transcription Caused by the Insertion an Early Transposable Element . . . ," PNAS. USA-90:1756-1760 (1993).
Adelman, N.E., et al., Treatment of (NZB × NZW)F1 Disease with Anti-I-A Monoclonal Antibodies; J. Exp. Med.—158:1350.1355 (1983).
Atwal, K.S., et al., "Small Molecule Mitochondrial F1F0 ATPase Huydrolase Inhibitors as Cardioprotective Agents" J. Med. Chem. 47, pp. 1081-1084 (2004).
Baader, S.L., et al., Uptake and Cytotoxicity of Ascorbic Acid and Dehydroascorbic Acid . . . Anticancer Research—14:221-228 (1994).
Beale, P.J., et al., "BCL-2 Family Protein Expression and Platinum Drug Resistance in Ovarian Carcinoma," British Journal of Cancer—82 (2) :436-440 (2000).
Beurdeley-Thomas, et al., "The peripheral benzodiazepine receptors: a review," Journal of Neuro-Oncology 46 (2000) 45-56.
Blum, P., et al., "Stiff-Person Syndrome: An Autoimmune Disease," Movement Disorders 6(1):12-20 (1991).
Boojamra, C.G., et al., "Solid-Phase Synthesis of 1,4. Benzodiazepine-2,5-Diones. Library Prep. and Demonstration of Synthesis Generality," J. Org. Chem.—62:1240-1256 (1997).
Bunin, B.A., et al., "The Combinatorial Synthesis and Chemical and Biological Evaluation of a 1,4-Benzodiazepine Libra ," PNAS USA—91:4708-4712 (1994).

Bunin, BA., et al., "A General and Expedient Method for the Solid-Phase Synthesis of 1,4-Benzodlazepine Derivatives," J. Am. Chem. Soc.—114:10997-10998 (1992).
Chumakov,A.M., et al., "Analysis of p53 Transactivation Through High-Affinity Sites," Oncogene—8:3005o3011 (1993).
Churcher et al., "A new series of potent benzodiazepine γ-Secretase inhibitors," Bioorganic & Medicinal Chemistry Letters 13 (2003) 179-183.
Cohen, P.L., et al., "Lpr and gld: Single Gen• Models of Systemic Autoimmunity and Lymphoproliferative Disease," Annu. Rev. Immunol. 9:243-269 (1991).
Cole et al., "The EBV-Hybridoma Technique and its Application to Human Lung Cancer", Monoclonal Antibodies and Cancer Therapy, Alan R. Liss, Inc., pp. 77-96 [1985].
Colosi, et al,"Mutational analysis of the intracellular domain of the human growth hormone recetor", J. Biol. Chem., 268:12617 [1993].
Crabtree, R.H., "A New Type of Hydrogen Bond," Science 282:2000-2001 1998.
Darrow et al., "Structurally similar small molecule photoaffinity CCK-A Agonists and Antagonists as Novel Tools . . . ", Bioorganic & Medicinal Chemistry Letters 8 (1998) 3127-3132.
Desoize, B., "Anticancer Drug Resistance and Inhibition of Apoptosis," Anicancer Research—14:2291-2294 1994.
Doble, A., et al., "Labelling of Peripheral-Type Benzodiazepine B Human Brain with [aH]l 1195: Anatomical and Subcellular Distribution," Brain Research Bulletin,18:49-61 1987.
Don,A. et al., Cancer Cell, vol. 3, May 2003 497-509.
Donadio, J.V., et al., Immunosuppressive Drug Therapy in Lupus Nephritis, American Journal of Kidney Diseases 21 (3):239-250 1993.
Ermak, T.H., et al., "Treatment of Murine Lupus with Monoclonal Antibody to L3T4," Laboratory Investigation 61(4):447-456 1989.
Fuh et al, "Rational design of potent antagonists to the human growth hormone receptor", Science, 256:1677 [1992].
Garcia-Calvo, M., et al. "Inhibition of Human Caspases by Peptide-Based and Macromolecular Inhibitors," The Journal of Biological Chemistry 273(49):32608-32613 1998.
Gorczyca, W., et al., "Induction of DNA Slrand Breaks Associated with Apoptosis During Treatment of Leukemias," Leukemia 7(5):659-670 1993.
Gordon, E.M., et al., Applications of Combinatorial Technologies to Drug Discovery. 2. Combinatorial Organic 52 Synthesis, Library Screening . . . Journal of Med. Chem. 37(10): (1989).
Grasberger, Bruce L., "Discovery and cocrystal structure of benzodiazepinedione HDM2 antagonists that activate p53 in cells", J. Med. Chem., 48, (2005), 909-912.
Hahn, B.H., et al.; "Influence of Cyclophosphamide and Other Immunosuppressive Drugs on Immune Disorders . . . ," Arthritis and Rheumatism—18(2):145-152 (1975).
Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).
Hang, L., et al., "A Spontaneous Rheumatoid Arthritis-Like Disease in MR/1 Mice," J. Exp. Mod.—155:1690-1701 1982.
Herranz, R., "Cholesystokinin Antagonists: Pharmacological and Therapeutic Potential", Medicinal Research Reviews 23 (2003) 559-603.
Horowitz, R.E., et al., "Cyclophosphamide Treatment of Mouse Systemic Lupus Erythematosus," Laboratory Investigation 21 (3): 199-206 1969.
Hulme, C. J. "Improved procedure for the solution phase preparation of 1,4-benzodiazepine-2,5-dione libraries . . . ", Org. Chem., 63,(1998), 8021-8023.
Huse et al., "Generation of a Large Combinatorial Library of the Immunoglobulin Repertoire in Phage Lambda", Science, 246:1275-1281 [1989].
Itoh, N., et al., "The Polypeptide Encoded by the cDNA for Human Cell Surface Antigen Fas Can Mediate Apoptosis," Cell 66:233-243 (1991).
Kamal, A., "Synthesis of DNA-interactive Pyrrolo[2,1-c][1,4] benzodiazepines by employing polymer-supported reagents . . . ," Synlett, 14,(2004), 2533-35.

Kerver et al, "In situ detection of spontaneous superoxide anion and singlet oxygen production by mitochondria in . . . ", Histochem. J., 29:229-237 [1997] (Abstract only).

Kim et al., "Synthesis of 3-substituted 1,4-benzodiazepin-2-ones," J. Braz. Chem. Soc. 9:375-379 (1998).

Kohler and Milstein, "Continuous cultures of fused cells . . . ", Nature, 256:495-497 [1975].

Brittain, H.G., Polymorphism in Pharmaceutical Solids (1999), published by Marcel Dekker, Inc. (New York, USA), Chapter 5, pp. 205-208.

Byrn, S.R., et al. Solid-State Chemistry of drugs. 2nd ed. (1999), published by SSCI, Inc. (Indiana, USA).

Gallant, J.E., et al.,"Incidence and Natural History of Cytomegalovirus Disease in Patients with Advanced Human . . . " The Journal of Infect. Disease, 166: 1223-1227 (1992).

Gordon, C., et al.. "Chronic Therapy with Recombinant Tumor Necrosis Factor-α in Autoimmune NZB/NZW Fi Mice," Clinical Immunology and Immunopatholoy, 52:421-434 (1989).

Okuyama, H., et al., "Effect of Cyclophosphamide Pretreatment on Defective Delayed-Type Hypersensitivity . . . ," Int Arch. Allergy Appl. Immunol. 88:394-401 (1989).

Shoemaker, Hans, et al., "Specific High-Affinity Binding Sites for [3H]Ro 5-4864 in Rat Brain and Kidney," The Journal of Pharmacology and Experimental Therapeutics, vol. 225, No. 1 (1983).

Scott, C.F., et al., "Comparison of Antigen-Specific T Cell Responses in Autoimmune MRL/Mp-lpr/lpr and MRL/Mp-+/+ Mice," The Journal of Immunology, vol. 132, No. 2, pp. 633-639 (1984).

Watanabe-Fukunaga, R., et al., "Lymphoproliferation Disorder in Mice Explained by Defects in Fas Antigen that Mediates Apoptosis," Nature 356:314-317 (1992).

Cunha, 2006, "The first bismuth(III)-catalyzed guanylation of thioureas", Tetrahedron Letters 47:6955-56.

Cunha, 2002, "Bismuth nitrate pentahydrate: a new and environmentally benign reagent for guanidylation of N-benzoylthioureas", Tetrahedron Letters 43: 49-52.

Kluge, et al., "Kinetics of Inactivation of the F1F0 ATPase of Propionigenium modestum by Dicyclohexylcarbodiimide in Relationship to H+ and Na+ Concentration: Probing the Binding Site for the Coupling Ions," Biochemistry 1993, 32, 10378-10386.

Covelli, Vito, "Stress, Neuropsychiatric Disorders and Immunological Effects Exerted by Benzodiazepines," Immunopharmacology and Immunotoxicology, 20(2), 199-209 (1998).

Office Action Mailed May 24, 2010, U.S. Appl. No. 11/176,719, filed Jul. 6, 2005.

Office Action Mailed Aug. 19, 2009, U.S. Appl. No. 11/176,719, filed Jul. 6, 2005.

Office Action Mailed Apr. 3, 2009, U.S. Appl. No. 11/176,719, filed Jul. 6, 2005.

* cited by examiner

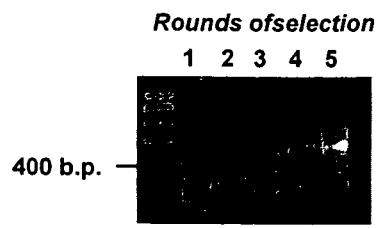
Figure 1. Phage-display selects out the OSCP. Semiquantitative PCR using primers specific for the OSCP sequence reveals enrichment of clones encoding the OSCP with each round of selection using immobilized Bz-423.

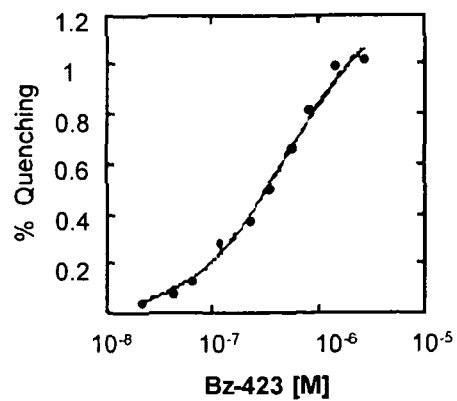
Figure 2. Binding isotherm of Bz-423 and purified human OSCP.

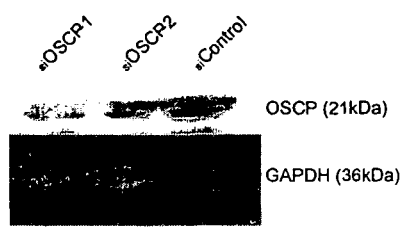
Figure 3. siRNA reduces the OSCP. $10^6$ HEK 293 cells transfected with 0.84 μg of siRNA duplexes specific for OSCP or scrambled control. After 72 h, protein expression determined by immunoblotting whole cell extracts. OSCP is reduced and GAPDH increased as glycolytic response.

FIG. 4A-1

| Gene | NCBI Accession Number | FOLD INCREASE |
|---|---|---|
| glyceraldehyde-3-phosphate dehydrogenase | M33197 | 23.02 |
| ribosomal protein L29 | NM_000992 | 21.62 |
| heat shock 90kD protein 1, beta | AI218219 | 21.27 |
| Lysosomal-associated multispanning membrane protein-5 | NM_006762 | 20.19 |
| ferritin, light polypeptide | BG538564 | 19.50 |
| Consensus includes gb:AJ249377.1 /DEF=Homo sapiens partial mRNA for human Ig lambda light chain variable region, clone MB91 (331 bp). /FEA=mRNA /GEN=IGLV /PROD=immunoglobulin lambda variable region /DB_XREF=gi:5911837 /UG=Hs.247898 Human anti-streptococ | AJ249377 | 18.95 |
| Consensus includes gb:D84143.1 /DEF=Human immunoglobulin (mAb59) light chain V region mRNA, partial sequence. /FEA=mRNA /PROD=immunoglobulin light chain V-J region /DB_XREF=gi:1255613 /UG=Hs.121508 Human immunoglobulin (mAb59) light chain V region mRNA, | D84143 | 18.76 |
| gb:AJ225092.1 /DEF=Homo sapiens mRNA for single-chain antibody, complete cds. /FEA=CDS /PROD=immunoglobulin /DB_XREF=gi:3090425 /UG=Hs.249245 Homo sapiens mRNA for single-chain antibody, complete cds /FL=gb:AJ225092.1 | AJ225092 | 18.62 |
| ribosomal protein L29 | BF683426 | 18.53 |
| Consensus includes gb:L48784 /DEF=050 Homo sapiens cDNA /FEA=mRNA /DB_XREF=gi:1066715 /UG=Hs.182426 ribosomal protein S2 | L48784 | 17.74 |
| profilin 1 | NM_005022 | 17.74 |
| ornithine decarboxylase antizyme 1 | AF090094 | 16.18 |
| serine hydroxymethyltransferase 2 (mitochondrial) | NM_005412 | 15.75 |
| chaperonin containing TCP1, subunit 7 (eta) | NM_006429 | 15.12 |
| ribosomal protein L8 | NM_000973 | 14.94 |
| macrophage migration inhibitory factor (glycosylation-inhibiting factor) | NM_002415 | 14.75 |
| Consensus includes gb:D84140.1 /DEF=Human immunoglobulin (mAb56) light chain V region mRNA, partial sequence. /FEA=mRNA /PROD=immunoglobulin light chain V-J region /DB_XREF=gi:1255610 /UG=Hs.248043 Human immunoglobulin (mAb56) light chain V region mRNA, | D84140 | 14.48 |
| transketolase (Wernicke-Korsakoff syndrome) | BF696840 | 14.41 |
| ribosomal protein L18 | NM_000979 | 14.38 |
| transketolase (Wernicke-Korsakoff syndrome) | L12711 | 13.75 |
| ubiquitin-conjugating enzyme E2I (UBC9 homolog, yeast) | AA910614 | 12.75 |
| glyceraldehyde-3-phosphate dehydrogenase | M33197 | 12.69 |
| glyceraldehyde-3-phosphate dehydrogenase | BF689355 | 12.67 |
| nuclease sensitive element binding protein 1 | BE966374 | 12.57 |

FIG. 4A-2

| | | |
|---|---|---|
| neutrophil cytosolic factor 4 (40kD) | NM_013416 | 12.52 |
| T-cell leukemia/lymphoma 1A | X82240 | 12.46 |
| ribosomal protein L18a | NM_000980 | 12.33 |
| glyceraldehyde-3-phosphate dehydrogenase | BE561479 | 12.29 |
| gb:L07950.1 /DEF=Homo sapiens MHC class I HLA B71 mRNA, complete cds. /FEA=CDS /GEN=HLA-B /PROD=MHC HLA B71 /DB_XREF=gi:307236 /FL=gb:L07950.1 | L07950 | 12.26 |
| ubiquitin carrier protein | NM_014501 | 12.12 |
| actin, beta | X00351 | 11.85 |
| enolase 1, (alpha) | U88968 | 11.53 |
| replication factor C (activator 1) 2 (40kD) | M87338 | 11.48 |
| phosphoserine aminotransferase | NM_021154 | 10.95 |
| MCM7 minichromosome maintenance deficient 7 (S. cerevisiae) | AF279900 | 10.74 |
| ribosomal protein S5 | NM_001009 | 10.69 |
| RNA polymerase II transcriptional regulation mediator (Med6, S. cerevisiae, homolog of) | NM_005466 | 10.68 |
| eukaryotic translation initiation factor 3, subunit 8 (110kD) | BC000533 | 10.65 |
| chaperonin containing TCP1, subunit 2 (beta) | AL545982 | 10.52 |
| CGI-135 protein | NM_016068 | 10.35 |
| polymerase (DNA directed), delta 2, regulatory subunit (50kD) | NM_006230 | 10.25 |
| ribosomal protein L13 | AW574664 | 9.93 |
| procollagen-proline, 2-oxoglutarate 4-dioxygenase (proline 4-hydroxylase), beta polypeptide (protein disulfide isomerase; thyroid hormone binding protein p55) | J02783 | 9.85 |
| HMT1 hnRNP methyltransferase-like 2 (S. cerevisiae) | NM_001536 | 9.83 |
| cold inducible RNA binding protein | NM_001280 | 9.66 |
| ATP synthase, H+ transporting, mitochondrial F1 complex, delta subunit | BE798517 | 9.57 |
| pinin, desmosome associated protein | AF112222 | 9.50 |
| pyruvate kinase, muscle | NM_002654 | 9.43 |
| gb:L23516.1 /DEF=Human Ig rearranged gamma-chain, V-DXP4-JH6c, complete cds. /FEA=mRNA /DB_XREF=gi:385218 /FL=gb:L23516.1 | L23516 | 9.42 |
| fusion, derived from t(12;16) malignant liposarcoma | NM_004960 | 9.37 |
| immunoglobulin heavy constant mu | U80139 | 9.32 |
| maternal G10 transcript | NM_003910 | 9.30 |
| major histocompatibility complex, class I, B | D83043 | 9.29 |
| small EDRK-rich factor 2 | NM_005770 | 9.29 |
| heat shock 90kD protein 1, beta | AF275719 | 9.05 |
| Consensus includes gb:AF254822 /DEF=Homo sapiens SMARCA4 isoform (SMARCA4) gene, complete cds, alternatively spliced /FEA=CDS_2 /DB_XREF=gi:10946127 /UG=Hs.78202 SWISNF related, matrix associated, actin dependent regulator of chromatin, subfamily a, memb | AF254822 | 8.88 |
| protein phosphatase 1G (formerly 2C), magnesium-dependent, gamma isoform | NM_002707 | 8.77 |
| glucose phosphate isomerase | NM_000175 | 8.76 |
| proteasome (prosome, macropain) 26S subunit, non-ATPase, 8 | NM_002812 | 8.74 |

FIG. 4A-3

| | | |
|---|---|---|
| ribosomal protein S19 | BE259729 | 8.68 |
| eukaryotic translation elongation factor 1 alpha 1 | AL035687 | 8.48 |
| gb:L23518.1 /DEF=Human Ig rearranged gamma-chain, V-DXP1-JH4b, complete cds. /FEA=mRNA /DB_XREF=gi:385220 /FL=gb:L23518.1 | L23518 | 8.41 |
| ATP synthase, H+ transporting, mitochondrial F1 complex, delta subunit | NM_001687 | 8.41 |
| procollagen-proline, 2-oxoglutarate 4-dioxygenase (proline 4-hydroxylase), beta polypeptide (protein disulfide isomerase; thyroid hormone binding protein p55) | NM_000918 | 8.38 |
| endothelial differentiation-related factor 1 | AB002282 | 8.37 |
| acid phosphatase 1, soluble | BG035989 | 8.33 |
| chaperonin containing TCP1, subunit 3 (gamma) | NM_005998 | 8.32 |
| proteasome (prosome, macropain) subunit, alpha type, 7 | AL078633 | 8.23 |
| Consensus includes gb:AF043584.1 /DEF=Homo sapiens clone ASMneg1-b1 immunoglobulin lambda chain VJ region, (IGL) mRNA, partial cds. /FEA=mRNA /GEN=IGL /PROD=immunoglobulin lambda chain /DB_XREF=gi:2865479 /UG=Hs.287815 Homo sapiens clone ASMneg1-b1 immu | AF043584 | 8.21 |
| non-POU-domain-containing, octamer-binding | L14599 | 8.09 |
| CGI-51 protein | NM_015380 | 8.07 |
| adaptor-related protein complex 2, mu 1 subunit | NM_004068 | 7.95 |
| interferon regulatory factor 4 | NM_002460 | 7.90 |
| ribosomal protein S19 | NM_001022 | 7.90 |
| interferon stimulated gene (20kD) | NM_002201 | 7.88 |
| dolichyl-diphosphooligosaccharide-protein glycosyltransferase | D29643 | 7.80 |
| actin, beta | X00351 | 7.72 |
| major histocompatibility complex, class II, DR alpha | M60333 | 7.69 |
| major histocompatibility complex, class I, B | L42024 | 7.62 |
| major histocompatibility complex, class II, DR beta 5 | AJ297586 | 7.57 |
| actin, gamma 1 | AL567820 | 7.49 |
| NADH dehydrogenase (ubiquinone) 1 alpha subcomplex, 3 (9kD, B9) | NM_004542 | 7.48 |
| HLA-B associated transcript 1 | NM_004640 | 7.47 |
| ribosomal protein L18a | AC004692 | 7.36 |
| H2A histone family, member O | AI313324 | 7.31 |
| gb:U62824.1 /DEF=Homo sapiens HLA class I heavy chain (HLA-Cw*1701) mRNA, complete cds. /FEA=CDS /GEN=HLA-Cw*1701 /PROD=HLA class I heavy chain /DB_XREF=gi:1575443 /UG=Hs.287811 H.sapiens mRNA for HLA-C alpha chain (Cw*1701) /FL=gb:U62824.1 | U62824 | 7.31 |
| major histocompatibility complex, class II, DR alpha | M60334 | 7.27 |
| ribosomal protein S15 | NM_001018 | 7.26 |
| eukaryotic translation initiation factor 3, subunit 8 (110kD) | NM_003752 | 7.25 |
| U6 snRNA-associated Sm-like protein LSm7 | NM_016199 | 7.25 |
| eukaryotic translation elongation factor 2 | NM_001961 | 7.22 |
| membrane-spanning 4-domains, subfamily A, member 1 | X12530 | 7.13 |
| eukaryotic translation initiation factor 3, subunit 8 (110kD) | AA679705 | 7.11 |

FIG. 4A-4

| Description | Accession | Value |
|---|---|---|
| spermidine synthase | NM_003132 | 7.09 |
| polymerase (RNA) II (DNA directed) polypeptide J (13.3kD) | BG335629 | 7.09 |
| ribosomal protein S2 | NM_002952 | 7.03 |
| chemokine (C-X-C motif), receptor 4 (fusin) | AF348491 | 7.03 |
| RNA, U2 small nuclear | BC003629 | 7.00 |
| similar to HYPOTHETICAL 34.0 KDA PROTEIN ZK795.3 IN CHROMOSOME IV | BE747342 | 6.98 |
| origin recognition complex, subunit 5-like (yeast) | AF081459 | 6.94 |
| DEAD-box protein abstrakt | NM_016222 | 6.93 |
| immunoglobulin heavy constant mu | BC001872 | 6.90 |
| DKFZP564M182 protein | AK000822 | 6.88 |
| nuclear RNA helicase, DECD variant of DEAD box family | NM_005804 | 6.86 |
| stress-induced-phosphoprotein 1 (Hsp70/Hsp90-organizing protein) | BE886580 | 6.80 |
| immunoglobulin heavy constant mu | BG340548 | 6.76 |
| mutS homolog 6 (E. coli) | D89646 | 6.75 |
| tubulin, beta, 4 | AL565749 | 6.75 |
| major histocompatibility complex, class II, DR beta 1 | U65585 | 6.73 |
| T cell receptor beta locus | M15564 | 6.72 |
| major histocompatibility complex, class II, DP alpha 1 | M27487 | 6.62 |
| ribonucleotide reductase M1 polypeptide | AJ692974 | 6.62 |
| signal sequence receptor, delta (translocon-associated protein delta) | NM_006280 | 6.59 |
| seryl-tRNA synthetase | NM_006513 | 6.55 |
| eukaryotic translation initiation factor 2, subunit 3 (gamma, 52kD) | NM_001415 | 6.54 |
| protein phosphatase 1, regulatory subunit 7 | BF718769 | 6.52 |
| ancient ubiquitous protein 1 | NM_012103 | 6.52 |
| glutathione S-transferase pi | NM_000852 | 6.49 |
| polymerase (RNA) III (DNA directed) polypeptide K (12.3 kDa) | NM_016310 | 6.42 |
| ubiquinol-cytochrome c reductase core protein I | NM_003365 | 6.42 |
| proteasome (prosome, macropain) 26S subunit, non-ATPase, 4 | AB033605 | 6.41 |
| splicing factor, arginine/serine-rich 5 | AW084582 | 6.40 |
| SKB1 homolog (S. pombe) | NM_006109 | 6.32 |
| cell death-regulatory protein GRIM19 | NM_015965 | 6.20 |
| U6 snRNA-associated Sm-like protein | NM_012321 | 6.18 |
| eukaryotic translation initiation factor 3, subunit 2 (beta, 36kD) | U36764 | 6.17 |
| mitochondrial ribosomal protein S2 | NM_016034 | 6.17 |
| D123 gene product | NM_006023 | 6.16 |
| replication factor C (activator 1) 2 (40kD) | NM_002914 | 6.15 |
| membrane-spanning 4-domains, subfamily A, member 1 | BC002807 | 6.09 |
| Rab acceptor 1 (prenylated) | NM_006423 | 6.02 |
| eukaryotic translation initiation factor 3, subunit 9 (eta, 116kD) | BC001173 | 5.97 |
| ubiquitin C | M26880 | 5.97 |
| valosin-containing protein | AF100752 | 5.94 |
| ATP synthase, H+ transporting, mitochondrial F0 complex, subunit c (subunit 9), isoform 1 | AL080089 | 5.93 |
| CD22 antigen | X52785 | 5.93 |

FIG. 4A-5

| Description | Accession | Value |
|---|---|---|
| B lymphoid tyrosine kinase | NM_001715 | 5.89 |
| mitochondrial ribosomal protein S34 | NM_023936 | 5.88 |
| NADH dehydrogenase (ubiquinone) 1 beta subcomplex, 8 (19kD, ASHI) | NM_005004 | 5.88 |
| mitochondrial ribosomal protein L9 | AB049636 | 5.86 |
| ribosomal protein S2 | AI183766 | 5.85 |
| actin binding LIM protein 1 | NM_006720 | 5.84 |
| syntaxin 16 | AK026970 | 5.84 |
| major histocompatibility complex, class II, DR beta 4 | NM_021983 | 5.83 |
| protein kinase, DNA-activated, catalytic polypeptide | U34994 | 5.82 |
| ribosomal protein S28 | AC005011 | 5.81 |
| eukaryotic translation initiation factor 4A, isoform 1 | NM_001416 | 5.80 |
| ribosomal protein, large, P0 | BC003655 | 5.76 |
| NHP2 non-histone chromosome protein 2-like 1 (S. cerevisiae) | AF155235 | 5.76 |
| ATP citrate lyase | U18197 | 5.75 |
| Consensus includes gb:BF979419 /FEA=EST /DB_XREF=gi:12346634 /DB_XREF=est:602288246F1 /CLONE=IMAGE:4373914 /UG=Hs.119122 ribosomal protein L13a | BF979419 | 5.74 |
| glutaminyl-tRNA synthetase | NM_005051 | 5.74 |
| Consensus includes gb:AF005487.1 /DEF=Homo sapiens MHC class II antigen (DRB6) mRNA, HLA-DRB6*0201 allele, sequence. /FEA=mRNA /DB_XREF=gi:5915893 /UG=Hs.167385 Homo sapiens MHC class II antigen HLA-DRB6 mRNA, partial cds | AF005487 | 5.73 |
| eukaryotic translation initiation factor 3, subunit 9 (eta, 116kD) | NM_003751 | 5.71 |
| polymerase (RNA) II (DNA directed) polypeptide L (7.6kD) | BC005903 | 5.70 |
| mitochondrial ribosomal protein S12 | NM_021107 | 5.66 |
| ATP synthase, H+ transporting, mitochondrial F0 complex, subunit f, isoform 2 | NM_004889 | 5.66 |
| putative human HLA class II associated protein I | BE560202 | 5.65 |
| hypothetical protein | NM_016459 | 5.64 |
| membrane component, chromosome 11, surface marker 1 | BG258784 | 5.58 |
| hypothetical protein PRO1847 | AF119855 | 5.57 |
| proteasome (prosome, macropain) subunit, beta type, 7 | NM_002799 | 5.57 |
| cell division cycle 2-like 2 | AF067524 | 5.57 |
| similar to RIKEN cDNA 2310040G17 gene | BF972185 | 5.57 |
| putative transmembrane protein; homolog of yeast Golgi membrane protein Yif1p (Yip1p-interacting factor) | NM_020470 | 5.57 |
| tryptophanyl-tRNA synthetase | M61715 | 5.56 |
| ribosomal protein, large, P0 | NM_001002 | 5.56 |
| transcription factor Dp-1 | NM_007111 | 5.55 |
| guanine nucleotide binding protein (G protein), beta polypeptide 1 | AI741124 | 5.54 |
| actin, gamma 1 | AU145192 | 5.53 |
| hypothetical protein R33729_1 | AC005339 | 5.53 |
| CDW52 antigen (CAMPATH-1 antigen) | NM_001803 | 5.52 |
| ribosomal protein, large, P0 | AI953822 | 5.51 |
| actin related protein 2/3 complex, subunit 2 (34 kD) | AF279893 | 5.50 |
| guanine nucleotide binding protein (G protein), beta polypeptide 2- | NM_006098 | 5.49 |

FIG. 4A-6

| | | |
|---|---|---|
| like 1 | | |
| eukaryotic translation initiation factor 4A, isoform 1 | BC006210 | 5.47 |
| ubiquitin C | AB009010 | 5.47 |
| polymerase (RNA) II (DNA directed) polypeptide J (13.3kD) | AW402635 | 5.40 |
| hypothetical protein MGC4675 | AL118502 | 5.39 |
| ribosomal protein L10 | NM_006013 | 5.35 |
| v-yes-1 Yamaguchi sarcoma viral related oncogene homolog | M79321 | 5.33 |
| calpain, small subunit 1 | AD001527 | 5.31 |
| lymphocyte-specific protein tyrosine kinase | NM_005356 | 5.31 |
| anaphase promoting complex subunit 5 | BC001081 | 5.29 |
| ubiquitin-conjugating enzyme E2G 2 (UBC7 homolog, yeast) | BG395660 | 5.29 |
| kinesin 2 (60-70kD) | AA284075 | 5.29 |
| hematological and neurological expressed 1 | NM_016185 | 5.27 |
| ribosomal protein, large, P0 | BC005863 | 5.26 |
| immunoglobulin heavy constant mu | S74639 | 5.25 |
| proteasome (prosome, macropain) subunit, beta type, 8 (large multifunctional protease 7) | U17496 | 5.24 |
| ribosomal protein S3 | U14990 | 5.22 |
| proteasome (prosome, macropain) 26S subunit, ATPase, 3 | AL545523 | 5.21 |
| coronin, actin binding protein, 1A | U34690 | 5.19 |
| nuclear distribution gene C (A.nidulans) homolog | AF241788 | 5.17 |
| neutrophil cytosolic factor 4 (40kD) | NM_000631 | 5.17 |
| gb:M24668.1 /DEF=Human Ig rearranged H-chain V-region mRNA (C-D-JH4), complete cds. /FEA=mRNA /GEN=IGH@ /DB_XREF=gi:185198 /FL=gb:M24668.1 | M24668 | 5.16 |
| splicing factor, arginine/serine-rich 1 (splicing factor 2, alternate splicing factor) | NM_006924 | 5.16 |
| Cw1 antigen | M12679 | 5.11 |
| ariadne homolog 2 (Drosophila) | BC000422 | 5.09 |
| bromodomain-containing 2 | D42040 | 5.09 |
| major histocompatibility complex, class I, F | AW514210 | 5.08 |
| succinate dehydrogenase complex, subunit B, iron sulfur (Ip) | NM_003000 | 5.08 |
| NADH dehydrogenase (ubiquinone) Fe-S protein 3 (30kD) (NADH-coenzyme Q reductase) | NM_004551 | 5.07 |
| farnesyl-diphosphate farnesyltransferase 1 | BC003573 | 5.01 |
| transgelin 2 | NM_003564 | 4.98 |
| cytochrome c oxidase subunit IV isoform 1 | NM_001861 | 4.98 |
| integrin beta 4 binding protein | AF022229 | 4.95 |
| HIF-1 responsive RTP801 | NM_019058 | 4.93 |
| hypothetical protein PRO1068 | NM_018573 | 4.90 |
| putative breast adenocarcinoma marker (32kD) | NM_014453 | 4.88 |
| protein tyrosine phosphatase, receptor type, O | U20489 | 4.88 |
| hypothetical protein DKFZp434N185 | NM_025205 | 4.86 |
| tubulin alpha 6 | BC005946 | 4.85 |
| ribosomal protein L13 | AA789278 | 4.85 |
| Lysosomal-associated multispanning membrane protein-5 | AI589086 | 4.83 |
| protein kinase, cAMP-dependent, regulatory, type I, alpha (tissue | M18468 | 4.83 |

FIG. 4A-7

| | | |
|---|---|---|
| specific extinguisher 1) | | |
| ribosomal protein, large P2 | NM_001004 | 4.82 |
| eukaryotic translation initiation factor 4 gamma, 1 | AF104913 | 4.79 |
| transcription elongation factor B (SIII), polypeptide 2 (18kD, elongin B) | NM_007108 | 4.78 |
| karyopherin (importin) beta 3 | NM_002271 | 4.76 |
| lymphocyte cytosolic protein 1 (L-plastin) | J02923 | 4.74 |
| peroxiredoxin 1 | L19184 | 4.70 |
| heat shock protein 75 | NM_016292 | 4.70 |
| HLA-G histocompatibility antigen, class I, G | AF226990 | 4.70 |
| ribosomal protein S14 | AF116710 | 4.69 |
| cullin 1 | NM_003592 | 4.69 |
| heat shock 70kD protein 4 | BC002526 | 4.66 |
| NADH dehydrogenase (ubiquinone) flavoprotein 1 (51kD) | AF092131 | 4.65 |
| HSPC274 protein | NM_014145 | 4.63 |
| Consensus includes gb:BE305165 /FEA=EST /DB_XREF=gi:9177184 /DB_XREF=est:601186685T1 /CLONE=IMAGE:2959580 /UG=Hs.100623 phospholipase C, beta 3, neighbor pseudogene | BE305165 | 4.60 |
| MCM7 minichromosome maintenance deficient 7 (S. cerevisiae) | D55716 | 4.60 |
| tyrosine 3-monooxygenase/tryptophan 5-monooxygenase activation protein, zeta polypeptide | NM_003406 | 4.56 |
| lymphoid-restricted membrane protein | U10485 | 4.55 |
| tumor protein D52 | BG389015 | 4.53 |
| small nuclear ribonucleoprotein polypeptides B and B1 | J04564 | 4.53 |
| postmeiotic segregation increased 2-like 9 | U38979 | 4.52 |
| v-myb myeloblastosis viral oncogene homolog (avian)-like 2 | NM_002466 | 4.51 |
| T cell receptor beta locus | AF043179 | 4.46 |
| 7-dehydrocholesterol reductase | AW150953 | 4.45 |
| hypothetical protein FLJ20113 | AL523776 | 4.45 |
| eukaryotic translation initiation factor 3, subunit 4 (delta, 44kD) | BC000733 | 4.44 |
| baculoviral IAP repeat-containing 5 (survivin) | AB028869 | 4.41 |
| lymphoid-restricted membrane protein | NM_006152 | 4.39 |
| APEX nuclease (multifunctional DNA repair enzyme) | M80261 | 4.39 |
| Consensus includes gb:Z82202 /DEF=Human DNA sequence from clone RP1-34P24 on chromosome 22 Contains a pseudogene similar to ribosomal protein L35, ESTs, STSs and GSSs /FEA=CDS /DB_XREF=gi:4107193 /UG=Hs.247778 Human DNA sequence from clone RP1-34P24 on c | Z82202 | 4.39 |
| HSVI binding protein | NM_018694 | 4.39 |
| U6 snRNA-associated Sm-like protein | AA112507 | 4.38 |
| T cell receptor beta locus | AL559122 | 4.38 |
| casein kinase 2, beta polypeptide | NM_001320 | 4.38 |
| putative methyltransferase | NM_017528 | 4.37 |
| VPS28 protein | NM_016208 | 4.35 |
| lysosomal-associated membrane protein 1 | NM_005561 | 4.33 |
| bone marrow stromal cell antigen 2 | NM_004335 | 4.32 |

FIG. 4A-8

| | | |
|---|---|---|
| ribosomal protein L13a | BF942308 | 4.32 |
| transmembrane protein 4 | BC001027 | 4.32 |
| calreticulin | AD000092 | 4.30 |
| nuclear RNA export factor 1 | BC004904 | 4.30 |
| polymerase (RNA) II (DNA directed) polypeptide E (25kD) | AI554759 | 4.28 |
| nucleosome assembly protein 1-like 4 | NM_005969 | 4.25 |
| gb:AY014272.1 /DEF=Homo sapiens FKSG30 (FKSG30) mRNA, complete cds. /FEA=mRNA /GEN=FKSG30 /PROD=FKSG30 /DB_XREF=gi:12408251 /UG=Hs.315492 Homo sapiens FKSG30 (FKSG30) mRNA, complete cds /FL=gb:AY014272.1 | AY014272 | 4.25 |
| DEAD/H (Asp-Glu-Ala-Asp/His) box polypeptide 18 (Myc-regulated) | NM_006773 | 4.24 |
| KIAA0618 gene product | AI768378 | 4.23 |
| LIM domain only 2 (rhombotin-like 1) | NM_005574 | 4.23 |
| non-POU-domain-containing, octamer-binding | BC003129 | 4.22 |
| peptidylprolyl isomerase F (cyclophilin F) | NM_005729 | 4.19 |
| zinc finger protein 207 | BE871379 | 4.19 |
| emopamil binding protein (sterol isomerase) | AV702405 | 4.18 |
| unknown | NM_016209 | 4.17 |
| HS1 binding protein | NM_006118 | 4.17 |
| aconitase 2, mitochondrial | NM_001098 | 4.16 |
| H3 histone, family 3B (H3.3B) | NM_005324 | 4.15 |
| C2f protein | U72514 | 4.14 |
| ribosomal protein L13a | BC001675 | 4.14 |
| replication protein A1 (70kD) | NM_002945 | 4.12 |
| proteasome (prosome, macropain) 26S subunit, non-ATPase, 2 | NM_002808 | 4.12 |
| interferon-related developmental regulator 1 | NM_001550 | 4.11 |
| HLA-G histocompatibility antigen, class I, G | M90684 | 4.11 |
| RNB6 | NM_016337 | 4.11 |
| RNA binding motif protein 5 | U23946 | 4.10 |
| signal sequence receptor, beta (translocon-associated protein beta) | NM_003145 | 4.09 |
| guanine nucleotide binding protein (G protein), beta polypeptide 2 | NM_005273 | 4.09 |
| ribosomal protein S26 | NM_001029 | 4.08 |
| T cell receptor alpha locus | M12423 | 4.07 |
| translocase of inner mitochondrial membrane 13 homolog B (yeast) | NM_012458 | 4.07 |
| flap structure-specific endonuclease 1 | NM_004111 | 4.06 |
| translocating chain-associating membrane protein | NM_014294 | 4.06 |
| KIAA0217 protein | BC003381 | 4.06 |
| translocase of inner mitochondrial membrane 10 homolog (yeast) | NM_012456 | 4.05 |
| MADS box transcription enhancer factor 2, polypeptide B (myocyte enhancer factor 2B) | NM_005919 | 4.04 |
| tubulin alpha 6 | BC004949 | 4.03 |
| major histocompatibility complex, class I, E | M31183 | 4.03 |
| fuse-binding protein-interacting repressor | AF217197 | 4.02 |
| FK506 binding protein 1A (12kD) | BC005147 | 4.02 |

FIG. 4A-9

| | | |
|---|---|---|
| ATP synthase, H+ transporting, mitochondrial F1 complex, alpha subunit, isoform 1, cardiac muscle | AI587323 | 4.01 |
| DNA replication factor | AF321125 | 4.00 |
| HLA-B associated transcript 3 | BG028844 | 4.00 |
| NADH dehydrogenase (ubiquinone) 1 alpha subcomplex, 7 (14.5kD, B14.5a) | NM_005001 | 4.00 |
| poly(rC) binding protein 1 | U24223 | 4.00 |
| tetraspan 3 | NM_005724 | 3.99 |
| hydroxyacyl-Coenzyme A dehydrogenase/3-ketoacyl-Coenzyme A thiolase/enoyl-Coenzyme A hydratase (trifunctional protein), alpha subunit | AI972144 | 3.99 |
| cyclin-dependent kinase 4 | NM_000075 | 3.98 |
| solute carrier family 2 (facilitated glucose/fructose transporter), member 5 | BE560461 | 3.98 |
| hypothetical protein | BG257762 | 3.98 |
| T cell receptor alpha locus | M15565 | 3.96 |
| actin related protein 2/3 complex, subunit 1A (41 kD) | NM_006409 | 3.95 |
| T cell receptor alpha locus | L34703 | 3.94 |
| amyloid beta (A4) precursor-like protein 2 | AW001847 | 3.94 |
| translocase of inner mitochondrial membrane 23 homolog (yeast) | NM_006327 | 3.93 |
| B-cell translocation gene 1, anti-proliferative | AL535380 | 3.93 |
| PAI-1 mRNA-binding protein | BC003049 | 3.92 |
| adenylate kinase 2 | U39945 | 3.92 |

FIG. 4B-1

| gene | NCBI Accession Number | FOLD DECREASE |
|---|---|---|
| Consensus includes gb:AA292281 /FEA=EST /DB_XREF=gi:1940261 /DB_XREF=est:zt51b03.s1 /CLONE=IMAGE:725837 /UG=Hs.181307 H3 histone, family 3A | AA292281 | 15.15 |
| calreticulin | AI378706 | 13.38 |
| ribosomal protein S11 | BF680255 | 10.86 |
| ribosomal protein S19 | BC000023 | 9.95 |
| ribosomal protein, large P2 | BC005354 | 9.72 |
| Consensus includes gb:AW302047 /FEA=EST /DB_XREF=gi:6711724 /DB_XREF=est:xr52f08.x1 /CLONE=IMAGE:2763783 /UG=Hs.76230 ribosomal protein S10 | AW302047 | 8.60 |
| Consensus includes gb:L48784 /DEF=050 Homo sapiens cDNA /FEA=mRNA /DB_XREF=gi:1066715 /UG=Hs.182426 ribosomal protein S2 | L48784 | 7.68 |
| Consensus includes gb:AJ249377.1 /DEF=Homo sapiens partial mRNA for human Ig lambda light chain variable region, clone MB91 (331 bp). /FEA=mRNA /GEN=IGLV /PROD=immunoglobulin lambda variable region /DB_XREF=gi:5911837 /UG=Hs.247898 Human anti-streptococ | AJ249377 | 7.66 |
| Consensus includes gb:D84143.1 /DEF=Human immunoglobulin (mAb59) light chain V region mRNA, partial sequence. /FEA=mRNA /PROD=immunoglobulin light chain V-J region /DB_XREF=gi:1255613 /UG=Hs.121508 Human immunoglobulin (mAb59) light chain V region mRNA, | D84143 | 7.60 |
| ribosomal protein L27a | BE737027 | 6.93 |
| emopamil binding protein (sterol isomerase) | N58493 | 6.41 |
| calreticulin | AA910371 | 5.40 |
| hypothetical protein PRO1843 | NM_018507 | 5.23 |
| Cluster Incl. AI201594:qc02h12.x1 Homo sapiens cDNA, 3 end /clone=IMAGE-1708487 /clone_end=3 /gb=AI201594 /gi=3754200 /ug=Hs.239333 /len=591 | AI201594 | 4.91 |
| ribosomal protein S20 | AF113008 | 4.69 |
| C-terminal binding protein 1 | BF984434 | 4.57 |
| KIAA0906 protein | AA909765 | 4.45 |
| ribosomal protein L27 | BE312027 | 4.42 |
| Consensus includes gb:AF044592 /DEF=Homo sapiens lymphocyte-predominant Hodgkins disease case 4 immunoglobulin heavy chain gene, variable region, partial cds /FEA=CDS /DB_XREF=gi:2852420 /UG=Hs.248077 Homo sapiens lymphocyte-predominant Hodgkins disease | AF044592 | 4.24 |
| hypothetical protein FLJ21034 | NM_024940 | 4.13 |
| aminopeptidase puromycin sensitive | BG153399 | 4.04 |
| immunoglobulin lambda locus | AF043586 | 4.00 |
| Consensus includes gb:AJ239383.1 /DEF=Homo sapiens mRNA | AJ239383 | 3.96 |

FIG. 4B-2

| Description | Accession | Value |
|---|---|---|
| for immunoglobulin heavy chain variable region, ID 31. /FEA=mRNA /GEN=IGHV /PROD=immunoglobulin heavy chain variable region /DB_XREF=gi:4456587 /UG=Hs.249245 Homo sapiens mRNA for single-chain anti killer cell immunoglobulin-like receptor, three domains, long cytoplasmic tail, 2 | X93596 | 3.81 |
| hypothetical protein FLJ12619 | BE465032 | 3.81 |
| lymphoid blast crisis oncogene | AF127481 | 3.78 |
| Consensus includes gb:AV719355 /FEA=EST /DB_XREF=gi:10816507 /DB_XREF=est:AV719355 /CLONE=GLCEMB06 /UG=Hs.97109 ESTs | AV719355 | 3.67 |
| alanine-glyoxylate aminotransferase 2-like 1 | NM_031279 | 3.63 |
| Cluster Incl. AI949010:wq36a07.x1 Homo sapiens cDNA, 3 end /clone=IMAGE-2473332 /clone_end=3 /gb=AI949010 /gi=5741320 /ug=Hs.104036 /len=457 | AI949010 | 3.59 |
| PCTAIRE protein kinase 1 | NM_006201 | 3.56 |
| ADP-ribosylation factor 6 | AA243143 | 3.49 |
| tyrosine 3-monooxygenase/tryptophan 5-monooxygenase activation protein, epsilon polypeptide | AA502643 | 3.42 |
| Consensus includes gb:BF973387 /FEA=EST /DB_XREF=gi:12340602 /DB_XREF=est:602242353F1 /CLONE=IMAGE:4330861 /UG=Hs.305989 Human DNA sequence from clone RP3-483K16 on chromosome 6p12.1-21.1. Contains (parts of) two novel genes, RPS16 (40S Ribosomal protein | BF973387 | 3.42 |
| G protein-coupled receptor kinase 6 | BG423052 | 3.37 |
| M10098 Human 18S rRNA sequence, length 1969 bases, middle target bases 647-1292 | M10098 | 3.33 |
| GM2 ganglioside activator protein | X61094 | 3.24 |
| dystrophia myotonica-containing WD repeat motif | L19267 | 3.24 |
| collagen, type I, alpha 1 | AI743621 | 3.24 |
| cathepsin S | BC002642 | 3.22 |
| translation initiation factor IF2 | AB018284 | 3.19 |
| hypothetical protein FLJ22965 | NM_022101 | 3.16 |
| coactivator-associated arginine methyltransferase-1 | AL529396 | 3.14 |
| JTV1 gene | AF116615 | 3.13 |
| RAB6 interacting, kinesin-like (rabkinesin 6) | NM_005733 | 3.10 |
| hypothetical protein FLJ20666 | NM_018333 | 3.06 |
| isocitrate dehydrogenase 1 (NADP+), soluble | NM_005896 | 3.04 |
| Consensus includes gb:AI524687 /FEA=EST /DB_XREF=gi:4438822 /DB_XREF=est:th12a07.x1 /CLONE=IMAGE:2118036 /UG=Hs.57969 phenylalanine-tRNA synthetase | AI524687 | 3.03 |
| Consensus includes gb:AL136179 /DEF=Human DNA sequence from clone RP3-322L4 on chromosome 6. Contains the SOX4 gene for SRY (sex determining region Y)-box 4, a pseudogene similar to predicted fly, worm and yeast genes, ESTs, STSs, GSSs and four CpG islan | AL136179 | 3.03 |
| nucleolar protein 4 | NM_003787 | 3.02 |

FIG. 4B-3

| Description | Accession | Value |
|---|---|---|
| ribosomal protein L38 | AW303136 | 3.02 |
| ribosomal protein L38 | BC000603 | 2.98 |
| Consensus includes gb:AW090043 /FEA=EST /DB_XREF=gi:6047387 /DB_XREF=est:xd01c05.x1 /CLONE=IMAGE:2592488 /UG=Hs.326464 Homo sapiens cDNA: FLJ21702 fis, clone COL09874 | AW090043 | 2.91 |
| Consensus includes gb:AW971415 /FEA=EST /DB_XREF=gi:8161260 /DB_XREF=est:EST383504 /UG=Hs.165337 ESTs | AW971415 | 2.90 |
| J04423 E coli bioB gene biotin synthetase (-5, -M, -3 represent transcript regions 5 prime, Middle, and 3 prime respectively) | J04423 | 2.88 |
| Consensus includes gb:AA890010 /FEA=EST /DB_XREF=gi:3016889 /DB_XREF=est:aj89h08.s1 /CLONE=IMAGE:1403679 /UG=Hs.50785 SEC22, vesicle trafficking protein (S. cerevisiae)-like 1 | AA890010 | 2.88 |
| gb:Z25437.1 /DEF=H.sapiens protein-tyrosine kinase gene, complete CDS. /FEA=mRNA /PROD=protein-tyrosine kinase /DB_XREF=gi:405752 /FL=gb:Z25437.1 | Z25437 | 2.87 |
| prefoldin 4 | NM_002623 | 2.85 |
| KIAA1046 protein | NM_014928 | 2.83 |
| ATPase, H+ transporting, lysosomal (vacuolar proton pump) non-catalytic accessory protein 1A (110/116kD) | NM_005177 | 2.81 |
| hypothetical protein FLJ10159 | NM_018013 | 2.80 |
| Consensus includes gb:BG109746 /FEA=EST /DB_XREF=gi:12603252 /DB_XREF=est:602280883F1 /CLONE=IMAGE:4368381 /UG=Hs.325625 Homo sapiens clone 23938 mRNA sequence | BG109746 | 2.79 |
| HIV-1 rev binding protein 2 | AI912583 | 2.76 |
| acidic epididymal glycoprotein-like 1 | X95238 | 2.75 |
| hypothetical protein FLJ12619 | AL136632 | 2.74 |
| hypothetical protein FLJ14107 | NM_025026 | 2.73 |
| Escherichia coli /REF=J04423 /DEF=E coli bioB gene biotin synthetase corresponding to nucleotides 2393-2682 of J04423 /LEN=1114 (-5, -M, -3 represent transcript regions 5 prime, Middle, and 3 prime respectively) | J04423 | 2.73 |
| E74-like factor 4 (ets domain transcription factor) | NM_001421 | 2.71 |
| ribonuclease P, 40kD subunit | NM_006638 | 2.71 |
| transducin (beta)-like 1 | AA724134 | 2.70 |
| cytochrome c oxidase subunit Vb | AI557312 | 2.70 |
| RAB5B, member RAS oncogene family | AF267863 | 2.68 |
| RAP2B, member of RAS oncogene family | NM_002886 | 2.67 |
| ATP-binding cassette, sub-family D (ALD), member 3 | NM_002858 | 2.67 |
| Consensus includes gb:AK025724.1 /DEF=Homo sapiens cDNA: FLJ22071 fis, clone HEP11691. /FEA=mRNA /DB_XREF=gi:10438333 /UG=Hs.326248 Homo sapiens cDNA: FLJ22071 fis, clone HEP11691 | AK025724 | 2.67 |
| solute carrier family 21 (organic anion transporter), member 6 | AB026257 | 2.65 |
| Consensus includes gb:AW971134 /FEA=EST /DB_XREF=gi:8160979 /DB_XREF=est:EST383221 /UG=Hs.292245 ESTs, Weakly similar to ALU1_HUMAN ALU | AW971134 | 2.64 |

FIG. 4B-4

SUBFAMILY J SEQUENCE CONTAMINATION WARNING
ENTRY H.sapiens

| Description | Accession | Value |
|---|---|---|
| orphan seven-transmembrane receptor, chemokine related | NM_016557 | 2.61 |
| Consensus includes gb:AL050065.1 /DEF=Homo sapiens mRNA; cDNA DKFZp566M043 (from clone DKFZp566M043). /FEA=mRNA /DB_XREF=gi:4884295 /UG=Hs.212587 Homo sapiens mRNA; cDNA DKFZp566M043 (from clone DKFZp566M043) | AL050065 | 2.61 |
| PAX transcription activation domain interacting protein 1 like | AI357401 | 2.60 |
| cytoskeleton-associated protein 4 | NM_006825 | 2.59 |
| KIAA0653 protein, B7-like protein | AF289028 | 2.59 |
| C-type (calcium dependent, carbohydrate-recognition domain) lectin, superfamily member 6 | AF200738 | 2.59 |
| epithelial membrane protein 3 | NM_001425 | 2.59 |
| ribosomal protein L37a | BE857772 | 2.59 |
| Consensus includes gb:AI345238 /FEA=EST /DB_XREF=gi:4082444 /DB_XREF=est:tb81b07.x1 /CLONE=IMAGE:2060725 /UG=Hs.111334 ferritin, light polypeptide | AI345238 | 2.59 |
| ATPase, H+ transporting, lysosomal (vacuolar proton pump) 9kD | AI252582 | 2.58 |
| Bloom syndrome | NM_000057 | 2.57 |
| cytochrome P450 isoform 4F12 | NM_023944 | 2.56 |
| H3 histone family, member C | NM_003531 | 2.56 |
| hypothetical protein FLJ22009 | NM_024745 | 2.56 |
| glycophorin E | NM_002102 | 2.55 |
| hypothetical protein FLJ10298 | NM_018050 | 2.55 |
| endomucin-1 | NM_016241 | 2.55 |
| cyclin G2 | AW134535 | 2.55 |
| hexokinase 2 | AI761561 | 2.54 |
| polymerase (DNA directed), eta | NM_006502 | 2.53 |
| cullin 5 | NM_003478 | 2.53 |
| PI-3-kinase-related kinase SMG-1 | BE000837 | 2.52 |
| PRO1880 protein | NM_014104 | 2.50 |
| helicase KIAA0054 | NM_014877 | 2.50 |
| M10098 Human 18S rRNA gene, complete (_5, _M, _3 represent transcript regions 5 prime, Middle, and 3 prime respectively) | M10098 | 2.50 |
| KIAA0889 protein | NM_015377 | 2.49 |
| hypothetical protein FLJ20897 | AI335509 | 2.49 |
| gamma-aminobutyric acid (GABA) A receptor, alpha 5 | BF966183 | 2.49 |
| translation initiation factor IF2 | BE138647 | 2.48 |
| SCAN domain-containing 2 | AF244812 | 2.47 |
| inhibin, beta C | NM_005538 | 2.47 |
| M10098 Human 18S rRNA sequence, length 1969 bases, 3 prime target bases 1293-1938 | M10098 | 2.47 |
| cysteine-rich motor neuron 1 | BG546884 | 2.47 |
| mitochondrial ribosomal protein S12 | R68573 | 2.47 |
| hypothetical protein FLJ10357 | NM_018071 | 2.47 |
| mannan-binding lectin serine protease 1 (C4/C2 activating | BC000587 | 2.45 |

FIG. 4B-5

| | | |
|---|---|---|
| component of Ra-reactive factor) | | |
| thiopurine S-methyltransferase | U12387 | 2.45 |
| sorting nexin 4 | AA524345 | 2.45 |
| golgi associated, gamma adaptin ear containing, ARF binding protein 1 | AW001443 | 2.45 |
| Escherichia coli /REF=J04423 /DEF=E coli bioB gene biotin synthetase corresponding to nucleotides 2772-3004 of J04423 /LEN=1114 (-5, -M, -3 represent transcript regions 5 prime, Middle, and 3 prime respectively) | J04423 | 2.44 |
| methionine adenosyltransferase II, alpha | AW301861 | 2.43 |
| Consensus includes gb:AK022473.1 /DEF=Homo sapiens cDNA FLJ12411 fis, clone MAMMA1002964. /FEA=mRNA /DB_XREF=gi:10433882 /UG=Hs.296722 Homo sapiens cDNA FLJ12411 fis, clone MAMMA1002964 | AK022473 | 2.43 |
| eukaryotic translation initiation factor 5A | AA393940 | 2.42 |
| tumor necrosis factor alpha-inducible cellular protein containing leucine zipper domains; Huntingtin interacting protein L; transcrption factor IIIA-interacting protein | NM_021980 | 2.42 |
| J04423 E coli bioB gene biotin synthetase (-5, -M, -3 represent transcript regions 5 prime, Middle, and 3 prime respectively) | J04423 | 2.42 |
| SH3-domain GRB2-like 3 | AF036269 | 2.42 |
| hypothetical protein FLJ13078 | AK023140 | 2.41 |
| serine/threonine-protein kinase PRP4 homolog | AA156948 | 2.41 |
| harakiri, BCL2 interacting protein (contains only BH3 domain) | U76376 | 2.41 |
| Consensus includes gb:AK021505.1 /DEF=Homo sapiens cDNA FLJ11443 fis, clone HEMBA1001330. /FEA=mRNA /DB_XREF=gi:10432701 /UG=Hs.297945 Homo sapiens cDNA FLJ11443 fis, clone HEMBA1001330 | AK021505 | 2.40 |
| glioma pathogenesis-related protein | U16307 | 2.40 |
| artemis protein | AK022922 | 2.40 |
| phosphodiesterase 10A | AF127480 | 2.40 |
| ubiquitin specific protease 15 | AF106069 | 2.38 |
| TGFB-induced factor (TALE family homeobox) | NM_003244 | 2.38 |
| PRO0478 protein | NM_014129 | 2.38 |
| artemis protein | NM_022487 | 2.37 |
| Consensus includes gb:AI915947 /FEA=EST /DB_XREF=gi:5635802 /DB_XREF=est:wg96e01.x1 /CLONE=IMAGE:2379096 /UG=Hs.28212 ESTs | AI915947 | 2.37 |
| triple functional domain (PTPRF interacting) | AL161955 | 2.36 |
| thromboxane A2 receptor | NM_001060 | 2.36 |
| KIAA1655 protein | AB051442 | 2.36 |
| Consensus includes gb:BF942161 /FEA=EST /DB_XREF=gi:12359481 /DB_XREF=est:nae87g10.x1 /CLONE=IMAGE:4118994 /UG=Hs.302797 ESTs | BF942161 | 2.35 |
| DnaJ (Hsp40) homolog, subfamily A, member 1 | AL534104 | 2.35 |
| hypothetical protein FLJ22479 | NM_024900 | 2.35 |
| transforming, acidic coiled-coil containing protein 2 | AF220152 | 2.35 |
| KIAA0446 gene product | AB007915 | 2.34 |
| DKFZP547E1010 protein | N92920 | 2.33 |

FIG. 4B-6

| Description | Accession | Value |
|---|---|---|
| Consensus includes gb:AL157484.1 /DEF=Homo sapiens mRNA; cDNA DKFZp762M127 (from clone DKFZp762M127). /FEA=mRNA /DB_XREF=gi:7018527 /UG=Hs.22483 Homo sapiens mRNA; cDNA DKFZp762M127 (from clone DKFZp762M127) | AL157484 | 2.33 |
| kinectin 1 (kinesin receptor) | BF589024 | 2.33 |
| colony stimulating factor 2 receptor, alpha, low-affinity (granulocyte-macrophage) | L29349 | 2.32 |
| DEAD/H (Asp-Glu-Ala-Asp/His) box binding protein 1 | AI348378 | 2.32 |
| hypothetical protein FLJ23548 | NM_024590 | 2.32 |
| MAD, mothers against decapentaplegic homolog (Drosophila) interacting protein, receptor activation anchor | NM_007323 | 2.32 |
| Consensus includes gb:BC004344.1 /DEF=Homo sapiens, clone IMAGE:3633354, mRNA, partial cds. /FEA=mRNA /PROD=Unknown (protein for IMAGE:3633354) /DB_XREF=gi:13279286 /UG=Hs.5019 Homo sapiens, clone IMAGE:3633354, mRNA, partial cds | BC004344 | 2.32 |
| Consensus includes gb:R33964 /FEA=EST /DB_XREF=gi:789822 /DB_XREF=est:yh74c03.r1 /CLONE=IMAGE:135460 /UG=Hs.288681 Homo sapiens cDNA FLJ11022 fis, clone PLACE1003771 | R33964 | 2.31 |
| prostate derived STE20-like kinase PSK | NM_016151 | 2.31 |
| putative protein O-mannosyltransferase | NM_013382 | 2.30 |
| Consensus includes gb:AK021440.1 /DEF=Homo sapiens cDNA FLJ11378 fis, clone HEMBA1000456. /FEA=mRNA /DB_XREF=gi:10432625 /UG=Hs.6937 hypothetical protein FLJ10276 | AK021440 | 2.30 |
| Consensus includes gb:AL080160.1 /DEF=Homo sapiens mRNA; cDNA DKFZp434M054 (from clone DKFZp434M054). /FEA=mRNA /DB_XREF=gi:5262622 /UG=Hs.274517 Homo sapiens mRNA; cDNA DKFZp434M054 (from clone DKFZp434M054) | AL080160 | 2.30 |
| uncharacterized hypothalamus protein HT011 | BE565675 | 2.30 |
| S-adenosylmethionine decarboxylase 1 | NM_001634 | 2.29 |
| Consensus includes gb:BE786164 /FEA=EST /DB_XREF=gi:10207362 /DB_XREF=est:601474273F1 /CLONE=IMAGE:3877146 /UG=Hs.80285 Homo sapiens mRNA; cDNA DKFZp586C1723 (from clone DKFZp586C1723) | BE786164 | 2.29 |
| Consensus includes gb:BC005365.1 /DEF=Homo sapiens, clone IMAGE:3829438, mRNA, partial cds. /FEA=mRNA /PROD=Unknown (protein for IMAGE:3829438) /DB_XREF=gi:13529199 /UG=Hs.331237 Homo sapiens, clone IMAGE:3829438, mRNA, partial cds | BC005365 | 2.29 |
| Consensus includes gb:AW971254 /FEA=EST /DB_XREF=gi:8161099 /DB_XREF=est:EST383343 /UG=Hs.178433 ESTs | AW971254 | 2.28 |
| sema domain, immunoglobulin domain (Ig), short basic domain, secreted, (semaphorin) 3A | NM_006080 | 2.28 |
| Consensus includes gb:AF164963.1 /DEF=Homo sapiens tumor antigen NA88-A pseudogene, complete sequence. /FEA=mRNA /DB_XREF=gi:5901726 /UG=Hs.306576 Homo sapiens tumor | AF164963 | 2.28 |

FIG. 4B-7

| Description | Accession | Value |
|---|---|---|
| antigen NA88-A pseudogene, complete sequence | | |
| immunoglobulin heavy constant mu | S55735 | 2.28 |
| actin-related protein 3-beta | NM_020445 | 2.28 |
| CDC14 cell division cycle 14 homolog A (S. cerevisiae) | NM_003672 | 2.27 |
| DEAD/H (Asp-Glu-Ala-Asp/His) box polypeptide 17 (72kD) | NM_030881 | 2.27 |
| PABP-interacting protein 2 | AL043487 | 2.26 |
| DnaJ (Hsp40) homolog, subfamily B, member 9 | AL080081 | 2.26 |
| alcohol dehydrogenase 1C (class I), gamma polypeptide | NM_000669 | 2.25 |
| ecotropic viral integration site 2A | NM_014210 | 2.25 |
| Consensus includes gb:AI126492 /FEA=EST /DB_XREF=gi:3595006 /DB_XREF=est:qd82h06.x1 /CLONE=IMAGE:1736027 /UG=Hs.104258 Homo sapiens mRNA, exon 1, 2, 3, 4, clone:RES4-24A | AI126492 | 2.24 |
| N-myristoyltransferase 2 | NM_004808 | 2.24 |
| J04423 E coli bioB gene biotin synthetase (-5, -M, -3 represent transcript regions 5 prime, Middle, and 3 prime respectively) | J04423 | 2.24 |
| phosducin-like | NM_005388 | 2.24 |
| hypothetical protein FLJ22558 | NM_022747 | 2.24 |
| peptidyl-prolyl isomerase G (cyclophilin G) | AW340788 | 2.23 |
| KIAA0469 gene product | NM_014851 | 2.23 |
| putative lymphocyte G0/G1 switch gene | NM_015714 | 2.23 |
| Consensus includes gb:BE930512 /FEA=EST /DB_XREF=gi:10456588 /DB_XREF=est:RC6-GN0071-160800-021-D01 /UG=Hs.168732 ESTs | BE930512 | 2.23 |
| A kinase (PRKA) anchor protein 1 | BC000729 | 2.23 |
| aldehyde dehydrogenase 4 family, member A1 | U24267 | 2.23 |
| Consensus includes gb:BF573849 /FEA=EST /DB_XREF=gi:11647561 /DB_XREF=est:602132053F1 /CLONE=IMAGE:4271340 /UG=Hs.96343 ESTs, Weakly similar to ALUC_HUMAN !!!! ALU CLASS C WARNING ENTRY !!! H.sapiens | BF573849 | 2.22 |
| ATPase, Class I, type 8B, member 1 | BG252666 | 2.22 |
| Consensus includes gb:AI701156 /FEA=EST /DB_XREF=gi:4989056 /DB_XREF=est:we10f09.x1 /CLONE=IMAGE:2340713 /UG=Hs.6580 Homo sapiens cDNA: FLJ23227 fis, clone CAE00645, highly similar to AF052138 Homo sapiens clone 23718 mRNA sequence | AI701156 | 2.22 |
| stress 70 protein chaperone, microsome-associated, 60kD | AI718418 | 2.22 |
| gb:U61167.1 /DEF=Human SH3 domain-containing protein SH3P18 mRNA, complete cds. /FEA=mRNA /PROD=SH3 domain-containing protein SH3P18 /DB_XREF=gi:1438934 /UG=Hs.330549 Human SH3 domain-containing protein SH3P18 mRNA, complete cds /FL=gb:U61167.1 | U61167 | 2.22 |
| hypothetical protein FLJ23185 | NM_025056 | 2.21 |
| adenylate cyclase 7 | NM_001114 | 2.21 |
| Consensus includes gb:AL163202 /DEF=Homo sapiens chromosome 21 segment HS21C002 /FEA=CDS /DB_XREF=gi:7717242 /UG=Hs.289121 Homo sapiens chromosome 21 segment HS21C002 | AL163202 | 2.21 |

FIG. 4B-8

| | | |
|---|---|---|
| helicase-moi | BF590131 | 2.21 |
| Consensus includes gb:R06655 /FEA=EST /DB_XREF=gi:757275 /DB_XREF=est:yf10e02.r1 /CLONE=IMAGE:126458 /UG=Hs.188518 ESTs, Moderately similar to AF078844 1 hqp0376 protein H.sapiens | R06655 | 2.21 |
| hypothetical protein FLJ23311 | NM_024680 | 2.21 |
| xylulokinase (H. influenzae) homolog | AA777793 | 2.21 |
| islet cell autoantigen 1 (69kD) | BC005922 | 2.20 |
| Escherichia coli /REF=J04423 /DEF=E coli bioB gene biotin synthetase corresponding to nucleotides 2071-2304 of J04423 /LEN=1114 (-5, -M, -3 represent transcript regions 5 prime, Middle, and 3 prime respectively) | J04423 | 2.20 |
| degenerative spermatocyte homolog, lipid desaturase (Drosophila) | BC000961 | 2.20 |
| high-mobility group 20B | BC002552 | 2.19 |
| Consensus includes gb:AI984051 /FEA=EST /DB_XREF=gi:5811270 /DB_XREF=est:wt52h03.x1 /CLONE=IMAGE:2511125 /UG=Hs.11861 thyroid hormone receptor-associated protein, 240 kDa subunit /FL=gb:AF117754.1 gb:NM_005121.1 | AI984051 | 2.19 |
| Consensus includes gb:AI683552 /FEA=EST /DB_XREF=gi:4893734 /DB_XREF=est:tx67h02.x1 /CLONE=IMAGE:2274675 /UG=Hs.201605 ESTs, Moderately similar to ALU8_HUMAN ALU SUBFAMILY SX SEQUENCE CONTAMINATION WARNING ENTRY H.sapiens | AI683552 | 2.19 |
| Consensus includes gb:AI393960 /FEA=EST /DB_XREF=gi:4223507 /DB_XREF=est:tg11d04.x1 /CLONE=IMAGE:2108455 /UG=Hs.274851 ESTs | AI393960 | 2.19 |
| CGI-58 protein | NM_016006 | 2.19 |
| PDZ domain containing guanine nucleotide exchange factor(GEF)1 | AV654984 | 2.18 |
| hypothetical protein FLJ12985 | NM_024924 | 2.18 |
| SHB adaptor protein (a Src homology 2 protein) | NM_003028 | 2.18 |
| WNT1 inducible signaling pathway protein 3 | AF143679 | 2.17 |
| hypothetical protein FLJ20274 | NM_017736 | 2.17 |
| solute carrier family 16 (monocarboxylic acid transporters), member 7 | NM_004731 | 2.17 |
| Consensus includes gb:AA780524 /FEA=EST /DB_XREF=gi:2839855 /DB_XREF=est:ac71f01.s1 /CLONE=IMAGE:868057 /UG=Hs.294072 ESTs, Weakly similar to ALU1_HUMAN ALU SUBFAMILY J SEQUENCE CONTAMINATION WARNING ENTRY H.sapiens | AA780524 | 2.17 |
| hypothetical protein FLJ12619 | BG252842 | 2.17 |
| M10098 Human 18S rRNA gene, complete (_5, _M, _3 represent transcript regions 5 prime, Middle, and 3 prime respectively) | M10098 | 2.17 |
| J04423 E coli bioC protein (-5 and -3 represent transcript regions 5 prime and 3 prime respectively) | J04423 | 2.17 |
| coat protein gamma-cop | NM_016128 | 2.16 |
| a disintegrin and metalloproteinase domain 17 (tumor necrosis factor, alpha, converting enzyme) | NM_003183 | 2.16 |
| ring finger protein 2 | NM_007212 | 2.16 |

FIG. 4B-9

| | | |
|---|---|---|
| hypothetical protein FLJ10697 | NM_018181 | 2.16 |
| E3 ubiquitin ligase SMURF2 | AY014180 | 2.16 |
| kelch-like 2, Mayven (Drosophila) | NM_007246 | 2.16 |
| Consensus includes gb:AK023911.1 /DEF=Homo sapiens cDNA FLJ13849 fis, clone THYRO1000865. /FEA=mRNA /DB_XREF=gi:10435992 /UG=Hs.181810 Homo sapiens cDNA FLJ13849 fis, clone THYRO1000865 | AK023911 | 2.15 |
| NADH dehydrogenase (ubiquinone) 1 alpha subcomplex, 2 (8kD, B8) | AA993683 | 2.15 |
| Cluster Incl. C18318:C18318 Homo sapiens cDNA, 5 end /clone=GEN-560E03 /clone_end=5 /gb=C18318 /gi=1579920 /ug=Hs.123469 /len=519 | C18318 | 2.15 |
| Consensus includes gb:AF043583.1 /DEF=Homo sapiens clone ASMneg1-b3 immunoglobulin lambda chain VJ region, (IGL) mRNA, partial cds. /FEA=mRNA /GEN=IGL /PROD=immunoglobulin lambda chain /DB_XREF=gi:2865477 /UG=Hs.248083 Homo sapiens clone ASMneg1-b3 immu | AF043583 | 2.15 |
| hypothetical protein 384D8_6 | BC000473 | 2.14 |
| KIAA1659 protein | AB051446 | 2.13 |
| Treacher Collins-Franceschetti syndrome 1 | AW167713 | 2.13 |
| Consensus includes gb:AA629050 /FEA=EST /DB_XREF=gi:2541437 /DB_XREF=est:zu84a06.s1 /CLONE=IMAGE:744658 /UG=Hs.50760 ESTs, Highly similar to BimL H.sapiens | AA629050 | 2.12 |
| apolipoprotein L, 2 | BC004395 | 2.12 |
| type 1 tumor necrosis factor receptor shedding aminopeptidase regulator | AF183569 | 2.12 |
| Consensus includes gb:AL137378.1 /DEF=Homo sapiens mRNA; cDNA DKFZp434K1126 (from clone DKFZp434K1126). /FEA=mRNA /DB_XREF=gi:6807908 /UG=Hs.306455 Homo sapiens mRNA; cDNA DKFZp434K1126 (from clone DKFZp434K1126) | AL137378 | 2.12 |
| proteasome (prosome, macropain) 26S subunit, non-ATPase, 12 | NM_002816 | 2.12 |
| synaptojanin 2 | AK026758 | 2.12 |
| Consensus includes gb:AW970881 /FEA=EST /DB_XREF=gi:8160726 /DB_XREF=est:EST382964 /UG=Hs.205660 ESTs | AW970881 | 2.11 |
| putative N6-DNA-methyltransferase | NM_013240 | 2.11 |
| cathepsin D (lysosomal aspartyl protease) | AI560951 | 2.11 |
| hematopoietic PBX-interacting protein | AI348545 | 2.11 |
| tuftelin-interacting protein | NM_012143 | 2.11 |
| phosphatidylinositol 4-kinase, catalytic, beta polypeptide | U81802 | 2.11 |
| phosphoribosyl pyrophosphate synthetase 2 | NM_002765 | 2.10 |
| WW domain-containing protein 1 | AU155187 | 2.10 |
| Escherichia coli /REF=J04423 /DEF=E coli bioC protein corresponding to nucleotides 4257-4573 of J04423 /LEN=777 (-5 and -3 represent transcript regions 5 prime and 3 prime respectively) | J04423 | 2.09 |
| carboxypeptidase N, polypeptide 2, 83kD | J05158 | 2.09 |
| cofactor required for Sp1 transcriptional activation, subunit 9 | BC005250 | 2.09 |

FIG. 4B-10

| | | |
|---|---|---|
| (33kD) | | |
| carcinoembryonic antigen-related cell adhesion molecule 1 (biliary glycoprotein) | D12502 | 2.09 |
| Consensus includes gb:AK026847.1 /DEF=Homo sapiens cDNA: FLJ23194 fis, clone REC00490. /FEA=mRNA /DB_XREF=gi:10439802 /UG=Hs.306887 Homo sapiens cDNA: FLJ23194 fis, clone REC00490 | AK026847 | 2.09 |
| NY-REN-58 antigen | NM_016122 | 2.09 |
| solute carrier family 16 (monocarboxylic acid transporters), member 1 | BF511091 | 2.08 |
| transporter 2, ATP-binding cassette, sub-family B (MDR/TAP) | M74447 | 2.08 |
| KIAA0669 gene product | NM_014779 | 2.08 |
| GABA(A) receptors associated protein like 3 | AF180519 | 2.08 |
| cytochrome P450, subfamily IIC (mephenytoin 4-hydroxylase), polypeptide 19 | X65962 | 2.08 |
| choline/ethanolaminephosphotransferase | NM_006090 | 2.07 |
| KIAA0304 gene product | AF105279 | 2.07 |
| enolase 1, (alpha) | U88968 | 2.07 |
| H2A histone family, member X | H51429 | 2.07 |
| ALEX3 protein | NM_016607 | 2.07 |
| Consensus includes gb:AK026825.1 /DEF=Homo sapiens cDNA: FLJ23172 fis, clone LNG10005. /FEA=mRNA /DB_XREF=gi:10439771 /UG=Hs.306885 Homo sapiens cDNA: FLJ23172 fis, clone LNG10005 | AK026825 | 2.07 |
| hypothetical protein FLJ20059 | NM_017644 | 2.07 |
| potassium inwardly-rectifying channel, subfamily J, member 8 | NM_004982 | 2.07 |
| early lymphoid activation protein | L22650 | 2.07 |
| KIAA0874 protein | X80821 | 2.06 |
| somatostatin receptor 4 | NM_001052 | 2.06 |
| tankyrase, TRF1-interacting ankyrin-related ADP-ribose polymerase 2 | NM_025235 | 2.06 |
| immunoglobulin heavy constant gamma 3 (G3m marker) | BF002659 | 2.06 |
| transmembrane activator and CAML interactor | NM_012452 | 2.05 |
| RAD54, S. cerevisiae, homolog of, B | NM_012415 | 2.05 |
| polymerase (RNA) II (DNA directed) polypeptide B (140kD) | AW770896 | 2.05 |
| FK506 binding protein 8 (38kD) | N95418 | 2.05 |
| translation initiation factor IF2 | BG261322 | 2.05 |
| Consensus includes gb:AL050154.1 /DEF=Homo sapiens mRNA; cDNA DKFZp586L0120 (from clone DKFZp586L0120). /FEA=mRNA /DB_XREF=gi:4884366 /UG=Hs.98314 Homo sapiens mRNA; cDNA DKFZp586L0120 (from clone DKFZp586L0120) | AL050154 | 2.05 |
| Consensus includes gb:AU147017 /FEA=EST /DB_XREF=gi:11008538 /DB_XREF=est:AU147017 /CLONE=HEMBB1002152 /UG=Hs.301905 Homo sapiens cDNA FLJ14080 fis, clone HEMBB1002152 | AU147017 | 2.05 |
| G protein-coupled receptor 1 | AL046992 | 2.05 |
| protease, serine, 21 (testisin) | NM_006799 | 2.05 |
| hypothetical protein FLJ10496 | NM_018114 | 2.05 |

FIG. 4B-11

| | | |
|---|---|---|
| pregnancy specific beta-1-glycoprotein 11 | NM_002785 | 2.05 |
| RAN binding protein 1 | AI221318 | 2.04 |
| hypothetical protein FLJ12151 | AK022213 | 2.04 |
| Consensus includes gb:AK022174.1 /DEF=Homo sapiens cDNA FLJ12112 fis, clone MAMMA1000043. /FEA=mRNA /DB_XREF=gi:10433510 /UG=Hs.288793 Homo sapiens cDNA FLJ12112 fis, clone MAMMA1000043 | AK022174 | 2.04 |
| transcription factor 4 | AK026674 | 2.04 |
| SRY (sex determining region Y)-box 4 | AI989477 | 2.04 |
| Consensus includes gb:AC004460 /DEF=Homo sapiens PAC clone RP5-1086D14 /FEA=CDS /DB_XREF=gi:2981263 /UG=Hs.307352 Homo sapiens PAC clone RP5-1086D14 | AC004460 | 2.03 |
| Consensus includes gb:AK023918.1 /DEF=Homo sapiens cDNA FLJ13856 fis, clone THYRO1000988. /FEA=mRNA /DB_XREF=gi:10436003 /UG=Hs.288489 Homo sapiens cDNA FLJ13856 fis, clone THYRO1000988 | AK023918 | 2.03 |
| SEC24 related gene family, member D (S. cerevisiae) | NM_014822 | 2.03 |
| hypothetical protein FLJ11336 | NM_018393 | 2.03 |
| checkpoint suppressor 1 | AA860806 | 2.03 |
| Consensus includes gb:AF070647.1 /DEF=Homo sapiens clone 24438 mRNA sequence. /FEA=mRNA /DB_XREF=gi:3283921 /UG=Hs.124126 Homo sapiens clone 24438 mRNA sequence | AF070647 | 2.03 |
| translin | AI659180 | 2.02 |
| neuropilin 2 | AA295257 | 2.02 |
| cysteine-rich motor neuron 1 | NM_016441 | 2.02 |
| S100 calcium binding protein A11 (calgizzarin) | NM_005620 | 2.02 |
| gb:NM_017648.1 /DEF=Homo sapiens hypothetical protein FLJ20063 (FLJ20063), mRNA. /FEA=mRNA /GEN=FLJ20063 /PROD=hypothetical protein FLJ20063 /DB_XREF=gi:8923068 /UG=Hs.5940 hypothetical protein FLJ20063 /FL=gb:AB035807.1 gb:NM_017648.1 | NM_017648 | 2.02 |
| PC4 and SFRS1 interacting protein 1 | AF098482 | 2.02 |
| immunoglobulin heavy constant mu | S74639 | 2.02 |
| Consensus includes gb:AW301806 /FEA=EST /DB_XREF=gi:6711483 /DB_XREF=est:xr56e11.x1 /CLONE=IMAGE:2764172 /UG=Hs.150551 ESTs, Weakly similar to ALU1_HUMAN ALU SUBFAMILY J SEQUENCE CONTAMINATION WARNING ENTRY H.sapiens | AW301806 | 2.02 |
| ubiquitin protein ligase E3A (human papilloma virus E6-associated protein, Angelman syndrome) | BF588511 | 2.01 |
| adducin 2 (beta) | NM_017482 | 2.01 |
| thyroid hormone receptor-associated protein, 95-kD subunit | BG339606 | 2.01 |
| hypothetical protein PRO1942 | NM_018610 | 2.01 |
| HCF-binding transcription factor Zhangfei | AI206560 | 2.01 |
| protein phosphatase 2, regulatory subunit B (B56), gamma isoform | AW772123 | 2.01 |
| cofactor required for Sp1 transcriptional activation, subunit 2 (150kD) | AK023368 | 2.00 |
| F-box only protein 21 | AK001699 | 2.00 |
| gb:AF090895.1 /DEF=Homo sapiens clone HQ0117 PRO0117 | AF090895 | 2.00 |

FIG. 4B-12

| | | |
|---|---|---|
| mRNA, complete cds. /FEA=mRNA /PROD=PRO0117 /DB_XREF=gi:6690166 /UG=Hs.283919 Homo sapiens clone HQ0117 PRO0117 mRNA, complete cds /FL=gb:AF090895.1 | | |
| hypothetical protein PRO2849 | NM_022335 | 2.00 |
| Epstein-Barr virus induced gene 3 | NM_005755 | 2.00 |
| ATPase, Ca++ transporting, plasma membrane 1 | L14561 | 2.00 |
| tripartite motif-containing 2 | NM_015271 | 2.00 |
| brain-specific angiogenesis inhibitor 3 | AB011122 | 2.00 |
| Consensus includes gb:X78262.1 /DEF=H.sapiens mRNA for TRE5. /FEA=mRNA /DB_XREF=gi:587440 /UG=Hs.302178 H.sapiens mRNA for TRE5 | X78262 | 2.00 |
| neuregulin 2 | NM_013984 | 2.00 |
| v-myc myelocytomatosis viral oncogene homolog 2 (avian) | NM_005377 | 1.99 |
| calpain 9 (nCL-4) | AB038463 | 1.99 |
| zinc finger protein 281 | NM_012482 | 1.99 |
| hypothetical protein LOC57187 | BG403671 | 1.99 |
| hypothetical protein FLJ13166 | NM_025003 | 1.99 |
| gastric inhibitory polypeptide receptor | NM_000164 | 1.99 |
| activation-induced cytidine deaminase | NM_020661 | 1.99 |
| caspase 8, apoptosis-related cysteine protease | BF439983 | 1.99 |
| hypothetical protein FLJ20837 | NM_017964 | 1.99 |
| dickkopf homolog 2 (Xenopus laevis) | NM_014421 | 1.99 |
| lipopolysaccharide specific response-68 protein | NM_018678 | 1.98 |
| protein phosphatase, EF hand calcium-binding domain 2 | NM_006239 | 1.98 |
| hypothetical protein FLJ14346 | NM_025029 | 1.98 |
| membrane-spanning 4-domains, subfamily A, member 2 (Fc fragment of IgE, high affinity I, receptor for; beta polypeptide) | NM_000139 | 1.98 |
| Escherichia coli /REF=J04423 /DEF=E coli bioC protein corresponding to nucleotides 4609-4883 of J04423 /LEN=777 (-5 and -3 represent transcript regions 5 prime and 3 prime respectively) | J04423 | 1.98 |
| Consensus includes gb:BF035279 /FEA=EST /DB_XREF=gi:10743006 /DB_XREF=est:601457165F1 /CLONE=IMAGE:3860633 /UG=Hs.20325 ESTs, Moderately similar to pot. ORF V H.sapiens | BF035279 | 1.98 |
| KIAA1102 protein | AK027231 | 1.98 |
| mannosyl (alpha-1,6-)-glycoprotein beta-1,2-N-acetylglucosaminyltransferase | NM_002408 | 1.98 |
| ornithine decarboxylase antizyme inhibitor | AA047234 | 1.98 |
| BLu protein | NM_015896 | 1.98 |
| phosphatidylinositol-4-phosphate 5-kinase, type II, alpha | NM_005028 | 1.98 |
| clone FLB3816 | NM_016415 | 1.98 |
| thyroid hormone receptor interactor 11 | BC002656 | 1.97 |
| small inducible cytokine subfamily A (Cys-Cys), member 18, pulmonary and activation-regulated | Y13710 | 1.97 |
| hypothetical protein FLJ13162 | NM_025002 | 1.97 |
| Homer, neuronal immediate early gene, 1B | BE550452 | 1.97 |
| hypothetical protein FLJ14310 | NM_025028 | 1.97 |

FIG. 4B-13

| Description | Accession | Value |
|---|---|---|
| Consensus includes gb:U43604.1 /DEF=Human unidentified mRNA, partial sequence. /FEA=mRNA /DB_XREF=gi:1171236 /UG=Hs.159901 Human unidentified mRNA, partial sequence | U43604 | 1.97 |
| hydroxy-delta-5-steroid dehydrogenase, 3 beta- and steroid delta-isomerase 2 | NM_000198 | 1.97 |
| lipin 2 | U55968 | 1.97 |
| Consensus includes gb:AL050122.1 /DEF=Homo sapiens mRNA; cDNA DKFZp586E121 (from clone DKFZp586E121). /FEA=mRNA /DB_XREF=gi:4884330 /UG=Hs.274511 Homo sapiens mRNA; cDNA DKFZp586E121 (from clone DKFZp586E121) | AL050122 | 1.97 |
| gb:U96291.1 /DEF=Homo sapiens Ig kappa light chain variable region (VkII-A23) mRNA, complete cds. /FEA=mRNA /GEN=VkII-A23 /PROD=Ig kappa light chain variable region /DB_XREF=gi:2345027 /UG=Hs.113273 Homo sapiens Ig kappa light chain variable region (Vkl | U96291 | 1.97 |
| P3ECSL | NM_022164 | 1.97 |
| patched homolog (Drosophila) | AL044175 | 1.97 |
| WW domain binding protein 4 (formin binding protein 21) | AI734228 | 1.97 |
| neural cell adhesion molecule 2 | NM_004540 | 1.97 |
| hypothetical protein FLJ10254 | NM_018041 | 1.97 |
| ubiquitin-conjugating enzyme E2I (UBC9 homolog, yeast) | AA910614 | 1.96 |
| peptide YY, 2 (seminalplasmin) | NM_021093 | 1.96 |
| DnaJ (Hsp40) homolog, subfamily C, member 8 | AF116696 | 1.96 |
| KIAA0692 protein | AK025933 | 1.96 |
| UDP-glucuronic acid/UDP-N-acetylgalactosamine dual transporter | AI769637 | 1.96 |
| hypothetical protein FLJ20084 | NM_017659 | 1.96 |
| beta-amyloid binding protein precursor | BF968960 | 1.96 |
| glucocorticoid modulatory element binding protein 2 | AL133646 | 1.96 |
| coagulation factor V (proaccelerin, labile factor) | NM_000130 | 1.96 |
| KIAA0256 gene product | N52532 | 1.96 |
| Consensus includes gb:AK000864.1 /DEF=Homo sapiens cDNA FLJ10002 fis, clone HEMBA1000046. /FEA=mRNA /DB_XREF=gi:7021188 /UG=Hs.296522 Homo sapiens cDNA FLJ10002 fis, clone HEMBA1000046 | AK000864 | 1.96 |
| mitochondrial ribosomal protein L44 | NM_022915 | 1.96 |
| Consensus includes gb:AK022219.1 /DEF=Homo sapiens cDNA FLJ12157 fis, clone MAMMA1000500. /FEA=mRNA /DB_XREF=gi:10433569 /UG=Hs.98812 Homo sapiens cDNA FLJ12157 fis, clone MAMMA1000500 | AK022219 | 1.95 |
| jumonji homolog (mouse) | BG029530 | 1.95 |
| homeo box C5 | NM_018953 | 1.95 |
| cAMP responsive element binding protein-like 1 | U52696 | 1.95 |
| Alu-binding protein with zinc finger domain | NM_014274 | 1.95 |
| KIAA0319 gene product | NM_014809 | 1.95 |
| golgi autoantigen, golgin subfamily a, 4 | NM_002078 | 1.95 |
| hypothetical protein dJ462O23.2 | BC001265 | 1.95 |
| solute carrier family 16 (monocarboxylic acid transporters), member 4 | NM_004696 | 1.94 |
| tripartite motif-containing 5 | AF220028 | 1.94 |

FIG. 4B-14

| | | |
|---|---|---|
| integral membrane protein 2B | NM_021999 | 1.94 |
| ATPase, Cu++ transporting, alpha polypeptide (Menkes syndrome) | NM_000052 | 1.94 |
| cyclin E2 | NM_004702 | 1.94 |
| EphB3 | X75208 | 1.94 |
| hypothetical protein FLJ20097 | NM_017667 | 1.94 |
| DnaJ (Hsp40) homolog, subfamily B, member 9 | NM_012328 | 1.94 |
| polymerase (RNA) III (DNA directed) (32kD) | NM_006467 | 1.94 |
| aldehyde dehydrogenase 1 family, member B1 | BC001619 | 1.94 |
| Consensus includes gb:AA017721 /FEA=EST /DB_XREF=gi:1479910 /DB_XREF=est:ze39f11.s1 /CLONE=IMAGE:361389 /UG=Hs.49117 Homo sapiens mRNA; cDNA DKFZp564N1662 (from clone DKFZp564N1662) | AA017721 | 1.94 |
| nuclear transcription factor Y, alpha | AL031778 | 1.94 |

FIG. 4C-1

| Gene | NCBI Accession Number | FOLD INCREASE |
|---|---|---|
| gb:L23516.1 /DEF=Human Ig rearranged gamma-chain, V-DXP4-JH6c, complete cds. /FEA=mRNA /DB_XREF=gi:385218 /FL=gb:L23516.1 | L23516 | 43.37 |
| ubiquitin carrier protein | NM_014501 | 41.83 |
| glyceraldehyde-3-phosphate dehydrogenase | M33197 | 41.07 |
| Lysosomal-associated multispanning membrane protein-5 | NM_006762 | 37.81 |
| ribosomal protein L29 | NM_000992 | 37.44 |
| gb:L23518.1 /DEF=Human Ig rearranged gamma-chain, V-DXP1-JH4b, complete cds. /FEA=mRNA /DB_XREF=gi:385220 /FL=gb:L23518.1 | L23518 | 37.23 |
| immunoglobulin heavy constant mu | U80139 | 33.58 |
| adaptor-related protein complex 2, mu 1 subunit | NM_004068 | 32.97 |
| heat shock 90kD protein 1, beta | AI218219 | 32.61 |
| macrophage migration inhibitory factor (glycosylation-inhibiting factor) | NM_002415 | 30.90 |
| ferritin, light polypeptide | BG538564 | 30.50 |
| ornithine decarboxylase antizyme 1 | AF090094 | 30.15 |
| Consensus includes gb:L48784 /DEF=050 Homo sapiens cDNA /FEA=mRNA /DB_XREF=gi:1066715 /UG=Hs.182426 ribosomal protein S2 | L48784 | 30.09 |
| enolase 1, (alpha) | U88968 | 28.76 |
| ribosomal protein L29 | BF683426 | 28.60 |
| ribosomal protein L18 | NM_000979 | 28.20 |
| ribosomal protein L18a | NM_000980 | 28.19 |
| chaperonin containing TCP1, subunit 7 (eta) | NM_006429 | 27.91 |
| immunoglobulin heavy constant mu | BG340548 | 27.05 |
| HMT1 hnRNP methyltransferase-like 2 (S. cerevisiae) | NM_001536 | 25.89 |
| profilin 1 | NM_005022 | 24.23 |
| procollagen-proline, 2-oxoglutarate 4-dioxygenase (proline 4-hydroxylase), beta polypeptide (protein disulfide isomerase; thyroid hormone binding protein p55) | NM_000918 | 23.95 |
| procollagen-proline, 2-oxoglutarate 4-dioxygenase (proline 4-hydroxylase), beta polypeptide (protein disulfide isomerase; thyroid hormone binding protein p55) | J02783 | 23.56 |
| Consensus includes gb:D84143.1 /DEF=Human immunoglobulin (mAb59) light chain V region mRNA, partial sequence. /FEA=mRNA /PROD=immunoglobulin light chain V-J region /DB_XREF=gi:1255613 /UG=Hs.121508 Human immunoglobulin (mAb59) light chain V region mRNA. | D84143 | 22.30 |
| Consensus includes gb:AJ249377.1 /DEF=Homo sapiens partial mRNA for human Ig lambda light chain variable region, clone MB91 (331 bp). /FEA=mRNA /GEN=IGLV | AJ249377 | 21.91 |

FIG. 4C-2

| | | |
|---|---|---|
| /PROD=immunoglobulin lambda variable region /DB_XREF=gi:5911837 /UG=Hs.247898 Human anti-streptococ | | |
| U6 snRNA-associated Sm-like protein LSm7 | NM_016199 | 21.63 |
| polymerase (DNA directed), delta 2, regulatory subunit (50kD) | NM_006230 | 21.62 |
| ribosomal protein L8 | NM_000973 | 21.19 |
| transketolase (Wernicke-Korsakoff syndrome) | BF696840 | 21.11 |
| gb:AJ225092.1 /DEF=Homo sapiens mRNA for single-chain antibody, complete cds. /FEA=CDS /PROD=immunoglobulin /DB_XREF=gi:3090425 /UG=Hs.249245 Homo sapiens mRNA for single-chain antibody, complete cds /FL=gb:AJ225092.1 | AJ225092 | 20.48 |
| eukaryotic translation initiation factor 3, subunit 9 (eta, 116kD) | BC001173 | 19.28 |
| T-cell leukemia/lymphoma 1A | X82240 | 19.19 |
| ubiquitin-conjugating enzyme E2I (UBC9 homolog, yeast) | AA910614 | 19.08 |
| eukaryotic translation initiation factor 3, subunit 8 (110kD) | BC000533 | 18.47 |
| gb:L07950.1 /DEF=Homo sapiens MHC class I HLA B71 mRNA, complete cds. /FEA=CDS /GEN=HLA-B /PROD=MHC HLA B71 /DB_XREF=gi:307236 /FL=gb:L07950.1 | L07950 | 17.83 |
| glyceraldehyde-3-phosphate dehydrogenase | M33197 | 17.71 |
| MCM7 minichromosome maintenance deficient 7 (S. cerevisiae) | AF279900 | 17.26 |
| eukaryotic translation initiation factor 3, subunit 9 (eta, 116kD) | NM_003751 | 16.97 |
| pyruvate kinase, muscle | NM_002654 | 16.81 |
| replication factor C (activator 1) 2 (40kD) | M87338 | 16.75 |
| glyceraldehyde-3-phosphate dehydrogenase | BF689355 | 16.61 |
| spermidine synthase | NM_003132 | 16.57 |
| RNA polymerase II transcriptional regulation mediator (Med6, S. cerevisiae, homolog of) | NM_005466 | 16.27 |
| Rab acceptor 1 (prenylated) | NM_006423 | 16.24 |
| ribosomal protein L13 | AW574664 | 16.05 |
| Consensus includes gb:D84140.1 /DEF=Human immunoglobulin (mAb56) light chain V region mRNA, partial sequence. /FEA=mRNA /PROD=immunoglobulin light chain V-J region /DB_XREF=gi:1255610 /UG=Hs.248043 Human immunoglobulin (mAb56) light chain V region mRNA, | D84140 | 15.99 |
| CD22 antigen | X52785 | 15.89 |
| neutrophil cytosolic factor 4 (40kD) | NM_013416 | 15.70 |
| small EDRK-rich factor 2 | NM_005770 | 15.52 |
| glyceraldehyde-3-phosphate dehydrogenase | BE561479 | 15.36 |
| transketolase (Wernicke-Korsakoff syndrome) | L12711 | 15.06 |
| ATP synthase, H+ transporting, mitochondrial F1 complex, delta subunit | BE798517 | 14.96 |
| CGI-135 protein | NM_016068 | 14.94 |
| glucose phosphate isomerase | NM_000175 | 14.88 |
| pinin, desmosome associated protein | AF112222 | 14.86 |
| actin, beta | X00351 | 14.30 |
| Consensus includes gb:AF254822 /DEF=Homo sapiens SMARCA4 isoform (SMARCA4) gene, complete cds, alternatively spliced /FEA=CDS_2 /DB_XREF=gi:10946127 /UG=Hs.78202 SWISNF related, matrix associated, actin dependent regulator of | AF254822 | 14.20 |

FIG. 4C-3

| Description | Accession | Value |
|---|---|---|
| chromatin, subfamily a, memb fusion, derived from t(12;16) malignant liposarcoma | NM_004960 | 14.10 |
| ribosomal protein S5 | NM_001009 | 13.79 |
| polymerase (RNA) II (DNA directed) polypeptide J (13.3kD) | BG335629 | 13.39 |
| heat shock 90kD protein 1, beta | AF275719 | 13.32 |
| nuclease sensitive element binding protein 1 | BE966374 | 13.25 |
| ATP synthase, H+ transporting, mitochondrial F1 complex, delta subunit | NM_001687 | 13.24 |
| eukaryotic translation initiation factor 3, subunit 8 (110kD) | AA679705 | 13.07 |
| immunoglobulin heavy constant mu | BC001872 | 13.03 |
| actin, beta | X00351 | 12.99 |
| serine hydroxymethyltransferase 2 (mitochondrial) | NM_005412 | 12.93 |
| polymerase (RNA) II (DNA directed) polypeptide E (25kD) | AI554759 | 12.83 |
| maternal G10 transcript | NM_003910 | 12.80 |
| major histocompatibility complex, class I, B | D83043 | 12.59 |
| cell death-regulatory protein GRIM19 | NM_015965 | 12.48 |
| proteasome (prosome, macropain) 26S subunit, ATPase, 3 | AL545523 | 12.22 |
| valosin-containing protein | AF100752 | 12.15 |
| nuclear RNA helicase, DECD variant of DEAD box family | NM_005804 | 11.98 |
| eukaryotic translation initiation factor 3, subunit 8 (110kD) | NM_003752 | 11.83 |
| coronin, actin binding protein, 1A | U34690 | 11.81 |
| mitochondrial ribosomal protein S12 | NM_021107 | 11.76 |
| cold inducible RNA binding protein | NM_001280 | 11.67 |
| DEAD-box protein abstrakt | NM_016222 | 11.65 |
| putative transmembrane protein; homolog of yeast Golgi membrane protein Yif1p (Yip1p-interacting factor) | NM_020470 | 11.52 |
| protein phosphatase 1G (formerly 2C), magnesium-dependent, gamma isoform | NM_002707 | 11.46 |
| immunoglobulin heavy constant mu | S74639 | 11.35 |
| acid phosphatase 1, soluble | BG035989 | 11.32 |
| CGI-51 protein | NM_015380 | 11.29 |
| ATP synthase, H+ transporting, mitochondrial F0 complex, subunit c (subunit 9), isoform 1 | AL080089 | 11.11 |
| 7-dehydrocholesterol reductase | AW150953 | 11.06 |
| B lymphoid tyrosine kinase | NM_001715 | 11.05 |
| chaperonin containing TCP1, subunit 3 (gamma) | NM_005998 | 10.96 |
| cell division cycle 2-like 2 | AF067524 | 10.85 |
| dolichyl-diphosphooligosaccharide-protein glycosyltransferase | D29643 | 10.84 |
| transforming growth factor, beta 1 | BC000125 | 10.80 |
| ubiquinol-cytochrome c reductase core protein I | NM_003365 | 10.71 |
| NADH dehydrogenase (ubiquinone) 1 alpha subcomplex, 3 (9kD, B9) | NM_004542 | 10.61 |
| mitochondrial ribosomal protein S2 | NM_016034 | 10.58 |
| chaperonin containing TCP1, subunit 2 (beta) | AL545982 | 10.54 |
| ribosomal protein L18a | AC004692 | 10.40 |
| polymerase (RNA) II (DNA directed) polypeptide J (13.3kD) | AW402635 | 10.24 |
| interferon stimulated gene (20kD) | NM_002201 | 10.17 |

FIG. 4C-4

| Description | Accession | Value |
|---|---|---|
| gb:M24668.1 /DEF=Human Ig rearranged H-chain V-region mRNA (C-D-JH4), complete cds. /FEA=mRNA /GEN=IGH@ /DB_XREF=gi:185198 /FL=gb:M24668.1 | M24668 | 10.01 |
| proteasome (prosome, macropain) 26S subunit, non-ATPase, 8 | NM_002812 | 9.92 |
| proteasome (prosome, macropain) subunit, alpha type, 7 | AL078633 | 9.84 |
| ribosomal protein S19 | BE259729 | 9.82 |
| major histocompatibility complex, class II, DR beta 5 | AJ297586 | 9.71 |
| kinesin 2 (60-70kD) | AA284075 | 9.67 |
| similar to HYPOTHETICAL 34.0 KDA PROTEIN ZK795.3 IN CHROMOSOME IV | BE747342 | 9.65 |
| phosphoserine aminotransferase | NM_021154 | 9.50 |
| solute carrier family 2 (facilitated glucose/fructose transporter), member 5 | BE560461 | 9.50 |
| mutS homolog 6 (E. coli) | D89646 | 9.48 |
| gb:U62824.1 /DEF=Homo sapiens HLA class I heavy chain (HLA-Cw*1701) mRNA, complete cds. /FEA=CDS /GEN=HLA-Cw*1701 /PROD=HLA class I heavy chain /DB_XREF=gi:1575443 /UG=Hs.287811 H.sapiens mRNA for HLA-C alpha chain (Cw*1701) /FL=gb:U62824.1 | U62824 | 9.44 |
| major histocompatibility complex, class I, B | L42024 | 9.43 |
| stress-induced-phosphoprotein 1 (Hsp70/Hsp90-organizing protein) | BE886580 | 9.39 |
| nucleosome assembly protein 1-like 4 | NM_005969 | 9.31 |
| proteasome (prosome, macropain) 26S subunit, non-ATPase, 4 | AB033605 | 9.29 |
| ribosomal protein S19 | NM_001022 | 9.29 |
| replication factor C (activator 1) 2 (40kD) | NM_002914 | 9.28 |
| eukaryotic translation initiation factor 4 gamma, 1 | AF104913 | 9.27 |
| glutathione S-transferase pi | NM_000852 | 9.15 |
| signal sequence receptor, delta (translocon-associated protein delta) | NM_006280 | 9.05 |
| VPS28 protein | NM_016208 | 9.01 |
| DKFZP564M182 protein | AK000822 | 8.99 |
| 6-phosphogluconolactonase | NM_012088 | 8.94 |
| ribosomal protein S2 | NM_002952 | 8.88 |
| protein phosphatase 1, regulatory subunit 7 | BF718769 | 8.85 |
| ribosomal protein S15 | NM_001018 | 8.78 |
| translocase of inner mitochondrial membrane 13 homolog B (yeast) | NM_012458 | 8.77 |
| endothelial differentiation-related factor 1 | AB002282 | 8.75 |
| T cell receptor beta locus | M15564 | 8.72 |
| hypothetical protein R33729_1 | AC005339 | 8.61 |
| ubiquitin C | M26880 | 8.53 |
| major histocompatibility complex, class II, DR alpha | M60333 | 8.52 |
| non-POU-domain-containing, octamer-binding | L14599 | 8.52 |
| major histocompatibility complex, class II, DR alpha | M60334 | 8.36 |
| DNA replication factor | AF321125 | 8.34 |
| PRP8 pre-mRNA processing factor 8 homolog (yeast) | NM_006445 | 8.28 |
| SKB1 homolog (S. pombe) | NM_006109 | 8.28 |

FIG. 4C-5

| Description | Accession | Value |
|---|---|---|
| eukaryotic translation elongation factor 1 alpha 1 | AL035687 | 8.27 |
| KIAA0217 protein | BC003381 | 8.24 |
| major histocompatibility complex, class II, DR beta 1 | U65585 | 8.20 |
| ubiquitin-activating enzyme E1 (A1S9T and BN75 temperature sensitivity complementing) | NM_003334 | 8.14 |
| polymerase (RNA) III (DNA directed) polypeptide K (12.3 kDa) | NM_016310 | 8.11 |
| ATP synthase, H+ transporting, mitochondrial F0 complex, subunit f, isoform 2 | NM_004889 | 8.06 |
| glutaminyl-tRNA synthetase | NM_005051 | 8.04 |
| HLA-B associated transcript 1 | NM_004640 | 8.01 |
| Consensus includes gb:AF043584.1 /DEF=Homo sapiens clone ASMneg1-b1 immunoglobulin lambda chain VJ region, (IGL) mRNA, partial cds. /FEA=mRNA /GEN=IGL /PROD=immunoglobulin lambda chain /DB_XREF=gi:2865479 /UG=Hs.287815 Homo sapiens clone ASMneg1-b1 immu | AF043584 | 8.00 |
| ribosomal protein S14 | AF116710 | 7.98 |
| interferon regulatory factor 4 | NM_002460 | 7.94 |
| T cell receptor beta locus | AF043179 | 7.91 |
| HLA-B associated transcript 3 | BG028844 | 7.90 |
| bone marrow stromal cell antigen 2 | NM_004335 | 7.84 |
| integrin beta 4 binding protein | AF022229 | 7.76 |
| putative breast adenocarcinoma marker (32kD) | NM_014453 | 7.65 |
| polymerase (RNA) II (DNA directed) polypeptide L (7.6kD) | BC005903 | 7.63 |
| hypothetical protein PRO1847 | AF119855 | 7.60 |
| D123 gene product | NM_006023 | 7.54 |
| actin binding LIM protein 1 | NM_006720 | 7.53 |
| eukaryotic translation initiation factor 3, subunit 2 (beta, 36kD) | U36764 | 7.47 |
| T cell receptor beta locus | AL559122 | 7.45 |
| tubulin, beta, 4 | AL565749 | 7.39 |
| coatomer protein complex, subunit epsilon | NM_007263 | 7.35 |
| chromosome 14 open reading frame 3 | NM_012111 | 7.35 |
| major histocompatibility complex, class II, DP alpha 1 | M27487 | 7.30 |
| mitochondrial ribosomal protein S34 | NM_023936 | 7.28 |
| hepatitis delta antigen-interacting protein A | NM_006848 | 7.27 |
| peptidylprolyl isomerase F (cyclophilin F) | NM_005729 | 7.26 |
| nuclear RNA export factor 1 | BC004904 | 7.24 |
| ubiquitin C | AB009010 | 7.21 |
| transmembrane protein 4 | BC001027 | 7.20 |
| amyloid beta (A4) precursor-like protein 2 | AW001847 | 7.19 |
| hypothetical protein FLJ20113 | AL523776 | 7.19 |
| GCN1 general control of amino-acid synthesis 1-like 1 (yeast) | AI697055 | 7.16 |
| NHP2 non-histone chromosome protein 2-like 1 (S. cerevisiae) | AF155235 | 7.15 |
| eukaryotic translation initiation factor 4A, isoform 1 | NM_001416 | 7.13 |
| macrophage erythroblast attacher | NM_005882 | 7.11 |
| chemokine (C-X-C motif), receptor 4 (fusin) | AF348491 | 7.10 |
| calreticulin | AD000092 | 7.09 |
| ancient ubiquitous protein 1 | NM_012103 | 7.07 |

FIG. 4C-6

| Description | Accession | Value |
|---|---|---|
| emopamil binding protein (sterol isomerase) | AV702405 | 7.06 |
| putative human HLA class II associated protein I | BE560202 | 7.05 |
| suppression of tumorigenicity 14 (colon carcinoma, matriptase, epithin) | NM_021978 | 7.05 |
| proteasome (prosome, macropain) 26S subunit, non-ATPase, 3 | NM_002809 | 7.02 |
| GDP-mannose 4,6-dehydratase | NM_001500 | 7.01 |
| transcription factor Dp-1 | NM_007111 | 7.01 |
| v-myb myeloblastosis viral oncogene homolog (avian)-like 2 | NM_002466 | 6.90 |
| origin recognition complex, subunit 5-like (yeast) | AF081459 | 6.89 |
| Consensus includes gb:AF005487.1 /DEF=Homo sapiens MHC class II antigen (DRB6) mRNA, HLA-DRB6*0201 allele, sequence. /FEA=mRNA /DB_XREF=gi:5915893 /UG=Hs.167385 Homo sapiens MHC class II antigen HLA-DRB6 mRNA, partial cds | AF005487 | 6.89 |
| splicing factor, arginine/serine-rich 5 | AW084582 | 6.88 |
| Consensus includes gb:BE305165 /FEA=EST /DB_XREF=gi:9177184 /DB_XREF=est:601186685T1 /CLONE=IMAGE:2959580 /UG=Hs.100623 phospholipase C, beta 3, neighbor pseudogene | BE305165 | 6.88 |
| ATP-binding cassette, sub-family F (GCN20), member 2 | NM_005692 | 6.87 |
| adaptor-related protein complex 2, sigma 1 subunit | NM_021575 | 6.86 |
| U6 snRNA-associated Sm-like protein | NM_012321 | 6.86 |
| unknown | NM_016209 | 6.85 |
| major histocompatibility complex, class I, F | AW514210 | 6.84 |
| ribosomal protein S2 | AI183766 | 6.82 |
| HSVI binding protein | NM_018694 | 6.81 |
| CD79A antigen (immunoglobulin-associated alpha) | NM_001783 | 6.81 |
| major histocompatibility complex, class II, DR beta 4 | NM_021983 | 6.80 |
| FK506 binding protein precursor | NM_016594 | 6.77 |
| eukaryotic translation initiation factor 3, subunit 4 (delta, 44kD) | BC000733 | 6.77 |
| ADP-ribosylation factor 1 | AA580004 | 6.76 |
| hypothetical protein | NM_016459 | 6.74 |
| anaphase promoting complex subunit 5 | BC001081 | 6.74 |
| U6 snRNA-associated Sm-like protein | AA112507 | 6.69 |
| eukaryotic translation elongation factor 2 | NM_001961 | 6.68 |
| hypothetical protein MGC4675 | AL118502 | 6.67 |
| guanylate kinase 1 | BC006249 | 6.66 |
| SNRPN upstream reading frame | NM_022804 | 6.64 |
| mitochondrial ribosomal protein L23 | AI832239 | 6.62 |
| RNA, U2 small nuclear | BC003629 | 6.58 |
| membrane-spanning 4-domains, subfamily A, member 1 | X12530 | 6.57 |
| heat shock protein 75 | NM_016292 | 6.51 |
| transgelin 2 | NM_003564 | 6.50 |
| tryptophanyl-tRNA synthetase | M61715 | 6.47 |
| actin, gamma 1 | AL567820 | 6.46 |
| eukaryotic translation initiation factor 4A, isoform 1 | BC006210 | 6.45 |
| guanine nucleotide binding protein (G protein), beta polypeptide 1 | AI741124 | 6.45 |
| ribosomal protein, large, P0 | AI953822 | 6.43 |

FIG. 4C-7

| | | |
|---|---|---|
| ribonucleotide reductase M1 polypeptide | AI692974 | 6.42 |
| proteasome (prosome, macropain) 26S subunit, non-ATPase, 2 | NM_002808 | 6.42 |
| CD27-binding (Siva) protein | NM_006427 | 6.38 |
| small nuclear ribonucleoprotein polypeptides B and B1 | J04564 | 6.36 |
| membrane-spanning 4-domains, subfamily A, member 1 | BC002807 | 6.33 |
| ribosomal protein, large, P0 | NM_001002 | 6.32 |
| ribosomal protein, large, P0 | BC005863 | 6.30 |
| seb4D | AL109955 | 6.28 |
| ribosomal protein, large, P0 | BC003655 | 6.28 |
| mitochondrial ribosomal protein S16 | NM_016065 | 6.26 |
| CD27-binding (Siva) protein | AF033111 | 6.23 |
| sterol regulatory element binding transcription factor 2 | NM_004599 | 6.23 |
| CDW52 antigen (CAMPATH-1 antigen) | NM_001803 | 6.21 |
| ribosomal protein L10 | NM_006013 | 6.21 |
| cytochrome c oxidase subunit IV isoform 1 | NM_001861 | 6.19 |
| ribosomal protein S3 | U14990 | 6.17 |
| hydroxyacyl-Coenzyme A dehydrogenase/3-ketoacyl-Coenzyme A thiolase/enoyl-Coenzyme A hydratase (trifunctional protein), alpha subunit | AI972144 | 6.15 |
| neutrophil cytosolic factor 4 (40kD) | NM_000631 | 6.15 |
| NADH dehydrogenase (ubiquinone) flavoprotein 1 (51kD) | AF092131 | 6.14 |
| aconitase 2, mitochondrial | NM_001098 | 6.11 |
| ribosomal protein S26 | NM_001029 | 6.11 |
| HLA-G histocompatibility antigen, class I, G | AF226990 | 6.10 |
| SWI/SNF related, matrix associated, actin dependent regulator of chromatin, subfamily a, member 4 | AI744900 | 6.08 |
| DNA segment on chromosome 19 (unique) 1177 expressed sequence | NM_006114 | 6.08 |
| ribosomal protein L13 | AA789278 | 6.05 |
| proteasome (prosome, macropain) subunit, beta type, 7 | NM_002799 | 6.05 |
| lymphocyte-specific protein tyrosine kinase | NM_005356 | 6.04 |
| seryl-tRNA synthetase | NM_006513 | 6.04 |
| v-yes-1 Yamaguchi sarcoma viral related oncogene homolog | M79321 | 6.03 |
| HSPC142 protein | BC006244 | 6.02 |
| replication protein A1 (70kD) | NM_002945 | 5.99 |
| ubiquitin-conjugating enzyme E2G 2 (UBC7 homolog, yeast) | BG395660 | 5.98 |
| membrane component, chromosome 11, surface marker 1 | BG258784 | 5.96 |
| H1 histone family, member X | NM_006026 | 5.95 |
| Lysosomal-associated multispanning membrane protein-5 | AI589086 | 5.95 |
| PTD008 protein | NM_016145 | 5.95 |
| poly(rC) binding protein 1 | U24223 | 5.94 |
| polyglutamine binding protein 1 | AB041836 | 5.93 |
| ariadne homolog 2 (Drosophila) | BC000422 | 5.93 |
| MADS box transcription enhancer factor 2, polypeptide B (myocyte enhancer factor 2B) | NM_005919 | 5.92 |
| translocase of inner mitochondrial membrane 44 homolog (yeast) | NM_006351 | 5.92 |
| intercellular adhesion molecule 2 | NM_000873 | 5.91 |

FIG. 4C-8

| | | |
|---|---|---|
| bromodomain-containing 2 | D42040 | 5.91 |
| lysosomal-associated membrane protein 1 | NM_005561 | 5.91 |
| NADH dehydrogenase (ubiquinone) 1 beta subcomplex, 8 (19kD, ASHI) | NM_005004 | 5.87 |
| actin related protein 2/3 complex, subunit 2 (34 kD) | AF279893 | 5.84 |
| Consensus includes gb:BG334495 /FEA=EST /DB_XREF=gi:13140933 /DB_XREF=est:602461128F1 /CLONE=IMAGE:4577718 /UG=Hs.228201 ESTs, Moderately similar to AF118094 25 PRO1992 H.sapiens | BG334495 | 5.84 |
| isocitrate dehydrogenase 3 (NAD+) gamma | NM_004135 | 5.80 |
| mitochondrial ribosomal protein L9 | AB049636 | 5.80 |
| transcription elongation factor B (SIII), polypeptide 2 (18kD, elongin B) | NM_007108 | 5.80 |
| hypothetical protein | AI670847 | 5.80 |
| HSPC274 protein | NM_014145 | 5.77 |
| APEX nuclease (multifunctional DNA repair enzyme) | M80261 | 5.77 |
| hematological and neurological expressed 1 | NM_016185 | 5.75 |
| hypothetical protein DKFZp434N185 | NM_025205 | 5.75 |
| eukaryotic translation initiation factor 4E-like 3 | AF047695 | 5.75 |
| N-acylaminoacyl-peptide hydrolase | NM_001640 | 5.74 |
| KIAA0746 protein | AA522514 | 5.73 |
| calpain, small subunit 1 | AD001527 | 5.72 |
| interleukin enhancer binding factor 3, 90kD | AF147209 | 5.69 |
| DEAD/H (Asp-Glu-Ala-Asp/His) box polypeptide 18 (Myc-regulated) | NM_006773 | 5.67 |
| hypothetical protein MGC10715 | AL049650 | 5.67 |
| chloride intracellular channel 1 | AF034607 | 5.66 |
| CD79B antigen (immunoglobulin-associated beta) | NM_000626 | 5.64 |
| hydroxyacyl-Coenzyme A dehydrogenase, type II | NM_004493 | 5.64 |
| zinc finger protein 207 | BE871379 | 5.62 |
| ribosomal protein S28 | AC005011 | 5.61 |
| syntaxin 16 | AK026970 | 5.61 |
| nuclear prelamin A recognition factor | NM_012336 | 5.61 |
| cytochrome b-245, alpha polypeptide | NM_000101 | 5.60 |
| actin related protein 2/3 complex, subunit 1A (41 kD) | NM_006409 | 5.60 |
| mercaptopyruvate sulfurtransferase | NM_021126 | 5.57 |
| Consensus includes gb:BF979419 /FEA=EST /DB_XREF=gi:12346634 /DB_XREF=est:602288246F1 /CLONE=IMAGE:4373914 /UG=Hs.119122 ribosomal protein L13a | BF979419 | 5.57 |
| lymphocyte cytosolic protein 1 (L-plastin) | J02923 | 5.57 |
| NADH dehydrogenase (ubiquinone) Fe-S protein 3 (30kD) (NADH-coenzyme Q reductase) | NM_004551 | 5.56 |
| small nuclear ribonucleoprotein polypeptide A | NM_004596 | 5.55 |
| pre-mRNA processing factor 31 homolog (yeast) | BF342707 | 5.55 |
| protein phosphatase 1, catalytic subunit, alpha isoform | NM_002708 | 5.54 |
| Tu translation elongation factor, mitochondrial | NM_003321 | 5.54 |
| KIAA0618 gene product | AA514622 | 5.52 |

FIG. 4C-9

| | | |
|---|---|---|
| protein kinase, DNA-activated, catalytic polypeptide | U34994 | 5.51 |
| Cw1 antigen | M12679 | 5.50 |
| protein phosphatase 2 (formerly 2A), regulatory subunit A (PR 65), alpha isoform | NM_014225 | 5.49 |
| tyrosine 3-monooxygenase/tryptophan 5-monooxygenase activation protein, zeta polypeptide | NM_003406 | 5.49 |
| guanine nucleotide binding protein (G protein), beta polypeptide 2 | NM_005273 | 5.45 |
| TAP binding protein (tapasin) | AF029750 | 5.43 |
| solute carrier family 3 (activators of dibasic and neutral amino acid transport), member 2 | NM_002394 | 5.42 |
| signal sequence receptor, beta (translocon-associated protein beta) | NM_003145 | 5.41 |
| proteasome (prosome, macropain) subunit, beta type, 8 (large multifunctional protease 7) | U17496 | 5.36 |
| RNB6 | NM_016337 | 5.33 |
| glutathione peroxidase 1 | NM_000581 | 5.29 |
| KIAA0123 protein | BF570122 | 5.28 |
| flap structure-specific endonuclease 1 | NM_004111 | 5.27 |
| ATPase, H+ transporting, lysosomal (vacuolar proton pump) 21kD | BC005876 | 5.27 |
| putative methyltransferase | NM_017528 | 5.27 |
| RNA binding motif protein 5 | U23946 | 5.26 |
| GTP cyclohydrolase I feedback regulatory protein | NM_005258 | 5.25 |
| H2A histone family, member O | AI313324 | 5.25 |
| hypothetical protein R32184_1 | BC001648 | 5.25 |
| farnesyl-diphosphate farnesyltransferase 1 | BC003573 | 5.25 |
| glycoprotein, synaptic 2 | NM_004868 | 5.22 |
| peptidylprolyl isomerase E (cyclophilin E) | AF042386 | 5.21 |
| FK506 binding protein 1A (12kD) | BC005147 | 5.19 |
| guanine nucleotide binding protein (G protein), beta polypeptide 2-like 1 | NM_006098 | 5.15 |
| lymphocyte-specific protein tyrosine kinase | U07236 | 5.13 |
| MCM5 minichromosome maintenance deficient 5, cell division cycle 46 (S. cerevisiae) | NM_006739 | 5.12 |
| homeo box A1 | AC004079 | 5.11 |
| HLA-B associated transcript 3 | NM_004639 | 5.11 |
| tubulin alpha 6 | BC005946 | 5.10 |
| endonuclease G | NM_004435 | 5.10 |
| similar to RIKEN cDNA 2310040G17 gene | BF972185 | 5.09 |
| protein kinase, cAMP-dependent, regulatory, type I, alpha (tissue specific extinguisher 1) | M18468 | 5.09 |
| Consensus includes gb:BG531983 /FEA=EST /DB_XREF=gi:13523521 /DB_XREF=est:602561007F1 /CLONE=IMAGE:4699176 /UG=Hs.108104 ubiquitin-conjugating enzyme E2L 3 /FL=gb:NM_003347.1 | BG531983 | 5.08 |
| protein disulfide isomerase related protein (calcium-binding protein, intestinal-related) | BC000425 | 5.07 |
| proteasome (prosome, macropain) subunit, beta type, 3 | NM_002795 | 5.07 |
| T cell receptor alpha locus | M12423 | 5.06 |

FIG. 4C-10

| Description | Accession | Value |
|---|---|---|
| MCM7 minichromosome maintenance deficient 7 (S. cerevisiae) | D55716 | 5.06 |
| nuclear distribution gene C (A.nidulans) homolog | AF241788 | 5.05 |
| T cell receptor alpha locus | L34703 | 5.04 |
| HLA-B associated transcript 3 | BC003133 | 5.02 |
| ATPase, H+ transporting, lysosomal (vacuolar proton pump), member D | AL566172 | 5.00 |
| actin, gamma 1 | AU145192 | 4.99 |
| kinesin-like 4 | AC002301 | 4.98 |
| karyopherin (importin) beta 3 | NM_002271 | 4.98 |
| translocase of inner mitochondrial membrane 10 homolog (yeast) | NM_012456 | 4.98 |
| baculoviral IAP repeat-containing 5 (survivin) | AB028869 | 4.98 |
| stress-induced-phosphoprotein 1 (Hsp70/Hsp90-organizing protein) | AL553320 | 4.97 |
| ribosomal protein, large, P1 | NM_001003 | 4.97 |
| myosin ID | AA621962 | 4.97 |
| Xq28, 2000bp sequence contg. ORF | BE676218 | 4.96 |
| GDP-mannose pyrophosphorylase A | NM_013335 | 4.96 |
| casein kinase 2, beta polypeptide | NM_001320 | 4.91 |
| proteasome (prosome, macropain) 26S subunit, non-ATPase, 4 | U51007 | 4.90 |
| cullin 1 | NM_003592 | 4.90 |
| Huntingtin interacting protein B | AF049103 | 4.90 |
| HLA-G histocompatibility antigen, class I, G | M90684 | 4.87 |
| solute carrier family 7 (cationic amino acid transporter, y+ system), member 5 | AB018009 | 4.86 |
| manic fringe homolog (Drosophila) | AI738965 | 4.85 |
| RNA-binding protein (autoantigenic) | NM_016732 | 4.85 |
| heat shock 70kD protein 4 | BC002526 | 4.84 |
| SWI/SNF related, matrix associated, actin dependent regulator of chromatin, subfamily f, member 1 | AF231056 | 4.84 |
| leucine rich repeat (in FLII) interacting protein 1 | NM_004735 | 4.83 |
| Rho GDP dissociation inhibitor (GDI) alpha | NM_004309 | 4.83 |
| adaptor-related protein complex 2, sigma 1 subunit | BC006337 | 4.82 |
| lymphotoxin beta (TNF superfamily, member 3) | NM_002341 | 4.81 |
| cytochrome c oxidase subunit Vb | NM_001862 | 4.81 |
| chromosome 11 open reading frame2 | NM_013265 | 4.79 |
| NADH dehydrogenase (ubiquinone) 1 alpha subcomplex, 7 (14.5kD, B14.5a) | NM_005001 | 4.78 |
| KIAA0906 protein | AA502912 | 4.77 |
| splicing factor, arginine/serine-rich 1 (splicing factor 2, alternate splicing factor) | NM_006924 | 4.77 |
| CD37 antigen | NM_001774 | 4.77 |
| tubulin alpha 6 | BC004949 | 4.74 |
| block of proliferation 1 | BG491842 | 4.74 |
| peroxiredoxin 1 | L19184 | 4.73 |
| thymopoietin | AF113682 | 4.72 |
| cyclin-dependent kinase 4 | NM_000075 | 4.71 |
| ribosomal protein L13a | BC001675 | 4.70 |

FIG. 4C-11

| Description | Accession | Value |
|---|---|---|
| T cell receptor alpha locus | M15565 | 4.69 |
| PAI-1 mRNA-binding protein | BC003049 | 4.66 |
| NADH dehydrogenase (ubiquinone) Fe-S protein 8 (23kD) (NADH-coenzyme Q reductase) | NM_002496 | 4.63 |
| ribosomal protein L13a | BF942308 | 4.60 |
| serine palmitoyltransferase, long chain base subunit 2 | U15555 | 4.60 |
| isopentenyl-diphosphate delta isomerase | BC005247 | 4.58 |
| major histocompatibility complex, class II, DM alpha | X76775 | 4.57 |
| flightless I homolog (Drosophila) | AI830227 | 4.57 |
| translocating chain-associating membrane protein | NM_014294 | 4.56 |
| H2A histone family, member X | NM_002105 | 4.55 |
| NADH dehydrogenase (ubiquinone) 1 beta subcomplex, 2 (8kD, AGGG) | NM_004546 | 4.55 |
| transcriptional regulator protein | NM_013260 | 4.53 |
| succinate dehydrogenase complex, subunit B, iron sulfur (Ip) | NM_003000 | 4.52 |
| Sjogren's syndrome/scleroderma autoantigen 1 | NM_006396 | 4.51 |
| RuvB-like 2 (E. coli) | NM_006666 | 4.49 |
| major histocompatibility complex, class II, DQ alpha 1 | BG397856 | 4.48 |
| SH3-domain, GRB2-like, endophilin B2 | NM_020145 | 4.47 |
| hypothetical protein MGC4368 | NM_024510 | 4.47 |
| isopentenyl-diphosphate delta isomerase | NM_004508 | 4.47 |
| ATP synthase, H+ transporting, mitochondrial F1 complex, alpha subunit, isoform 1, cardiac muscle | AI587323 | 4.46 |
| Consensus includes gb:BF695847 /FEA=EST /DB_XREF=gi:11981255 /DB_XREF=est:601852205F1 /CLONE=IMAGE:4076232 /UG=Hs.301917 YDD19 protein | BF695847 | 4.45 |
| Consensus includes gb:X02189 /DEF=H.sapiens adenosine deaminase (ADA) gene 5 flanking region and exon 1 (and joined CDS) /FEA=CDS /DB_XREF=gi:28358 /UG=Hs.1217 adenosine deaminase | X02189 | 4.44 |
| insulin induced gene 1 | BE300521 | 4.41 |
| inhibitor of DNA binding 1, dominant negative helix-loop-helix protein | D13889 | 4.40 |
| eukaryotic translation elongation factor 1 gamma | NM_001404 | 4.40 |
| Consensus includes gb:AJ011414.1 /DEF=Homo sapiens mRNA for plexin-B1 plasma membrane receptor, truncated splice variant (plexin-B1SEP gene). /FEA=mRNA /GEN=plexin-B1SEP /PROD=plexin-B1SEP receptor /DB_XREF=gi:5918164 /UG=Hs.312939 Homo sapiens mRNA for | AJ011414 | 4.40 |
| chromosome condensation-related SMC-associated protein 1 | AK022511 | 4.40 |
| Consensus includes gb:BF530535 /FEA=EST /DB_XREF=gi:11617898 /DB_XREF=est:602071788F1 /CLONE=IMAGE:4214660 /UG=Hs.77665 KIAA0102 gene product /FL=gb:D14658.1 gb:NM_014752.1 | BF530535 | 4.39 |
| fuse-binding protein-interacting repressor | AF217197 | 4.38 |
| mitochondrial carrier homolog 2 | NM_014342 | 4.36 |
| cytochrome c oxidase subunit VIIc | AA382702 | 4.36 |
| v-raf-1 murine leukemia viral oncogene homolog 1 | NM_002880 | 4.36 |

FIG. 4C-12

| | | |
|---|---|---|
| ribosomal protein L13a | NM_012423 | 4.35 |
| potassium channel, subfamily K, member 12 | NM_022055 | 4.35 |
| polypyrimidine tract binding protein (heterogeneous nuclear ribonucleoprotein I) | AA679988 | 4.34 |
| DKFZP586M1523 protein | BF063896 | 4.34 |
| KIAA0618 gene product | N29665 | 4.33 |
| leucine-rich repeat protein, neuronal 1 | AI654857 | 4.33 |
| hypothetical protein FLJ20512 | NM_017854 | 4.32 |
| structure specific recognition protein 1 | NM_003146 | 4.31 |
| valyl-tRNA synthetase 2 | NM_006295 | 4.30 |
| RNA binding motif protein 4 | NM_002896 | 4.30 |
| KIAA0922 protein | AL136932 | 4.30 |
| ribosomal protein, large P2 | NM_001004 | 4.30 |
| Consensus includes gb:AA653300 /FEA=EST /DB_XREF=gi:2589471 /DB_XREF=est:ag65c10.s1 /CLONE=IMAGE:1127826 /UG=Hs.132390 zinc finger protein 36 (KOX 18) | AA653300 | 4.29 |
| NADH dehydrogenase (ubiquinone) 1 alpha subcomplex, 8 (19kD, PGIV) | NM_014222 | 4.27 |
| golgi associated, gamma adaptin ear containing, ARF binding protein 2 | BC000284 | 4.27 |
| phosphoinositide-3-kinase, regulatory subunit, polypeptide 3 (p55, gamma) | BE622627 | 4.26 |
| HS1 binding protein | NM_006118 | 4.26 |
| HSPC003 protein | NM_014017 | 4.25 |
| KIAA0618 gene product | AI768378 | 4.25 |
| dynactin 1 (p150, glued homolog, Drosophila) | NM_004082 | 4.25 |
| cytosolic acyl coenzyme A thioester hydrolase | NM_007274 | 4.25 |
| DnaJ (Hsp40) homolog, subfamily C, member 8 | NM_014280 | 4.23 |
| cold shock domain protein A | NM_003651 | 4.23 |
| CDW52 antigen (CAMPATH-1 antigen) | N90866 | 4.20 |
| hypothetical protein MGC2594 | NM_024050 | 4.20 |
| mitochondrial solute carrier | BE677761 | 4.20 |
| ribonuclease H1 | NM_002936 | 4.19 |
| C2f protein | U72514 | 4.18 |
| adaptor-related protein complex 2, sigma 1 subunit | NM_004069 | 4.18 |
| hypothetical protein FLJ10359 | NM_018072 | 4.17 |
| branched chain aminotransferase 1, cytosolic | NM_005504 | 4.17 |
| FK506 binding protein precursor | NM_016594 | 4.16 |
| Consensus includes gb:AW582267 /FEA=EST /DB_XREF=gi:7257316 /DB_XREF=est:QV0-ST0215-060100-083-c06 /UG=Hs.306951 Human DNA sequence from clone RP11-375F2 on chromosome 1 Contains a pseudogene similar to UBL1 (ubiquitin-like 1 (sentrin)), a pseudogene sim | AW582267 | 4.15 |
| DKFZp434J1813 protein | BG168666 | 4.14 |
| G-2 and S-phase expressed 1 | BF305380 | 4.14 |
| ribosomal protein L27a | NM_000990 | 4.14 |
| neutrophil cytosolic factor 1 (47kD, chronic granulomatous | NM_000265 | 4.13 |

FIG. 4C-13

| Description | Accession | Value |
|---|---|---|
| disease, autosomal 1) | | |
| serum/glucocorticoid regulated kinase-like | NM_013257 | 4.13 |
| FK506 binding protein 1A (12kD) | BC001002 | 4.13 |
| phosphogluconate dehydrogenase | NM_002631 | 4.13 |
| non-POU-domain-containing, octamer-binding | BC003129 | 4.12 |
| RNA binding motif protein 10 | AL137421 | 4.12 |
| aspartyl aminopeptidase | NM_012100 | 4.12 |
| tetraspan 3 | NM_005724 | 4.12 |
| Ewing sarcoma breakpoint region 1 | BC000527 | 4.10 |
| ret finger protein | AF230394 | 4.10 |
| ribonuclease 6 precursor | NM_003730 | 4.09 |
| tumor protein D52 | BG389015 | 4.09 |
| Consensus includes gb:BG537190 /FEA=EST /DB_XREF=gi:13528922 /DB_XREF=est:602565589F1 /CLONE=IMAGE:4690079 /UG=Hs.111334 ferritin, light polypeptide | BG537190 | 4.08 |
| BCL2-interacting killer (apoptosis-inducing) | NM_001197 | 4.08 |
| KIAA0310 gene product | BC001404 | 4.07 |
| accessory proteins BAP31/BAP29 | NM_005745 | 4.06 |
| proteasome (prosome, macropain) 26S subunit, non-ATPase, 9 | NM_002813 | 4.05 |
| neutrophil cytosolic factor 1 (47kD, chronic granulomatous disease, autosomal 1) | AW072388 | 4.05 |
| butyrophilin, subfamily 3, member A2 | BC002832 | 4.04 |
| B-cell associated protein | NM_007273 | 4.03 |
| ATPase, H+ transporting, lysosomal (vacuolar proton pump), beta polypeptide, 56/58kD, isoform 2 | NM_001693 | 4.02 |
| mitochondrial ribosomal protein S7 | NM_015971 | 4.01 |
| major histocompatibility complex, class I, E | NM_005516 | 4.00 |
| mitogen-activated protein kinase kinase 3 | AA780381 | 4.00 |
| KIAA0699 protein | BC002327 | 3.99 |
| protein phosphatase 1, regulatory subunit 7 | NM_002712 | 3.99 |
| KIAA0729 protein | AW502434 | 3.98 |
| thyroid autoantigen 70kD (Ku antigen) | NM_001469 | 3.97 |
| proteasome (prosome, macropain) subunit, beta type, 9 (large multifunctional protease 2) | NM_002800 | 3.97 |
| hypothetical protein MGC5585 | NM_024057 | 3.96 |
| polymerase (RNA) II (DNA directed) polypeptide I (14.5kD) | AL037557 | 3.94 |
| B-cell translocation gene 1, anti-proliferative | AL535380 | 3.94 |
| hypothetical protein FLJ20859 | NM_022734 | 3.93 |
| ATP citrate lyase | U18197 | 3.92 |
| GNAS complex locus | AF064092 | 3.92 |
| gb:M24669.1 /DEF=Human Ig rearranged H-chain V-region mRNA (C-D-JH6), complete cds. /FEA=mRNA /GEN=IGH@ /DB_XREF=gi:185200 /FL=gb:M24669.1 | M24669 | 3.92 |
| major histocompatibility complex, class I, E | M31183 | 3.91 |
| insulin induced gene 1 | NM_005542 | 3.91 |
| Consensus includes gb:AI001784 /FEA=EST | AI001784 | 3.91 |

FIG. 4C-14

| | | |
|---|---|---|
| /DB_XREF=gi:3202255 /DB_XREF=est:ot41g06.s1 /CLONE=IMAGE:1619386 /UG=Hs.308332 ESTs, Highly similar to A42735 ribosomal protein L10, cytosolic H.sapiens Consensus includes gb:Z82202 /DEF=Human DNA sequence from clone RP1-34P24 on chromosome 22 Contains a pseudogene similar to ribosomal protein L35, ESTs, STSs and GSSs /FEA=CDS /DB_XREF=gi:4107193 /UG=Hs.247778 Human DNA sequence from clone RP1-34P24 on c | Z82202 | 3.89 |
| heterogeneous nuclear ribonucleoprotein R | NM_005826 | 3.89 |
| platelet-activating factor acetylhydrolase, isoform Ib, gamma subunit (29kD) | NM_002573 | 3.89 |
| hypothetical protein | BG257762 | 3.89 |
| cytochrome c oxidase subunit Vb | BC006229 | 3.88 |
| DKFZP547E1010 protein | AF261137 | 3.88 |
| interferon regulatory factor 3 | NM_001571 | 3.87 |
| postmeiotic segregation increased 2-like 9 | U38979 | 3.86 |
| putative cyclin G1 interacting protein | NM_006349 | 3.86 |
| GNAS complex locus | NM_000516 | 3.86 |
| cyclin-dependent kinase 5 | NM_004935 | 3.86 |
| hippocalcin-like 1 | NM_002149 | 3.86 |
| 24-dehydrocholesterol reductase | NM_014762 | 3.86 |
| 2',5'-oligoadenylate synthetase 1 (40-46 kD) | NM_002534 | 3.85 |
| DEAD/H (Asp-Glu-Ala-Asp/His) box polypeptide 30 | NM_014966 | 3.85 |
| CREBBP/EP300 inhibitory protein 1 | AF274951 | 3.85 |
| adenylate kinase 2 | U39945 | 3.84 |
| structure specific recognition protein 1 | BE795648 | 3.84 |
| Rho GDP dissociation inhibitor (GDI) alpha | BC005851 | 3.84 |
| Consensus includes gb:X04802 /DEF=Homo sapiens UBBP2 pseudogene for ubiquitin UBB /FEA=CDS /DB_XREF=gi:37582 /UG=Hs.247890 Homo sapiens UBBP2 pseudogene for ubiquitin UBB | X04802 | 3.84 |
| ubiquitin-conjugating enzyme E2M (UBC12 homolog, yeast) | NM_003969 | 3.83 |
| adenosine deaminase | NM_000022 | 3.83 |
| kinesin 2 (60-70kD) | AA284075 | 3.82 |
| eukaryotic translation initiation factor 2, subunit 3 (gamma, 52kD) | NM_001415 | 3.82 |
| hypothetical protein PRO1847 | AF119855 | 3.82 |
| enhancer of invasion 10 | NM_021178 | 3.82 |
| MCM2 minichromosome maintenance deficient 2, mitotin (S. cerevisiae) | NM_004526 | 3.81 |
| CDC37 cell division cycle 37 homolog (S. cerevisiae) | U63131 | 3.81 |
| WD repeat domain 1 | AB010427 | 3.81 |
| A kinase (PRKA) anchor protein 2 | BE879367 | 3.81 |
| neural precursor cell expressed, developmentally down-regulated 8 | NM_006156 | 3.80 |
| olfactory receptor, family 1, subfamily K, member 1 | NM_018835 | 3.80 |
| GNAS complex locus | AF088184 | 3.79 |
| translocase of inner mitochondrial membrane 23 homolog (yeast) | NM_006327 | 3.79 |
| O-6-methylguanine-DNA methyltransferase | NM_002412 | 3.79 |

FIG. 4C-15

| | | |
|---|---|---|
| eukaryotic translation elongation factor 1 alpha 1 | NM_001402 | 3.79 |
| H3 histone, family 3B (H3.3B) | NM_005324 | 3.79 |
| KIAA0974 protein | BE551340 | 3.78 |
| S-adenosylmethionine decarboxylase 1 | M21154 | 3.77 |
| hypothetical protein MGC:5244, | NM_031213 | 3.76 |
| nucleotide binding protein 2 (MinD homolog, E. coli) | NM_012225 | 3.75 |
| cut-like 1, CCAAT displacement protein (Drosophila) | NM_001913 | 3.75 |
| splicing factor 3a, subunit 3, 60kD | NM_006802 | 3.75 |
| ribosomal protein S18 | NM_022551 | 3.74 |
| zinc finger protein 259 | NM_003904 | 3.74 |
| paired immunoglobulin-like receptor beta | NM_013440 | 3.73 |
| serine/threonine kinase 15 | NM_003600 | 3.73 |
| chromosome 20 open reading frame 1 | AF098158 | 3.73 |
| SH3 domain binding glutamic acid-rich protein like 3 | NM_031286 | 3.72 |
| cyclin G2 | L49506 | 3.72 |
| ARP2 actin-related protein 2 homolog (yeast) | NM_005722 | 3.71 |
| ubiquitin specific protease 7 (herpes virus-associated) | NM_003470 | 3.69 |
| deoxyhypusine synthase | NM_001930 | 3.69 |
| serologically defined colon cancer antigen 16 | BC001149 | 3.69 |
| ribosomal protein L10 | AL031276 | 3.68 |
| PRKC, apoptosis, WT1, regulator | AI336206 | 3.68 |
| hydroxyacyl-Coenzyme A dehydrogenase/3-ketoacyl-Coenzyme A thiolase/enoyl-Coenzyme A hydratase (trifunctional protein), alpha subunit | U04627 | 3.67 |
| gb:Z25433.1 /DEF=H.sapiens protein-serinethreonine kinase gene, complete CDS. /FEA=mRNA /PROD=protein-serinethreonine kinase /DB_XREF=gi:405744 /FL=gb:Z25433.1 | Z25433 | 3.66 |
| NRAS-related gene | AA167775 | 3.66 |
| mesenchymal stem cell protein DSC92 | NM_016645 | 3.65 |
| SRY (sex determining region Y)-box 2 | AW007161 | 3.65 |
| chromatin-specific transcription elongation factor, 140 kDa subunit | NM_007192 | 3.65 |
| uncoupling protein 2 (mitochondrial, proton carrier) | U82819 | 3.64 |
| kinesin-like 6 (mitotic centromere-associated kinesin) | AY026505 | 3.63 |
| lymphoid-restricted membrane protein | NM_006152 | 3.63 |
| T-cell leukemia/lymphoma 1A | BC003574 | 3.63 |
| ATPase, H+ transporting, lysosomal (vacuolar proton pump) 42kD | NM_001695 | 3.63 |
| chromatin assembly factor 1, subunit A (p150) | NM_005483 | 3.61 |
| proteasome (prosome, macropain) activator subunit 3 (PA28 gamma; Ki) | NM_005789 | 3.60 |
| KIAA1007 protein | BC000779 | 3.60 |
| glia maturation factor, gamma | NM_004877 | 3.59 |
| POP7 (processing of precursor, S. cerevisiae) homolog | BC001430 | 3.59 |
| Breakpoint cluster region protein, uterine leiomyoma, 1; barrier to autointegration factor | AF044773 | 3.59 |
| ubiquitin-like 5 | NM_024292 | 3.59 |
| hypothetical protein AF140225 | NM_030799 | 3.58 |
| NBR2 | BC000924 | 3.58 |

FIG. 4C-16

| | | |
|---|---|---|
| deoxyhypusine synthase | U26266 | 3.58 |
| peroxiredoxin 2 | NM_005809 | 3.58 |
| Consensus includes gb:BE731738 /FEA=EST /DB_XREF=gi:10145730 /DB_XREF=est:601568154F1 /CLONE=IMAGE:3842844 /UG=Hs.182937 peptidylprolyl isomerase A (cyclophilin A) | BE731738 | 3.58 |
| sperm associated antigen 9 | NM_003971 | 3.57 |
| MCM4 minichromosome maintenance deficient 4 (S. cerevisiae) | AI859865 | 3.57 |
| laminin receptor 1 (67kD, ribosomal protein SA) | AL136306 | 3.57 |
| villin 2 (ezrin) | AA670344 | 3.57 |
| zinc finger protein | NM_015871 | 3.57 |

FIG. 4D-1

| Gene | NCBI Accession Number | FOLD DECREASE |
|---|---|---|
| ribosomal protein S11 | BF680255 | 22.06 |
| ribosomal protein, large P2 | BC005354 | 15.91 |
| Consensus includes gb:AJ249377.1 /DEF=Homo sapiens partial mRNA for human Ig lambda light chain variable region, clone MB91 (331 bp). /FEA=mRNA /GEN=IGLV /PROD=immunoglobulin lambda variable region /DB_XREF=gi:5911837 /UG=Hs.247898 Human anti-streptococ | AJ249377 | 15.77 |
| calreticulin | AI378706 | 14.14 |
| ribosomal protein S19 | BC000023 | 14.00 |
| Consensus includes gb:D84143.1 /DEF=Human immunoglobulin (mAb59) light chain V region mRNA, partial sequence. /FEA=mRNA /PROD=immunoglobulin light chain V-J region /DB_XREF=gi:1255613 /UG=Hs.121508 Human immunoglobulin (mAb59) light chain V region mRNA, | D84143 | 13.82 |
| Consensus includes gb:AA292281 /FEA=EST /DB_XREF=gi:1940261 /DB_XREF=est:zt51b03.s1 /CLONE=IMAGE:725837 /UG=Hs.181307 H3 histone, family 3A | AA292281 | 13.65 |
| ribosomal protein L27a | BE737027 | 13.26 |
| Consensus includes gb:AW302047 /FEA=EST /DB_XREF=gi:6711724 /DB_XREF=est:xr52f08.x1 /CLONE=IMAGE:2763783 /UG=Hs.76230 ribosomal protein S10 | AW302047 | 13.16 |
| ribosomal protein S20 | AF113008 | 10.69 |
| Consensus includes gb:L48784 /DEF=050 Homo sapiens cDNA /FEA=mRNA /DB_XREF=gi:1066715 /UG=Hs.182426 ribosomal protein S2 | L48784 | 8.01 |
| J04423 E coli bioB gene biotin synthetase (-5, -M, -3 represent transcript regions 5 prime, Middle, and 3 prime respectively) | J04423 | 6.76 |
| calreticulin | AA910371 | 6.64 |
| Escherichia coli /REF=J04423 /DEF=E coli bioB gene biotin synthetase corresponding to nucleotides 2393-2682 of J04423 /LEN=1114 (-5, -M, -3 represent transcript regions 5 prime, Middle, and 3 prime respectively) | J04423 | 6.36 |
| Cluster Incl. AI201594:qc02h12.x1 Homo sapiens cDNA, 3 end /clone=IMAGE-1708487 /clone_end=3 /gb=AI201594 /gi=3754200 /ug=Hs.239333 /len=591 | AI201594 | 6.20 |
| ribosomal protein L27 | BE312027 | 5.96 |
| ribosomal protein L37a | BE857772 | 5.88 |
| J04423 E coli bioB gene biotin synthetase (-5, -M, -3 represent transcript regions 5 prime, Middle, and 3 prime respectively) | J04423 | 5.80 |
| Escherichia coli /REF=J04423 /DEF=E coli bioB gene biotin synthetase corresponding to nucleotides 2071-2304 of J04423 /LEN=1114 (-5, -M, -3 represent transcript regions 5 prime, Middle, and 3 prime respectively) | J04423 | 5.77 |

FIG. 4D-2

| Description | Accession | Value |
|---|---|---|
| Escherichia coli /REF=J04423 /DEF=E coli bioB gene biotin synthetase corresponding to nucleotides 2772-3004 of J04423 /LEN=1114 (-5, -M, -3 represent transcript regions 5 prime, Middle, and 3 prime respectively) | J04423 | 5.72 |
| J04423 E coli bioB gene biotin synthetase (-5, -M, -3 represent transcript regions 5 prime, Middle, and 3 prime respectively) | J04423 | 5.57 |
| immunoglobulin lambda locus | AF043586 | 5.53 |
| J04423 E coli bioC protein (-5 and -3 represent transcript regions 5 prime and 3 prime respectively) | J04423 | 5.35 |
| ribosomal protein L38 | AW303136 | 4.99 |
| Consensus includes gb:AJ239383.1 /DEF=Homo sapiens mRNA for immunoglobulin heavy chain variable region, ID 31. /FEA=mRNA /GEN=IGHV /PROD=immunoglobulin heavy chain variable region /DB_XREF=gi:4456587 /UG=Hs.249245 Homo sapiens mRNA for single-chain anti | AJ239383 | 4.96 |
| Consensus includes gb:AI345238 /FEA=EST /DB_XREF=gi:4082444 /DB_XREF=est:tb81b07.x1 /CLONE=IMAGE:2060725 /UG=Hs.111334 ferritin, light polypeptide | AI345238 | 4.95 |
| Escherichia coli /REF=J04423 /DEF=E coli bioC protein corresponding to nucleotides 4257-4573 of J04423 /LEN=777 (-5 and -3 represent transcript regions 5 prime and 3 prime respectively) | J04423 | 4.76 |
| hypothetical protein FLJ21034 | NM_024940 | 4.69 |
| Escherichia coli /REF=J04423 /DEF=E coli bioC protein corresponding to nucleotides 4609-4883 of J04423 /LEN=777 (-5 and -3 represent transcript regions 5 prime and 3 prime respectively) | J04423 | 4.64 |
| ribosomal protein L38 | BC000603 | 4.47 |
| killer cell immunoglobulin-like receptor, three domains, long cytoplasmic tail, 2 | X93596 | 4.39 |
| PTPRF interacting protein, binding protein 1 (liprin beta 1) | N35896 | 4.31 |
| hypothetical protein FLJ12619 | BE465032 | 4.30 |
| C-terminal binding protein 1 | BF984434 | 4.29 |
| Consensus includes gb:BF942161 /FEA=EST /DB_XREF=gi:12359481 /DB_XREF=est:nae87g10.x1 /CLONE=IMAGE:4118994 /UG=Hs.302797 ESTs | BF942161 | 4.27 |
| Consensus includes gb:AF044592 /DEF=Homo sapiens lymphocyte-predominant Hodgkins disease case 4 immunoglobulin heavy chain gene, variable region, partial cds /FEA=CDS /DB_XREF=gi:2852420 /UG=Hs.248077 Homo sapiens lymphocyte-predominant Hodgkins disease | AF044592 | 4.24 |
| hypothetical protein FLJ12985 | NM_024924 | 4.24 |
| thiopurine S-methyltransferase | U12387 | 4.22 |
| J04423 E coli bioD gene dethiobiotin synthetase (-5 and -3 represent transcript regions 5 prime and 3 prime respectively) | J04423 | 4.19 |
| J04423 E coli bioC protein (-5 and -3 represent transcript regions 5 prime and 3 prime respectively) | J04423 | 4.17 |
| Consensus includes gb:AL050122.1 /DEF=Homo sapiens mRNA; cDNA DKFZp586E121 (from clone DKFZp586E121). /FEA=mRNA /DB_XREF=gi:4884330 /UG=Hs.274511 Homo sapiens mRNA; | AL050122 | 4.11 |

FIG. 4D-3

| | | |
|---|---|---|
| cDNA DKFZp586E121 (from clone DKFZp586E121) Consensus includes gb:AW301806 /FEA=EST /DB_XREF=gi:6711483 /DB_XREF=est:xr56e11.x1 /CLONE=IMAGE:2764172 /UG=Hs.150551 ESTs, Weakly similar to ALU1_HUMAN ALU SUBFAMILY J SEQUENCE CONTAMINATION WARNING ENTRY H.sapiens | AW301806 | 4.10 |
| thromboxane A2 receptor | NM_001060 | 4.08 |
| ADP-ribosylation factor 6 | AA243143 | 4.02 |
| PCTAIRE protein kinase 1 | NM_006201 | 3.95 |
| JTV1 gene | AF116615 | 3.90 |
| hypothetical protein PRO1843 | NM_018507 | 3.86 |
| dystrophia myotonica-containing WD repeat motif | L19267 | 3.79 |
| emopamil binding protein (sterol isomerase) | N58493 | 3.78 |
| Escherichia coli /REF=J04423 /DEF=E coli bioD gene dethiobiotin synthetase corresponding to nucleotides 5312-5559 of J04423 /LEN=676 (-5 and -3 represent transcript regions 5 prime and 3 prime respectively) | J04423 | 3.77 |
| Escherichia coli /REF=J04423 /DEF=E coli bioD gene dethiobiotin synthetase corresponding to nucleotides 5024-5244 of J04423 /LEN=676 (-5 and -3 represent transcript regions 5 prime and 3 prime respectively) | J04423 | 3.74 |
| gb:AF090895.1 /DEF=Homo sapiens clone HQ0117 PRO0117 mRNA, complete cds. /FEA=mRNA /PROD=PRO0117 /DB_XREF=gi:6690166 /UG=Hs.283919 Homo sapiens clone HQ0117 PRO0117 mRNA, complete cds /FL=gb:AF090895.1 | AF090895 | 3.71 |
| GM2 ganglioside activator protein | X61094 | 3.70 |
| putative protein O-mannosyltransferase | NM_013382 | 3.69 |
| Consensus includes gb:BF973387 /FEA=EST /DB_XREF=gi:12340602 /DB_XREF=est:602242353F1 /CLONE=IMAGE:4330861 /UG=Hs.305989 Human DNA sequence from clone RP3-483K16 on chromosome 6p12.1-21.1. Contains (parts of) two novel genes, RPS16 (40S Ribosomal protein | BF973387 | 3.69 |
| M10098 Human 18S rRNA sequence, length 1969 bases, middle target bases 647-1292 | M10098 | 3.69 |
| aminopeptidase puromycin sensitive | BG153399 | 3.65 |
| gb:Z25437.1 /DEF=H.sapiens protein-tyrosine kinase gene, complete CDS. /FEA=mRNA /PROD=protein-tyrosine kinase /DB_XREF=gi:405752 /FL=gb:Z25437.1 | Z25437 | 3.63 |
| Consensus includes gb:AK026825.1 /DEF=Homo sapiens cDNA: FLJ23172 fis, clone LNG10005. /FEA=mRNA /DB_XREF=gi:10439771 /UG=Hs.306885 Homo sapiens cDNA: FLJ23172 fis, clone LNG10005 | AK026825 | 3.63 |
| ubiquitously transcribed tetratricopeptide repeat gene, Y chromosome | NM_007125 | 3.61 |
| Consensus includes gb:AI732770 /FEA=EST /DB_XREF=gi:5053883 /DB_XREF=est:zx78d05.x5 /CLONE=IMAGE:809865 /UG=Hs.328688 ESTs, Moderately similar to ALU7_HUMAN ALU SUBFAMILY SQ SEQUENCE CONTAMINATION WARNING ENTRY H.sapiens | AI732770 | 3.57 |

FIG. 4D-4

| Description | Accession | Value |
|---|---|---|
| acidic epididymal glycoprotein-like 1 | X95238 | 3.55 |
| hypothetical protein FLJ10357 | NM_018071 | 3.51 |
| J04423 E coli bioD gene dethiobiotin synthetase (-5 and -3 represent transcript regions 5 prime and 3 prime respectively) | J04423 | 3.48 |
| Consensus includes gb:AV719355 /FEA=EST /DB_XREF=gi:10816507 /DB_XREF=est:AV719355 /CLONE=GLCEMB06 /UG=Hs.97109 ESTs. | AV719355 | 3.44 |
| KIAA1655 protein | AB051442 | 3.41 |
| Consensus includes gb:AA890010 /FEA=EST /DB_XREF=gi:3016889 /DB_XREF=est:aj89h08.s1 /CLONE=IMAGE:1403679 /UG=Hs.50785 SEC22, vesicle trafficking protein (S. cerevisiae)-like 1 | AA890010 | 3.41 |
| hypothetical protein FLJ21603 | NM_024762 | 3.41 |
| protein kinase, interferon-inducible double stranded RNA dependent | NM_002759 | 3.40 |
| hypothetical protein FLJ10298 | NM_018050 | 3.40 |
| translation initiation factor IF2 | AB018284 | 3.39 |
| collagen, type I, alpha 1 | AI743621 | 3.39 |
| alanine-glyoxylate aminotransferase 2-like 1 | NM_031279 | 3.37 |
| PRO0478 protein | NM_014129 | 3.36 |
| Consensus includes gb:AW971134 /FEA=EST /DB_XREF=gi:8160979 /DB_XREF=est:EST383221 /UG=Hs.292245 ESTs, Weakly similar to ALU1_HUMAN ALU SUBFAMILY J SEQUENCE CONTAMINATION WARNING ENTRY H.sapiens | AW971134 | 3.32 |
| sialophorin (gpL115, leukosialin, CD43) | NM_003123 | 3.31 |
| islet cell autoantigen 1 (69kD) | BC005922 | 3.30 |
| ATPase, H+ transporting, lysosomal (vacuolar proton pump) non-catalytic accessory protein 1A (110/116kD) | NM_005177 | 3.30 |
| protein phosphatase 2 (formerly 2A), regulatory subunit B" (PR 72), alpha isoform and (PR 130), beta isoform | AI760130 | 3.29 |
| HIV-1 rev binding protein 2 | AI912583 | 3.28 |
| sorting nexin 4 | AA524345 | 3.26 |
| aldehyde dehydrogenase 1 family, member B1 | BC001619 | 3.26 |
| Consensus includes gb:AW971415 /FEA=EST /DB_XREF=gi:8161260 /DB_XREF=est:EST383504 /UG=Hs.165337 ESTs | AW971415 | 3.25 |
| Consensus includes gb:AK026484.1 /DEF=Homo sapiens cDNA: FLJ22831 fis, clone KAIA4161. /FEA=mRNA /DB_XREF=gi:10439356 /UG=Hs.321666 Homo sapiens cDNA: FLJ22831 fis, clone KAIA4161 | AK026484 | 3.25 |
| G protein-coupled receptor 37 (endothelin receptor type B-like) | T16257 | 3.24 |
| hypothetical protein FLJ14107 | NM_025026 | 3.22 |
| endomucin-1 | NM_016241 | 3.22 |
| pregnancy specific beta-1-glycoprotein 11 | NM_002785 | 3.22 |
| tyrosine 3-monooxygenase/tryptophan 5-monooxygenase activation protein, epsilon polypeptide | AA502643 | 3.21 |
| Consensus includes gb:AI701156 /FEA=EST /DB_XREF=gi:4989056 /DB_XREF=est:we10f09.x1 | AI701156 | 3.20 |

FIG. 4D-5

| Description | Accession | Value |
|---|---|---|
| /CLONE=IMAGE:2340713 /UG=Hs.6580 Homo sapiens cDNA: FLJ23227 fis, clone CAE00645, highly similar to AF052138 Homo sapiens clone 23718 mRNA sequence Consensus includes gb:AK022473.1 /DEF=Homo sapiens cDNA FLJ12411 fis, clone MAMMA1002964. /FEA=mRNA /DB_XREF=gi:10433882 /UG=Hs.296722 Homo sapiens cDNA FLJ12411 fis, clone MAMMA1002964 | AK022473 | 3.18 |
| CDC5 cell division cycle 5-like (S. pombe) | AB007892 | 3.17 |
| Consensus includes gb:BF573849 /FEA=EST /DB_XREF=gi:11647561 /DB_XREF=est:602132053F1 /CLONE=IMAGE:4271340 /UG=Hs.96343 ESTs, Weakly similar to ALUC_HUMAN !!!! ALU CLASS C WARNING ENTRY !!! H.sapiens | BF573849 | 3.17 |
| harakiri, BCL2 interacting protein (contains only BH3 domain) | U76376 | 3.17 |
| cytochrome P450 isoform 4F12 | NM_023944 | 3.17 |
| gb:BC006361.1 /DEF=Homo sapiens, clone MGC:13137, mRNA, complete cds. /FEA=mRNA /PROD=Unknown (protein for MGC:13137) /DB_XREF=gi:13623508 /FL=gb:BC006361.1 | BC006361 | 3.16 |
| hypothetical protein FLJ22965 | NM_022101 | 3.15 |
| Consensus includes gb:AF222691.1 /DEF=Homo sapiens Alu repeat (LNX1) mRNA sequence. /FEA=mRNA /DB_XREF=gi:12655850 /UG=Hs.307008 Homo sapiens Alu repeat (LNX1) mRNA sequence | AF222691 | 3.15 |
| clone FLB3816 | NM_016415 | 3.15 |
| Consensus includes gb:AI524687 /FEA=EST /DB_XREF=gi:4438822 /DB_XREF=est:th12a07.x1 /CLONE=IMAGE:2118036 /UG=Hs.57969 phenylalanine-tRNA synthetase | AI524687 | 3.14 |
| hypothetical protein FLJ20897 | AI335509 | 3.12 |
| PI-3-kinase-related kinase SMG-1 | BE000837 | 3.11 |
| Consensus includes gb:AI683552 /FEA=EST /DB_XREF=gi:4893734 /DB_XREF=est:tx67h02.x1 /CLONE=IMAGE:2274675 /UG=Hs.201605 ESTs, Moderately similar to ALU8_HUMAN ALU SUBFAMILY SX SEQUENCE CONTAMINATION WARNING ENTRY H.sapiens | AI683552 | 3.08 |
| KIAA0729 protein | AK023845 | 3.07 |
| KIAA1827 protein | AW474158 | 3.07 |
| C-type (calcium dependent, carbohydrate-recognition domain) lectin, superfamily member 6 | AF200738 | 3.04 |
| SCAN domain-containing 2 | AF244812 | 3.03 |
| thyroid hormone receptor-associated protein, 95-kD subunit | BG339606 | 3.02 |
| Consensus includes gb:AK024108.1 /DEF=Homo sapiens cDNA FLJ14046 fis, clone HEMBA1006461. /FEA=mRNA /DB_XREF=gi:10436406 /UG=Hs.142677 Homo sapiens cDNA FLJ14046 fis, clone HEMBA1006461 | AK024108 | 3.02 |
| tumor necrosis factor alpha-inducible cellular protein containing leucine zipper domains; Huntingtin interacting protein L; transcrption factor IIIA-interacting protein | NM_021980 | 3.02 |
| Consensus includes gb:BG290532 /FEA=EST /DB_XREF=gi:13047560 /DB_XREF=est:602388395F1 | BG290532 | 3.01 |

FIG. 4D-6

| | | |
|---|---|---|
| /CLONE=IMAGE:4517206 /UG=Hs.11210 ESTs, Moderately similar to Z137_HUMAN ZINC FINGER PROTEIN 13 H.sapiens mitochondrial ribosomal protein S12 | R68573 | 3.00 |
| P3ECSL | NM_022164 | 2.99 |
| lymphoid blast crisis oncogene | AF127481 | 2.99 |
| KIAA0653 protein, B7-like protein | AF289028 | 2.99 |
| Consensus includes gb:AF035317.1 /DEF=Homo sapiens clone 23892 mRNA sequence. /FEA=mRNA /DB_XREF=gi:2661080 /UG=Hs.91916 Homo sapiens clone 23892 mRNA sequence | AF035317 | 2.99 |
| early lymphoid activation protein | L22650 | 2.98 |
| lipopolysaccharide specific response-68 protein | NM_018678 | 2.97 |
| tissue factor pathway inhibitor (lipoprotein-associated coagulation inhibitor) | J03225 | 2.96 |
| Consensus includes gb:AI734156 /FEA=EST /DB_XREF=gi:5055269 /DB_XREF=est:nc79d04.y5 /CLONE=IMAGE:783559 /UG=Hs.172895 ESTs | AI734156 | 2.96 |
| Consensus includes gb:AW301937 /FEA=EST /DB_XREF=gi:6711614 /DB_XREF=est:xr85b03.x1 /CLONE=IMAGE:2766893 /UG=Hs.138036 ESTs | AW301937 | 2.95 |
| immunoglobulin heavy constant mu | S55735 | 2.93 |
| Consensus includes gb:X78262.1 /DEF=H.sapiens mRNA for TRE5. /FEA=mRNA /DB_XREF=gi:587440 /UG=Hs.302178 H.sapiens mRNA for TRE5 | X78262 | 2.92 |
| Consensus includes gb:R06655 /FEA=EST /DB_XREF=gi:757275 /DB_XREF=est:yf10e02.r1 /CLONE=IMAGE:126458 /UG=Hs.188518 ESTs, Moderately similar to AF078844 1 hqp0376 protein H.sapiens | R06655 | 2.91 |
| somatostatin receptor 4 | NM_001052 | 2.91 |
| Consensus includes gb:AL163202 /DEF=Homo sapiens chromosome 21 segment HS21C002 /FEA=CDS /DB_XREF=gi:7717242 /UG=Hs.289121 Homo sapiens chromosome 21 segment HS21C002 | AL163202 | 2.91 |
| guanine nucleotide exchange factor for Rap1; M-Ras-regulated GEF | AI263837 | 2.90 |
| hypothetical protein PRO0082 | NM_018590 | 2.89 |
| cathepsin S | BC002642 | 2.88 |
| transducin (beta)-like 1 | AA724134 | 2.88 |
| Consensus includes gb:AK022303.1 /DEF=Homo sapiens cDNA FLJ12241 fis, clone MAMMA1001274. /FEA=mRNA /DB_XREF=gi:10433670 /UG=Hs.287503 Homo sapiens cDNA FLJ12241 fis, clone MAMMA1001274 | AK022303 | 2.87 |
| MAD, mothers against decapentaplegic homolog (Drosophila) interacting protein, receptor activation anchor | NM_007323 | 2.87 |
| Consensus includes gb:AL050065.1 /DEF=Homo sapiens mRNA; cDNA DKFZp566M043 (from clone DKFZp566M043). /FEA=mRNA /DB_XREF=gi:4884295 /UG=Hs.212587 Homo sapiens mRNA; cDNA DKFZp566M043 (from clone DKFZp566M043) | AL050065 | 2.86 |
| E74-like factor 4 (ets domain transcription factor) | NM_001421 | 2.85 |
| hypothetical protein 384D8_6 | BC000473 | 2.84 |

FIG. 4D-7

| | | |
|---|---|---|
| phosphodiesterase 10A | AF127480 | 2.84 |
| PABP-interacting protein 2 | AL043487 | 2.84 |
| PRO1880 protein | NM_014104 | 2.83 |
| serine protease inhibitor-like, with Kunitz and WAP domains 1 (eppin) | NM_020398 | 2.82 |
| zinc finger protein 43 (HTF6) | AK022905 | 2.82 |
| solute carrier family 4, sodium bicarbonate cotransporter, member 4 | AF011390 | 2.82 |
| rab3 GTPase-activating protein, non-catalytic subunit (150kD) | AK021928 | 2.81 |
| carboxypeptidase N, polypeptide 2, 83kD | J05158 | 2.79 |
| hypothetical protein FLJ12151 | AK022213 | 2.79 |
| neuronal thread protein | NM_014486 | 2.78 |
| Consensus includes gb:AK021505.1 /DEF=Homo sapiens cDNA FLJ11443 fis, clone HEMBA1001330. /FEA=mRNA /DB_XREF=gi:10432701 /UG=Hs.297945 Homo sapiens cDNA FLJ11443 fis, clone HEMBA1001330 | AK021505 | 2.78 |
| KIAA0889 protein | NM_015377 | 2.78 |
| coactivator-associated arginine methyltransferase-1 | AL529396 | 2.77 |
| ribonuclease P, 40kD subunit | NM_006638 | 2.76 |
| solute carrier family 21 (organic anion transporter), member 6 | AB026257 | 2.75 |
| putative N6-DNA-methyltransferase | NM_013240 | 2.75 |
| Consensus includes gb:AL080160.1 /DEF=Homo sapiens mRNA; cDNA DKFZp434M054 (from clone DKFZp434M054). /FEA=mRNA /DB_XREF=gi:5262622 /UG=Hs.274517 Homo sapiens mRNA; cDNA DKFZp434M054 (from clone DKFZp434M054) | AL080160 | 2.74 |
| dihydrolipoamide branched chain transacylase (E2 component of branched chain keto acid dehydrogenase complex; maple syrup urine disease) | NM_001918 | 2.73 |
| transforming, acidic coiled-coil containing protein 2 | AF220152 | 2.73 |
| prostate derived STE20-like kinase PSK | NM_016151 | 2.73 |
| Consensus includes gb:AL157484.1 /DEF=Homo sapiens mRNA; cDNA DKFZp762M127 (from clone DKFZp762M127). /FEA=mRNA /DB_XREF=gi:7018527 /UG=Hs.22483 Homo sapiens mRNA; cDNA DKFZp762M127 (from clone DKFZp762M127) | AL157484 | 2.73 |
| dynamin 2 | AK023207 | 2.73 |
| sema domain, immunoglobulin domain (Ig), short basic domain, secreted, (semaphorin) 3A | NM_006080 | 2.72 |
| G protein-coupled receptor kinase 6 | BG423052 | 2.72 |
| S100 calcium binding protein A11 (calgizzarin) | NM_005620 | 2.72 |
| cytochrome c oxidase subunit Vb | AI557312 | 2.72 |
| Epstein-Barr virus induced gene 3 | NM_005755 | 2.71 |
| Consensus includes gb:AW974816 /FEA=EST /DB_XREF=gi:8166019 /DB_XREF=est:EST386921 /UG=Hs.283517 ESTs, Weakly similar to ALU1_HUMAN ALU SUBFAMILY J SEQUENCE CONTAMINATION WARNING ENTRY H.sapiens | AW974816 | 2.71 |
| bone morphogenetic protein receptor, type IB | D89675 | 2.71 |

FIG. 4D-8

| | | |
|---|---|---|
| prefoldin 4 | NM_002623 | 2.70 |
| hypothetical protein FLJ21032 | NM_024906 | 2.70 |
| glioma pathogenesis-related protein | U16307 | 2.70 |
| epithelial membrane protein 3 | NM_001425 | 2.69 |
| Consensus includes gb:AK024958.1 /DEF=Homo sapiens cDNA: FLJ21305 fis, clone COL02124. /FEA=mRNA /DB_XREF=gi:10437382 /UG=Hs.287658 Homo sapiens cDNA: FLJ21305 fis, clone COL02124 | AK024958 | 2.69 |
| KRAB zinc finger protein KR18 | AK024789 | 2.69 |
| putatative 28 kDa protein | AF349314 | 2.68 |
| apolipoprotein L, 2 | BC004395 | 2.68 |
| Consensus includes gb:AL110201.1 /DEF=Homo sapiens mRNA; cDNA DKFZp586F1622 (from clone DKFZp586F1622). /FEA=mRNA /DB_XREF=gi:5817120 /UG=Hs.278435 Homo sapiens mRNA; cDNA DKFZp586F1622 (from clone DKFZp586F1622) | AL110201 | 2.67 |
| Consensus includes gb:R33964 /FEA=EST /DB_XREF=gi:789822 /DB_XREF=est:yh74c03.r1 /CLONE=IMAGE:135460 /UG=Hs.288681 Homo sapiens cDNA FLJ11022 fis, clone PLACE1003771 | R33964 | 2.67 |
| Consensus includes gb:AL137378.1 /DEF=Homo sapiens mRNA; cDNA DKFZp434K1126 (from clone DKFZp434K1126). /FEA=mRNA /DB_XREF=gi:6807908 /UG=Hs.306455 Homo sapiens mRNA; cDNA DKFZp434K1126 (from clone DKFZp434K1126) | AL137378 | 2.67 |
| translation initiation factor IF2 | BG261322 | 2.67 |
| KIAA1045 protein | AB028968 | 2.66 |
| hypothetical protein | NM_019069 | 2.66 |
| hypothetical protein FLJ23185 | NM_025056 | 2.66 |
| gamma-aminobutyric acid (GABA) A receptor, alpha 5 | BF966183 | 2.66 |
| colony stimulating factor 2 receptor, alpha, low-affinity (granulocyte-macrophage) | L29349 | 2.66 |
| N-myristoyltransferase 2 | NM_004808 | 2.64 |
| JM27 protein | NM_007003 | 2.64 |
| Consensus includes gb:AK023911.1 /DEF=Homo sapiens cDNA FLJ13849 fis, clone THYRO1000865. /FEA=mRNA /DB_XREF=gi:10435992 /UG=Hs.181810 Homo sapiens cDNA FLJ13849 fis, clone THYRO1000865 | AK023911 | 2.63 |
| immunoglobulin heavy constant mu | S74639 | 2.63 |
| gb:NM_024305.1 /DEF=Homo sapiens hypothetical protein MGC4278 (MGC4278), mRNA. /FEA=mRNA /GEN=MGC4278 /PROD=hypothetical protein MGC4278 /DB_XREF=gi:13236535 /UG=Hs.318780 hypothetical protein MGC4278 /FL=gb:BC002659.1 gb:NM_024305.1 | NM_024305 | 2.63 |
| hypothetical protein MGC2474 | NM_023931 | 2.62 |
| hypothetical protein FLJ21477 | NM_025153 | 2.62 |
| polymerase (DNA directed), eta | NM_006502 | 2.62 |
| Consensus includes gb:AI126492 /FEA=EST /DB_XREF=gi:3595006 /DB_XREF=est:qd82h06.x1 /CLONE=IMAGE:1736027 /UG=Hs.104258 Homo sapiens mRNA, | AI126492 | 2.62 |

FIG. 4D-9

| | | |
|---|---|---|
| exon 1, 2, 3, 4, clone:RES4-24A Consensus includes gb:BC005365.1 /DEF=Homo sapiens, clone IMAGE:3829438, mRNA, partial cds. /FEA=mRNA /PROD=Unknown (protein for IMAGE:3829438) /DB_XREF=gi:13529199 /UG=Hs.331237 Homo sapiens, clone IMAGE:3829438, mRNA, partial cds | BC005365 | 2.61 |
| polymerase (RNA) II (DNA directed) polypeptide B (140kD) | AW770896 | 2.61 |
| cAMP responsive element binding protein-like 1 | U52696 | 2.61 |
| neuropeptide Y receptor Y6 (pseudogene) | U59431 | 2.60 |
| hexokinase 2 | AI761561 | 2.60 |
| Cluster Incl. AI949010:wq36a07.x1 Homo sapiens cDNA, 3 end /clone=IMAGE-2473332 /clone_end=3 /gb=AI949010 /gi=5741320 /ug=Hs.104036 /len=457 | AI949010 | 2.59 |
| mannan-binding lectin serine protease 1 (C4/C2 activating component of Ra-reactive factor) | BC000587 | 2.59 |
| SH3-domain GRB2-like 3 | AF036269 | 2.59 |
| thyroid hormone receptor interactor 11 | BC002656 | 2.59 |
| hypothetical protein PRO2849 | NM_022335 | 2.58 |
| decay accelerating factor for complement (CD55, Cromer blood group system) | BC001288 | 2.58 |
| mitogen-activated protein kinase kinase 5 | U71088 | 2.58 |
| cofactor required for Sp1 transcriptional activation, subunit 2 (150kD) | AK023368 | 2.57 |
| phosphatidylinositol 4-kinase, catalytic, beta polypeptide | U81802 | 2.56 |
| HCF-binding transcription factor Zhangfei | AI206560 | 2.56 |
| kangai 1 (suppression of tumorigenicity 6, prostate; CD82 antigen (R2 leukocyte antigen, antigen detected by monoclonal and antibody IA4)) | NM_002231 | 2.56 |
| DEAD/H (Asp-Glu-Ala-Asp/His) box polypeptide 17 (72kD) | NM_030881 | 2.55 |
| RAP2B, member of RAS oncogene family | NM_002886 | 2.55 |
| eukaryotic translation initiation factor 4 gamma, 1 | BE966878 | 2.54 |
| KIAA0472 protein | AB007941 | 2.54 |
| isocitrate dehydrogenase 1 (NADP+), soluble | NM_005896 | 2.54 |
| CED-6 protein | AK023668 | 2.53 |
| ATP-binding cassette, sub-family D (ALD), member 3 | NM_002858 | 2.53 |
| eukaryotic translation initiation factor 5A | AA393940 | 2.53 |
| glycophorin E | NM_002102 | 2.53 |
| artemis protein | NM_022487 | 2.52 |
| inhibin, beta C | NM_005538 | 2.52 |
| reversion-inducing-cysteine-rich protein with kazal motifs | AK022897 | 2.52 |
| Consensus includes gb:AU147017 /FEA=EST /DB_XREF=gi:11008538 /DB_XREF=est:AU147017 /CLONE=HEMBB1002152 /UG=Hs.301905 Homo sapiens cDNA FLJ14080 fis, clone HEMBB1002152 | AU147017 | 2.52 |
| Mediterranean fever | NM_000243 | 2.52 |
| hypothetical protein FLJ20837 | NM_017964 | 2.52 |
| Consensus includes gb:AL049260.1 /DEF=Homo sapiens mRNA; cDNA DKFZp564E233 (from clone DKFZp564E233). /FEA=mRNA | AL049260 | 2.51 |

FIG. 4D-10

| | | |
|---|---|---|
| /DB_XREF=gi:4500007 /UG=Hs.302050 Homo sapiens mRNA; cDNA DKFZp564E233 (from clone DKFZp564E233) Consensus includes gb:AK025724.1 /DEF=Homo sapiens cDNA: FLJ22071 fis, clone HEP11691. /FEA=mRNA /DB_XREF=gi:10438333 /UG=Hs.326248 Homo sapiens cDNA: FLJ22071 fis, clone HEP11691 | AK025724 | 2.51 |
| coagulation factor V (proaccelerin, labile factor) | NM_000130 | 2.49 |
| ring finger protein 2 | NM_007212 | 2.49 |
| ATPase, Class I, type 8B, member 1 | BG252666 | 2.49 |
| homeo box A10 | AI375919 | 2.49 |
| Consensus includes gb:AF043583.1 /DEF=Homo sapiens clone ASMneg1-b3 immunoglobulin lambda chain VJ region, (IGL) mRNA, partial cds. /FEA=mRNA /GEN=IGL /PROD=immunoglobulin lambda chain /DB_XREF=gi:2865477 /UG=Hs.248083 Homo sapiens clone ASMneg1-b3 immu | AF043583 | 2.49 |
| nucleolar protein 4 | NM_003787 | 2.48 |
| macrophage stimulating, pseudogene 9 | U28055 | 2.48 |
| death-associated protein kinase 2 | AK026801 | 2.48 |
| ubiquitin specific protease 15 | AF106069 | 2.48 |
| Consensus includes gb:AW301806 /FEA=EST /DB_XREF=gi:6711483 /DB_XREF=est:xr56e11.x1 /CLONE=IMAGE:2764172 /UG=Hs.150551 ESTs, Weakly similar to ALU1_HUMAN ALU SUBFAMILY J SEQUENCE CONTAMINATION WARNING ENTRY H.sapiens | AW301806 | 2.47 |
| Fc fragment of IgG, low affinity IIIb, receptor for (CD16) | J04162 | 2.47 |
| Consensus includes gb:U43604.1 /DEF=Human unidentified mRNA, partial sequence. /FEA=mRNA /DB_XREF=gi:1171236 /UG=Hs.159901 Human unidentified mRNA, partial sequence | U43604 | 2.47 |
| prostate differentiation factor | AF003934 | 2.47 |
| X03453 Bacteriophage P1 cre recombinase protein (-5 and -3 represent transcript regions 5 prime and 3 prime respectively) | X03453 | 2.47 |
| protein kinase, cAMP-dependent, regulatory, type II, alpha | BC002763 | 2.47 |
| hypothetical protein FLJ10534 | AK026565 | 2.46 |
| Consensus includes gb:AW574933 /FEA=EST /DB_XREF=gi:7246472 /DB_XREF=est:UI-HF-BL0-abq-b-09-0-UI.s1 /CLONE=IMAGE:3057353 /UG=Hs.248844 ESTs, Weakly similar to ALU1_HUMAN ALU SUBFAMILY J SEQUENCE CONTAMINATION WARNING ENTRY H.sapiens | AW574933 | 2.46 |
| nerve growth factor receptor (TNFR superfamily, member 16) | NM_002507 | 2.46 |
| neuropilin 2 | AA295257 | 2.46 |
| erythrocyte membrane protein band 7.2 (stomatin) | AI537887 | 2.46 |
| ladinin 1 | U58994 | 2.46 |
| Consensus includes gb:AK026493.1 /DEF=Homo sapiens cDNA: FLJ22840 fis, clone KAIA4709. /FEA=mRNA /DB_XREF=gi:10439366 /UG=Hs.287293 Homo sapiens cDNA: FLJ22840 fis, clone KAIA4709 | AK026493 | 2.45 |
| heterogeneous nuclear ribonucleoprotein H1 (H) | AV753392 | 2.45 |
| adducin 2 (beta) | NM_017482 | 2.45 |
| zinc finger protein 76 (expressed in testis) | NM_003427 | 2.45 |

FIG. 4D-11

| Description | Accession | Value |
|---|---|---|
| Consensus includes gb:BE672313 /FEA=EST /DB_XREF=gi:10032854 /DB_XREF=est:7a59b10.x1 /CLONE=IMAGE:3223003 /UG=Hs.34054 Homo sapiens cDNA: FLJ22488 fis, clone HRC10948, highly similar to HSU79298 Human clone 23803 mRNA | BE672313 | 2.45 |
| dimethylarginine dimethylaminohydrolase 1 | AL078459 | 2.44 |
| PRO0644 protein | NM_014136 | 2.44 |
| coat protein gamma-cop | NM_016128 | 2.43 |
| Consensus includes gb:BG403790 /FEA=EST /DB_XREF=gi:13297238 /DB_XREF=est:602419627F1 /CLONE=IMAGE:4526599 /UG=Hs.158154 ESTs | BG403790 | 2.43 |
| sema domain, immunoglobulin domain (Ig), short basic domain, secreted, (semaphorin) 3C | NM_006379 | 2.43 |
| UDP-Gal:betaGlcNAc beta 1,3-galactosyltransferase, polypeptide 5 | NM_006057 | 2.42 |
| hypothetical protein FLJ20059 | NM_017644 | 2.42 |
| CDC14 cell division cycle 14 homolog A (S. cerevisiae) | NM_003672 | 2.41 |
| hypothetical protein FLJ23548 | NM_024590 | 2.41 |
| hypothetical protein FLJ22558 | NM_022747 | 2.41 |
| nuclear factor I/B | U70862 | 2.40 |
| hypothetical protein My014 | NM_030918 | 2.40 |
| hypothetical protein FLJ20006 | NM_017618 | 2.40 |
| WNT1 inducible signaling pathway protein 3 | AF143679 | 2.40 |
| dickkopf homolog 2 (Xenopus laevis) | NM_014421 | 2.39 |
| Consensus includes gb:AK021440.1 /DEF=Homo sapiens cDNA FLJ11378 fis, clone HEMBA1000456. /FEA=mRNA /DB_XREF=gi:10432625 /UG=Hs.6937 hypothetical protein FLJ10276 | AK021440 | 2.39 |
| Consensus includes gb:AL359578.1 /DEF=Homo sapiens mRNA; cDNA DKFZp547N163 (from clone DKFZp547N163). /FEA=mRNA /DB_XREF=gi:8655637 /UG=Hs.306511 Homo sapiens mRNA; cDNA DKFZp547N163 (from clone DKFZp547N163) | AL359578 | 2.39 |
| Consensus includes gb:AA629050 /FEA=EST /DB_XREF=gi:2541437 /DB_XREF=est:zu84a06.s1 /CLONE=IMAGE:744658 /UG=Hs.50760 ESTs, Highly similar to BimL H.sapiens | AA629050 | 2.39 |
| Dystonia musculorum of mouse, human homolog of | AL049215 | 2.39 |
| Consensus includes gb:AF131777.1 /DEF=Homo sapiens clone 25061 mRNA sequence. /FEA=mRNA /DB_XREF=gi:4406602 /UG=Hs.183475 Homo sapiens clone 25061 mRNA sequence | AF131777 | 2.39 |
| hypothetical protein FLJ22746 | NM_024785 | 2.38 |
| H1 histone family, member 4 | AL353759 | 2.38 |
| unc-51-like kinase 2 (C. elegans) | BG526973 | 2.38 |
| zinc finger protein 42 (myeloid-specific retinoic acid- responsive) | AI733248 | 2.38 |
| checkpoint suppressor 1 | AA860806 | 2.37 |
| protease, serine, 21 (testisin) | NM_006799 | 2.37 |
| peptidyl arginine deiminase, type V | AF229067 | 2.37 |
| calpain 9 (nCL-4) | AB038463 | 2.37 |
| sulfotransferase family, cytosolic, 1A, phenol-preferring, member 3 | L25275 | 2.37 |

FIG. 4D-12

| Description | Accession | Value |
|---|---|---|
| EphB3 | X75208 | 2.37 |
| craniofacial development protein 1 | D85939 | 2.36 |
| sialophorin (gpL115, leukosialin, CD43) | X60502 | 2.36 |
| Consensus includes gb:K00627.1 /DEF=human kpni repeat mrna (cdna clone pcd-kpni-8), 3 end. /FEA=mRNA /DB_XREF=gi:337653 /UG=Hs.203776 Human kpni repeat mrna (cdna clone pcd-kpni-8), 3 end | K00627 | 2.36 |
| Consensus includes gb:AK022045.1 /DEF=Homo sapiens cDNA FLJ11983 fis, clone HEMBB1001337. /FEA=mRNA /DB_XREF=gi:10433364 /UG=Hs.193162 Homo sapiens cDNA FLJ11983 fis, clone HEMBB1001337 | AK022045 | 2.36 |
| hypothetical protein FLJ20097 | NM_017667 | 2.36 |
| Consensus includes gb:M78162 /FEA=EST /DB_XREF=gi:273899 /DB_XREF=est:EST01755 /CLONE=HHCPN60 /UG=Hs.314534 ESTs, Moderately similar to ALU5_HUMAN ALU SUBFAMILY SC SEQUENCE CONTAMINATION WARNING ENTRY H.sapiens | M78162 | 2.35 |
| hypothetical protein FLJ20019 | NM_017624 | 2.35 |
| calcium/calmodulin-dependent serine protein kinase (MAGUK family) | AB039327 | 2.35 |
| M10098 Human 18S rRNA gene, complete (_5, _M, _3 represent transcript regions 5 prime, Middle, and 3 prime respectively) | M10098 | 2.35 |
| Consensus includes gb:S80491.1 /DEF=stem cell factor (alternatively spliced) human, preimplantation embryos, blastocysts, mRNA Partial, 180 nt. /FEA=mRNA /GEN=stem cell factor, SCF /PROD=stem cell factor /DB_XREF=gi:1246099 /UG=Hs.123028 Stem cell facto | S80491 | 2.35 |
| hemoglobin, gamma G | NM_000184 | 2.34 |
| transcription factor 20 (AR1) | U19345 | 2.34 |
| Consensus includes gb:AK023783.1 /DEF=Homo sapiens cDNA FLJ13721 fis, clone PLACE2000450. /FEA=mRNA /DB_XREF=gi:10435820 /UG=Hs.289035 Homo sapiens cDNA FLJ13721 fis, clone PLACE2000450 | AK023783 | 2.34 |
| CGI-58 protein | NM_016006 | 2.34 |
| hypothetical protein FLJ10254 | NM_018041 | 2.34 |
| interleukin 1 receptor antagonist | BE563442 | 2.33 |
| Bloom syndrome | NM_000057 | 2.33 |
| Consensus includes gb:AA780524 /FEA=EST /DB_XREF=gi:2839855 /DB_XREF=est:ac71f01.s1 /CLONE=IMAGE:868057 /UG=Hs.294072 ESTs, Weakly similar to ALU1_HUMAN ALU SUBFAMILY J SEQUENCE CONTAMINATION WARNING ENTRY H.sapiens | AA780524 | 2.33 |
| potassium inwardly-rectifying channel, subfamily J, member 8 | NM_004982 | 2.33 |
| hypothetical protein FLJ14310 | NM_025028 | 2.33 |
| thrombospondin 1 | NM_003246 | 2.33 |
| calmodulin 1 (phosphorylase kinase, delta) | M27319 | 2.32 |
| leukocyte immunoglobulin-like receptor, subfamily B (with TM and ITIM domains), member 3 | AF009643 | 2.32 |
| M10098 Human 18S rRNA sequence, length 1969 bases, 3 prime target bases 1293-1938 | M10098 | 2.32 |
| hypothetical protein FLJ23447 | NM_024825 | 2.32 |

FIG. 4D-13

| | | |
|---|---|---|
| KIAA0304 gene product | AF105279 | 2.32 |
| a disintegrin and metalloproteinase domain 17 (tumor necrosis factor, alpha, converting enzyme) | NM_003183 | 2.32 |
| SRY (sex determining region Y)-box 21 | NM_007084 | 2.32 |
| phosphatidylinositol-4-phosphate 5-kinase, type II, alpha | NM_005028 | 2.32 |
| homeo box C8 | NM_022658 | 2.32 |
| CGI-86 protein | BC000637 | 2.32 |
| guanine nucleotide binding protein 13, gamma | NM_016541 | 2.31 |
| potassium voltage-gated channel, delayed-rectifier, subfamily S, member 3 | NM_002252 | 2.31 |
| Consensus includes gb:AK000864.1 /DEF=Homo sapiens cDNA FLJ10602 fis, clone HEMBA1000046. /FEA=mRNA /DB_XREF=gi:7021188 /UG=Hs.296522 Homo sapiens cDNA FLJ10002 fis, clone HEMBA1000046 | AK000864 | 2.31 |
| nuclear LIM interactor-interacting factor | AF229163 | 2.31 |
| Consensus includes gb:AW451711 /FEA=EST /DB_XREF=gi:6992487 /DB_XREF=est:UI-H-BI3-ale-c-02-0-UI.s1 /CLONE=IMAGE:2736386 /UG=Hs.313760 ESTs | AW451711 | 2.31 |
| Consensus includes gb:AW090043 /FEA=EST /DB_XREF=gi:6047387 /DB_XREF=est:xd01c05.x1 /CLONE=IMAGE:2592488 /UG=Hs.326464 Homo sapiens cDNA: FLJ21702 fis, clone COL09874 | AW090043 | 2.31 |
| elaC homolog 1 (E. coli) | NM_018696 | 2.31 |

COMPOSITIONS AND METHODS FOR INHIBITING THE PROLIFERATION OF CELLS

This application is a Divisional of U.S. patent application Ser. No. 10/427,211, filed May 1, 2003 now U.S. Pat. No. 7,572,788, which is a Continuation in Part of U.S. patent application Ser. No. 10/217,878, filed Aug. 13, 2002 now abandoned, which is a continuation of U.S. patent application Ser. No. 09/767,283, filed Jan. 22, 2001 now U.S. Pat. No. 7,125,866, which is a continuation of U.S. patent application Ser. No. 09/700,101, filed Nov. 8, 2000, which is the National entry of PCTUS00/11599 filed Apr. 27, 2000, which claims priority to U.S. Provisional Application Ser. No. 60/131,761, filed Apr. 30, 1999, to U.S. Provisional Application Ser. No. 60/165,511, filed Nov. 15, 1999, and to U.S. Provisional Application Ser. No. 60/191,855, filed Mar. 24, 2000. U.S. application Ser. No. 10/217,878 also claims priority to U.S. Provisional Application Ser. No. 60/312,560, filed Aug. 15, 2001, and to U.S. Provisional Application Ser. No. 60/313,689, filed Aug. 20, 2001, and to U.S. Provisional Application Ser. No. 60/396,670, filed Jul. 18, 2002. Each aforementioned application is specifically incorporated herein by reference in it entirety.

This application was made with government support under GM046831 and AI047450 awarded by the National Institutes of Health. The government has certain rights in the invention.

FIELD OF THE INVENTION

The present invention relates to novel chemical compounds, methods for their discovery, and their therapeutic use. In particular, the present invention provides benzodiazepine derivatives and related compounds and methods of using benzodiazepine derivatives and related compounds as therapeutic agents to treat a number of conditions associated with the faulty regulation of the processes of programmed cell death, autoimmunity, inflammation, hyperproliferation, and the like.

BACKGROUND OF THE INVENTION

Multicellular organisms exert precise control over cell number. A balance between cell proliferation and cell death achieves this homeostasis. Cell death occurs in nearly every type of vertebrate cell via necrosis or through a suicidal form of cell death, known as apoptosis. Apoptosis is triggered by a variety of extracellular and intracellular signals that engage a common, genetically programmed death mechanism.

Multicellular organisms use apoptosis to instruct damaged or unnecessary cells to destroy themselves for the good of the organism. Control of the apoptotic process therefore is very important to normal development, for example, fetal development of fingers and toes requires the controlled removal, by apoptosis, of excess interconnecting tissues, as does the formation of neural synapses within the brain. Similarly, controlled apoptosis is responsible for the sloughing off of the inner lining of the uterus (the endometrium) at the start of menstruation. While apoptosis plays an important role in tissue sculpting and normal cellular maintenance, it is also the primary defense against cells and invaders (e.g., viruses) which threaten the well being of the organism.

Not surprisingly many diseases are associated with dys-regulation of the process of cell death. Experimental models have established a cause-effect relationship between aberrant apoptotic regulation and the pathenogenicity of various neoplastic, autoimmune and viral diseases. For instance, in the cell mediated immune response, effector cells (e.g., cytotoxic T lymphocytes "CTLs") destroy virus-infected cells by inducing the infected cells to undergo apoptosis. The organism subsequently relies on the apoptotic process to destroy the effector cells when they are no longer needed. Autoimmunity is normally prevented by the CTLs inducing apoptosis in each other and even in themselves. Defects in this process are associated with a variety of autoimmune diseases such as lupus erythematosus and rheumatoid arthritis.

Multicellular organisms also use apoptosis to instruct cells with damaged nucleic acids (e.g., DNA) to destroy themselves prior to becoming cancerous. Some cancer-causing viruses overcome this safeguard by reprogramming infected (transformed) cells to abort the normal apoptotic process. For example, several human papilloma viruses (HPVs) have been implicated in causing cervical cancer by suppressing the apoptotic removal of transformed cells by producing a protein (E6) which inactivates the p53 apoptosis promoter. Similarly, the Epstein-Barr virus (EBV), the causative agent of mononucleosis and Burkitt's lymphoma, reprograms infected cells to produce proteins that prevent normal apoptotic removal of the aberrant cells thus allowing the cancerous cells to proliferate and to spread throughout the organism.

Still other viruses destructively manipulate a cell's apoptotic machinery without directly resulting in the development of a cancer. For example, the destruction of the immune system in individuals infected with the human immunodeficiency virus (HIV) is thought to progress through infected $CD4^+$ T cells (about 1 in 100,000) instructing uninfected sister cells to undergo apoptosis.

Some cancers that arise by non-viral means have also developed mechanisms to escape destruction by apoptosis. Melanoma cells, for instance, avoid apoptosis by inhibiting the expression of the gene encoding Apaf-1. Other cancer cells, especially lung and colon cancer cells, secrete high levels of soluble decoy molecules that inhibit the initiation of CTL mediated clearance of aberrant cells. Faulty regulation of the apoptotic machinery has also been implicated in various degenerative conditions and vascular diseases.

It is apparent that the controlled regulation of the apoptotic process and its cellular machinery is vital to the survival of multicellular organisms. Typically, the biochemical changes that occur in a cell instructed to undergo apoptosis occur in an orderly procession. However, as shown above, flawed regulation of apoptosis can cause serious deleterious effects in the organism.

There have been various attempts to control and restore regulation of the apoptotic machinery in aberrant cells (e.g., cancer cells). For example, much work has been done to develop cytotoxic agents to destroy aberrant cells before they proliferate. As such, cytotoxic agents have widespread utility in both human and animal health and represent the first line of treatment for nearly all forms of cancer and hyperproliferative autoimmune disorders like lupus erythematosus and rheumatoid arthritis.

Many cytotoxic agents in clinical use exert their effect by damaging DNA (e.g., cis-diaminodichroplatanim(II) cross-links DNA, whereas bleomycin induces strand cleavage). The result of this nuclear damage, if recognized by cellular factors like the p53 system, is to initiate an apoptotic cascade leading to the death of the damaged cell.

However, existing cytotoxic chemotherapeutic agents have serious drawbacks. For example, many known cytotoxic agents show little discrimination between healthy and diseased cells. This lack of specificity often results in severe side effects that can limit efficacy and/or result in early mortality. Moreover, prolonged administration of many existing cytotoxic agents results in the expression of resistance genes (e.g., bcl-2 family or multi-drug resistance (MDR) proteins) that render further dosing either less effective or useless. Some cytotoxic agents induce mutations into p53 and related proteins. Based on these considerations, ideal cytotoxic drugs should only kill diseased cells and not be susceptible to chemo-resistance.

One strategy to selectively kill diseased cells is to develop drugs that selectively recognize molecules expressed in diseased cells. Thus, effective cytotoxic chemotherapeutic agents, would recognize disease indicative molecules and induce (e.g., either directly or indirectly) the death of the diseased cell. Although markers on some types of cancer cells have been identified and targeted with therapeutic antibodies and small molecules, unique traits for diagnostic and therapeutic exploitation are not known for most cancers. Moreover, for diseases like lupus, specific molecular targets for drug development have not been identified.

What are needed are improved compositions and methods for regulating the apoptotic processes in subjects afflicted with diseases and conditions characterized by faulty regulation of these processes (e.g., viral infections, hyperproliferative autoimmune disorders, chronic inflammatory conditions, and cancers).

SUMMARY

The present invention provides novel compounds that find use in treating a number of diseases and conditions and that find use in research, compound screening, and diagnostic applications. The present invention also provides uses of these novel compounds, as well as the use of known compounds, that elicit particular biological responses (e.g., compounds that bind to particular target molecules and/or cause particular cellular events). Such compounds and uses are described throughout the present application and represent a diverse collection of compositions and applications.

Certain preferred compositions and uses are described below. The present invention is not limited to these particular compositions and uses.

The present invention provides a number of useful compositions as described throughout the present application. Certain preferred embodiments of the present involve compositions include a composition comprising the following formula:

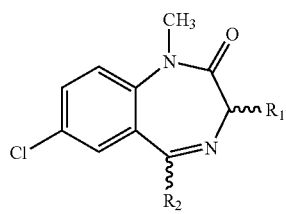

wherein $R_1$ is selected from napthalalanine; phenol; 1-Napthalenol; 2-Napthalenol;

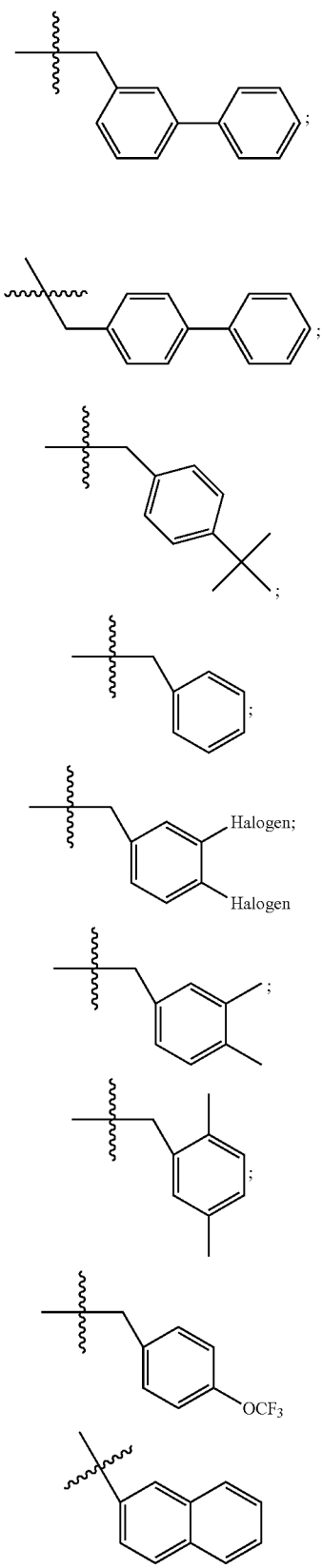

and quinolines; wherein $R_2$ is selected from the group consisting of:

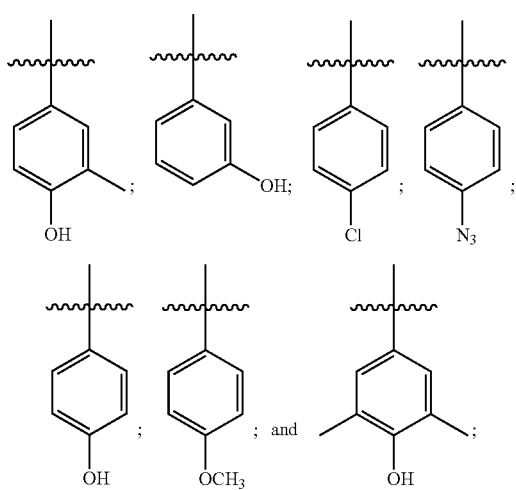

and wherein $R_1$ and $R_2$ include both R or S enantiomeric forms and racemic mixtures.

Other preferred embodiments of the present involve compositions include a composition comprising the following formula:

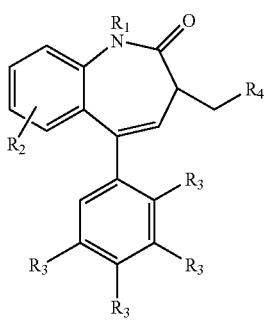

wherein R1 is selected from H, alkyl, or substituted alkyl; wherein R2 is selected from hydrogen, a hydroxy, an slkoxy, a halo, an amino, a lower-alkyl, a substituted amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, a heterocyclic; wherein R3 is selected from H, alkyl, or substituted alkyl, and wherein at most one substituent is a hydroxyl subgroup; wherein R4 is selected from

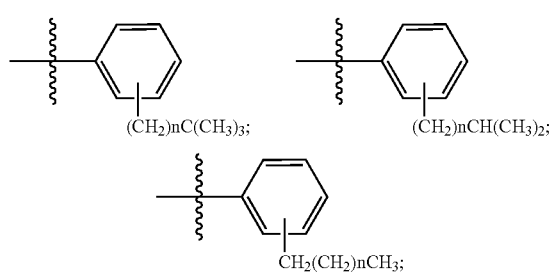

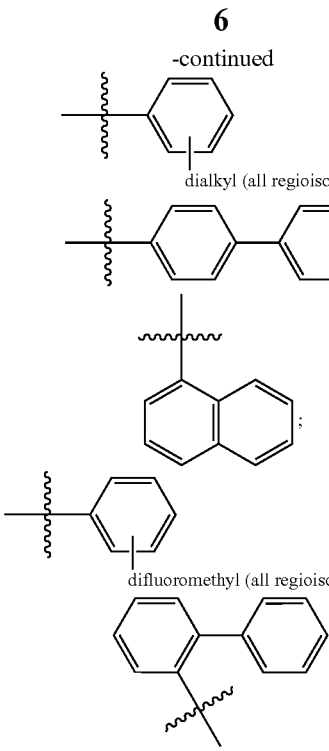

wherein n=0-5; and wherein $R_1$, $R_2$, $R_3$ and $R_4$ include both R or S enantiomeric forms and racemic mixtures.

Still other preferred embodiments of the present involve compositions include a composition comprising the following formula:

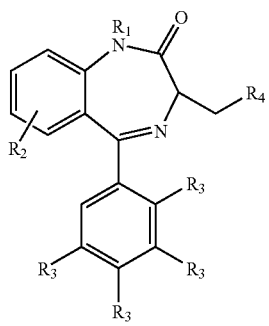

wherein R1 is selected from H, alkyl, or substituted alkyl; wherein R2 is selected from hydrogen, a hydroxy, an alkoxy, a halo, an amino, a lower-alkyl, a substituted amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, a heterocyclic; wherein R3 is selected from H, alkyl, or substituted alkyl, and wherein at most one substituent is a hydroxyl subgroup; wherein R4 is selected from

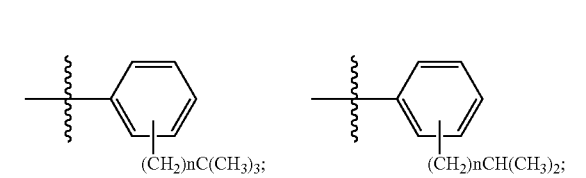

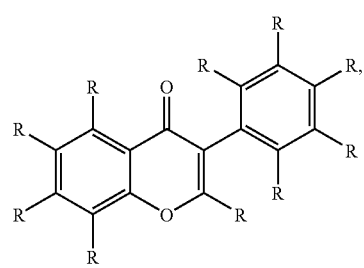

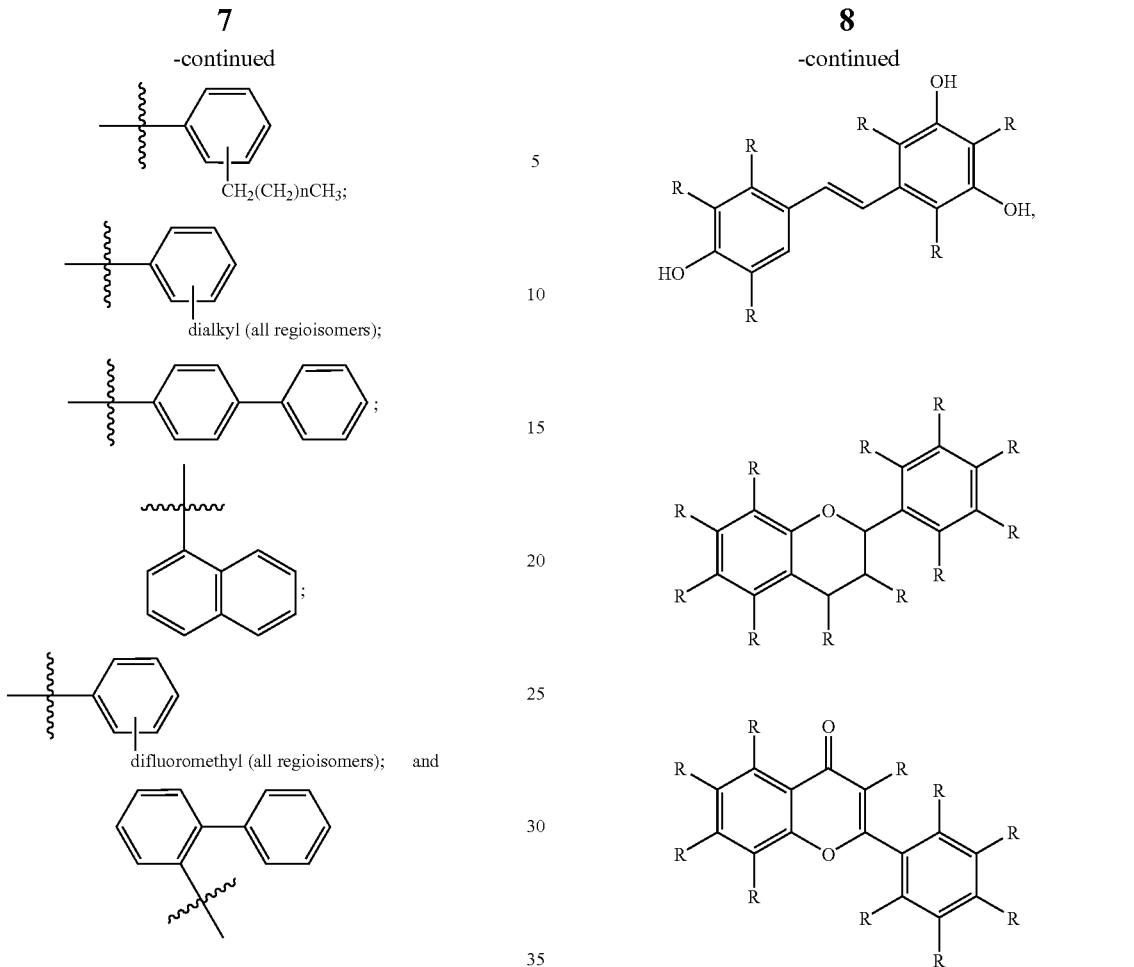

wherein n=0-5; and wherein $R_1$, $R_2$, $R_3$ and $R_4$ include both R or S enantiomeric forms and racemic mixtures.

In other preferred embodiments, the present invention provides a pharmaceutical composition. In such embodiments, the present invention provides a compound that binds to oligomycin conferring protein, and an agent (e.g. resveratrol, picetannol, estrogen, lansoprazole).

The present invention also provides methods and compositions useful in regulating cellular death. In preferred embodiments, the present invention provides a subject and a composition comprising a formula selected from the group consisting of

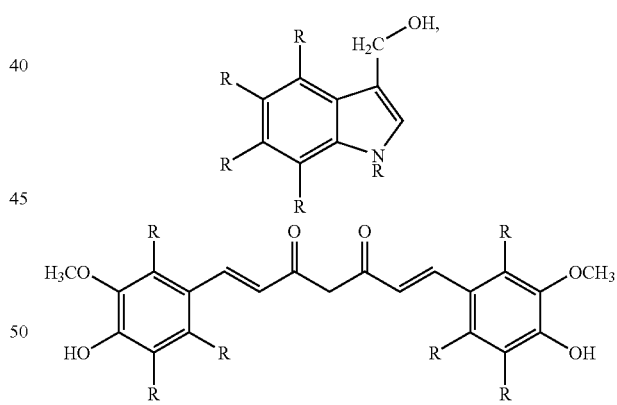

wherein R is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic; and such a composition is administered to the subject.

In still other preferred embodiments, the present invention provides compositions and methods for regulating cellular proliferation. In such embodiments, the present invention provides a subject and a composition comprising a formula selected from

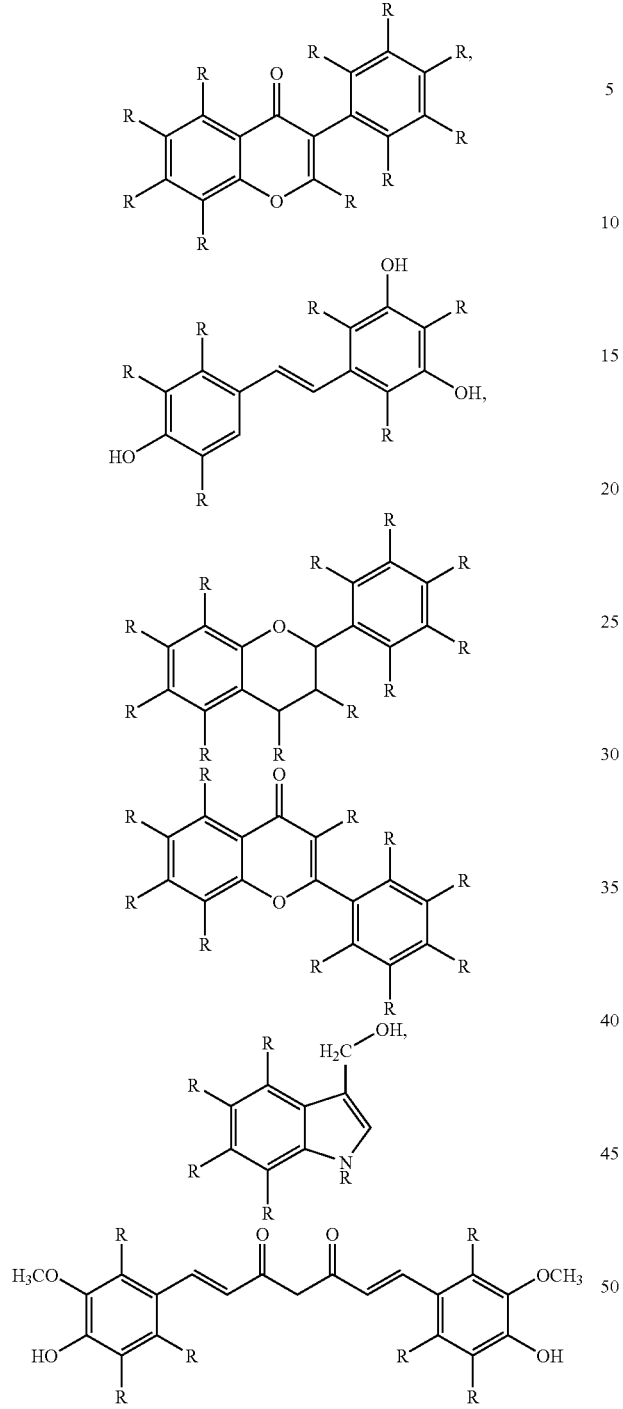

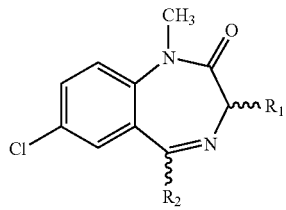

wherein R1 comprises a hydrophobic aromatic group larger than benzene; wherein R2 comprises a phenolic hydroxyl group; and wherein $R_1$, and $R_2$ include both R or S enantiomeric forms and racemic mixtures. In additional embodiments, the cells are exposed to the composition under conditions such that said composition binds to the oligomycin sensitivity conferring protein so as to increase superoxide levels or alter cellular ATP levels in said cells.

In other embodiments, target cells are in vitro cells. In other embodiments, the target cells are in vivo cells. In still other embodiments, the target cells are ex vivo cells. In yet other embodiments, the target cells are cancer cells. In some embodiments, the target cells are selected from the group consisting of B cells, T cells, and granulocytes.

In other embodiments used in the regulation of cellular death, the present invention also provides the following compositions:

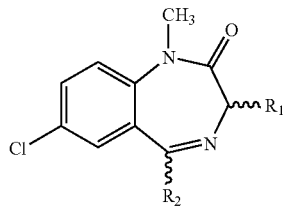

wherein $R_1$ is selected from group consisting of: napthalanine; phenol; 1-Napthalenol; 2-Napthalenol;

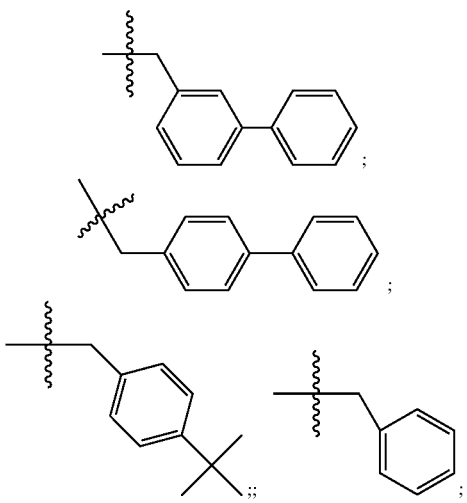

wherein R is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic; and the composition is administered to the subject.

The present invention provides a number of methods for influencing the fate of cells, tissues, and organisms. Certain preferred embodiments of the present invention involve methods for regulating cell death. In such embodiments, the present invention provides target cells having mitochondria and a composition comprising the following formula:

-continued

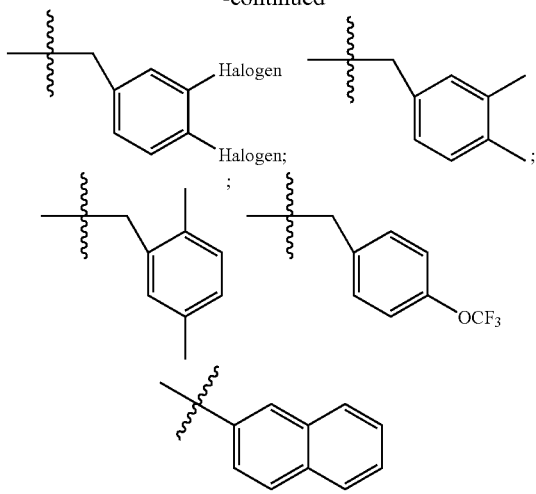

and quinolines; wherein $R_2$ is selected from the group consisting of:

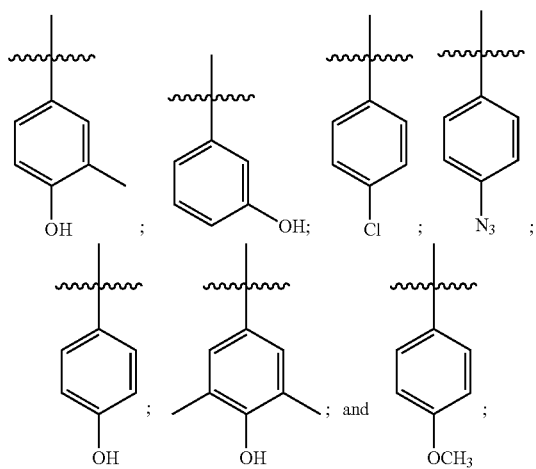

and wherein $R_1$ and $R_2$ include both R or S enantiomeric forms and racemic mixtures.

In preferred embodiments wherein the present invention regulates cellular death, exposure of the composition to target cells results in an increase in cell death of the target cells.

The present invention also provides methods and compositions for regulating cellular proliferation. In such embodiments, the present invention provides proliferating target cells having mitochondria, and a composition comprising the following formula:

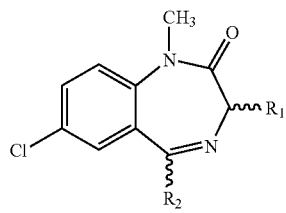

wherein comprises a hydrophobic aromatic group larger than benzene; wherein R2 comprises a phenolic hydroxyl group;
wherein $R_1$ and $R_2$ include both R or S enantiomeric forms and racemic mixtures; and wherein the cells are exposed to the composition under conditions such that the composition binds to the mitochondrial ATP synthase complex so as to increase superoxide levels or alter cellular ATP levels in the cells. In preferred embodiments, the composition binds to oligomycin sensitivity conferring protein.

In some embodiments, the target cells are in vitro cells. In other embodiments, the target cells are in vivo cells. In still other embodiments, the target cells are ex vivo cells. In other embodiments, the target cells are cancer cells. In yet other embodiments, the target cells are selected from the group consisting of B cells, T cells, and granulocytes. In still further embodiments, the target cells are proliferating cells.

In other embodiments wherein the present invention regulates cellular proliferation, the present invention provides the following composition:

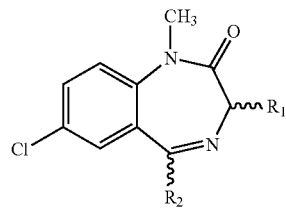

wherein $R_1$ is selected from napthalalanine; phenol; 1-Napthalenol; 2-Napthalenol;

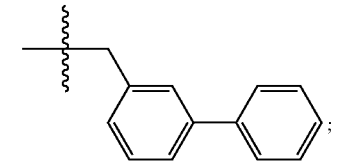

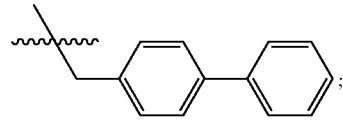

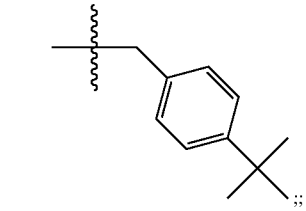

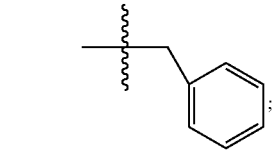

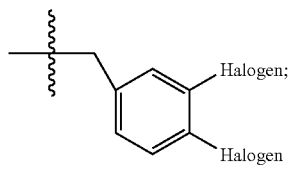

-continued

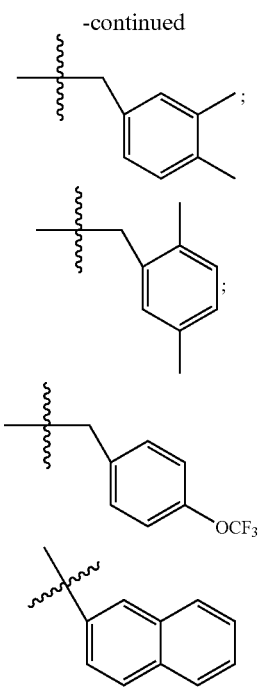

and quinolines; wherein R$_2$ is selected from the group consisting of:

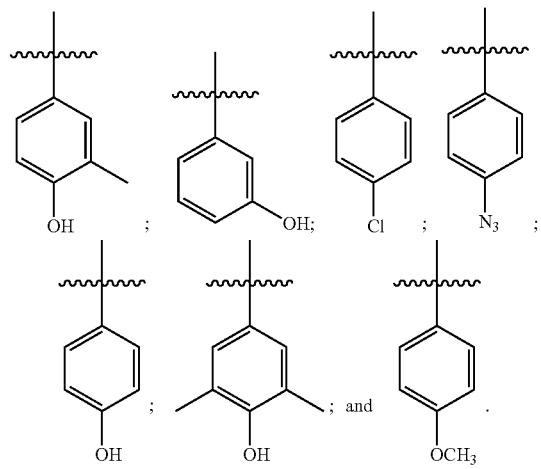

DESCRIPTION OF THE FIGURES

FIG. 1 shows data demonstrating that the OSCP component is a binding protein for Bz-423.

FIG. 2 is a graph showing the binding isotherm of Bz-423 and purified human OSCP.

FIG. 3 shows siRNA regulation of OSCP.

FIG. 4 shows data showing gene expression profiles of cells treated by the compounds of the present invention. Data from an expression analysis for genes up-regulated in the presence of Bz-423 is presented in FIG. 4A. Data from an expression analysis for genes down-regulated in the presence of Bz-423 is presented in FIG. 4B. Data from an expression analysis for genes up-regulated in the presence of Bz-OMe is presented in FIG. 4C. Data from an expression analysis for genes down-regulated in the presence of Bz-OMe is presented in FIG. 4D.

DEFINITIONS

To facilitate an understanding of the present invention, a number of terms and phrases are defined below.

As used herein, the term "benzodiazepine" refers to a seven membered non-aromatic heterocyclic ring fused to a phenyl ring wherein the seven-membered ring has two nitrogen atoms, as part of the heterocyclic ring. In some aspects, the two nitrogen atoms are in 1 and 4 positions, as shown in the general structure below.

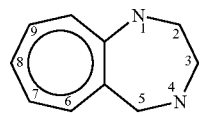

The benzodiazepine can be substituted with one keto group (typically at the 2-position), or with two keto groups, one each at the 2- and 5-positions. When the benzodiazepine has two keto groups, one each at the 2- and 5-positions, it is referred to as benzodiazepine-2,5-dione. Most generally, the benzodiazepine is further substituted either on the six-membered phenyl ring or on the seven-membered heterocyclic ring or on both rings by a variety of substituents. These substituents are described more fully herein.

The term "larger than benzene" refers to any chemical group containing 7 or more non-hydrogen atoms.

As used herein, the term "substituted aliphatic" refers to an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of no more than three fused rings at least one of which is aromatic, and where at least one of the hydrogen atoms on a ring carbon has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to a cycloalkane possessing less than 8 carbons or a fused ring system consisting of no more than three fused cycloaliphatic rings. Examples of such include, but are not limited to, decalin and the like.

As used herein, the term "substituted cycloaliphatic" refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl and the like.

As used herein, the term "heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur. Examples of such include, but are not limited to, morpholino and the like.

As used herein, the term "substituted heterocyclic" refers to a cycloalkane and/or an aryl ring system, possessing less than 8 carbons, or a fused ring system consisting of no more than three fused rings, where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "linker" refers to a chain containing up to and including eight contiguous atoms connecting two different structural moieties where such atoms are, for example, carbon, nitrogen, oxygen, or sulfur. Ethylene glycol is one non-limiting example.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamino" shall mean any primary or secondary amino that is acetylated. Examples of such include, but are not limited to, acetamide and the like.

The term "derivative" of a compound, as used herein, refers to a chemically modified compound wherein the chemical modification takes place either at a functional group of the compound or on the aromatic ring. Non-limiting examples of 1,4-benzodiazepine derivatives of the present invention may include N-acetyl, N-methyl, N-hydroxy groups at any of the available nitrogens in the compound. Additional derivatives may include those having a trifluoromethyl group on the phenyl ring.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of benzodiazepine compound(s), and optionally one or more other agents) for a condition characterized by the dysregulation of apoptotic processes.

The term "diagnosed," as used herein, refers to the to recognition of a disease by its signs and symptoms (e.g., resistance to conventional therapies), or genetic analysis, pathological analysis, histological analysis, and the like.

As used herein, the terms "anticancer agent," or "conventional anticancer agent" refer to any chemotherapeutic compounds, radiation therapies, or surgical interventions, used in the treatment of cancer.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g. with an immortal phenotype), primary cell cultures, finite cell lines (e.g., non-transformed cells), and any other cell population maintained in vitro, including oocytes and embryos.

In preferred embodiments, the "target cells" of the compositions and methods of the present invention include, refer to, but are not limited to, lymphoid cells or cancer cells. Lymphoid cells include B cells, T cells, and granulocytes. Granulocytes include eosinophils and macrophages. In some embodiments, target cells are continuously cultured cells or uncultered cells obtained from patient biopsies.

Cancer cells include tumor cells, neoplastic cells, malignant cells, metastatic cells, and hyperplastic cells. Neoplastic cells can be benign or malignant. Neoplastic cells are benign if they do not invade or metastasize. A malignant cell is one that is able to invade and/or metastasize. Hyperplasia is a pathologic accumulation of cells in a tissue or organ, without significant alteration in structure or function.

In one specific embodiment, the target cells exhibit pathological growth or proliferation. As used herein, the term "pathologically proliferating or growing cells" refers to a localized population of proliferating cells in an animal that is not governed by the usual limitations of normal growth.

As used herein, the term "un-activated target cell" refers to a cell that is either in the $G_o$ phase or one in which a stimulus has not been applied.

As used herein, the term "activated target lymphoid cell" refers to a lymphoid cell that has been primed with an appropriate stimulus to cause a signal transduction cascade, or alternatively, a lymphoid cell that is not in $G_o$ phase. Activated lymphoid cells may proliferate, undergo activation induced cell death, or produce one or more of cytotoxins, cytokines, and other related membrane-associated proteins characteristic of the cell type (e.g., $CD8^+$ or $CD4^+$). They are also capable of recognizing and binding any target cell that displays a particular antigen on its surface, and subsequently releasing its effector molecules.

As used herein, the term "activated cancer cell" refers to a cancer cell that has been primed with an appropriate stimulus to cause a signal transduction. An activated cancer cell may or may not be in the $G_o$ phase.

An activating agent is a stimulus that upon interaction with a target cell results in a signal transduction cascade. Examples of activating stimuli include, but are not limited to, small molecules, radiant energy, and molecules that bind to cell activation cell surface receptors. Responses induced by activation stimuli can be characterized by changes in, among others, intracellular $Ca^{2+}$, superoxide, or hydroxyl radical levels; the activity of enzymes like kinases or phosphatases; or the energy state of the cell. For cancer cells, activating agents also include transforming oncogenes.

In one aspect, the activating agent is any agent that binds to a cell surface activation receptor. These can be selected from the group consisting of a T cell receptor ligand, a B cell activating factor ("BAFF"), a TNF, a Fas ligand (FasL), a CD40 ligand, a proliferation inducing ligand ("APRIL"), a cytokine, a chemokine, a hormone, an amino acid (e.g., glutamate), a steroid, a B cell receptor ligand, gamma irradiation, UV irradiation, an agent or condition that enhances cell stress, or an antibody that specifically recognizes and binds a cell surface activation receptor (e.g. anti-CD4, anti-CD8, anti-CD20, anti-TACI, anti-BCMA, anti-TNF receptor, anti-CD40, anti-CD3, anti-CD28, anti-B220, anti-CD38, and-CD19, and anti-CD21). BCMA is B cell maturation antigen receptor and TACI is transmembrane activator and CAML interactor. (Gross, A. et al. (2000); Laabi, Y et al. (1992) and Madry, C. et al. (1998)). Antibodies include monoclonal or polyclonal or a mixture thereof.

Examples of a T cell ligand include, but are not limited to, a peptide that binds to an MHC molecule, a peptide MHC complex, or an antibody that recognizes components of the T cell receptor.

Examples of a B cell ligand include, but are not limited to, a molecule or antibody that binds to or recognizes components of the B cell receptor.

Examples of reagents that bind to a cell surface activation receptor include, but are not limited to, the natural ligands of these receptors or antibodies raised against them (e.g., anti-CD20). RITUXIN (Genentech, Inc., San Francisco, Calif.) is a commercially available anti-CD 20 chimeric monoclonal antibody.

Examples of agents or conditions that enhance cell stress include heat, radiation, oxidative stress, or growth factor withdrawal and the like. Examples of growth factors include, but are not limited to serum, IL-2, platelet derived growth factor ("PDGF"), and the like.

As used herein, the term "effective amount" refers to the amount of a compound (e.g., benzodiazepine) sufficient to effect beneficial or desired results. An effective amount can be administered in one or more administrations, applications or dosages and is not limited intended to be limited to a particular formulation or administration route.

As used herein, the term "dysregulation of the process of cell death" refers to any aberration in the ability of (e.g., predisposition) a cell to undergo cell death via either necrosis or apoptosis. Dysregulation of cell death is associated with or induced by a variety of conditions, including for example, autoimmune disorders (e.g., systemic lupus erythematosus, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis.

It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disorder," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo, invasion or metastasis and malignant if it does either of these. A metastatic cell or tissue means that the cell can invade and destroy neighboring body structures. Hyperplasia is a form of cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include rheumatoid arthritis, Sjögren's syndrome, graft versus host disease, myasthenia gravis, systemic lupus erythematosus ("SLE"), and the like.

As used herein, the term "chronic inflammatory condition" refers to a condition wherein the organism's immune cells are activated. Such a condition is characterized by a persistent inflammatory response with pathologic sequelae. This state is characterized by infiltration of mononuclear cells, proliferation of fibroblasts and small blood vessels, increased connective tissue, and tissue destruction. Examples of chronic inflammatory diseases include, but are not limited to, Crohn's disease, psoriasis, chronic obstructive pulmonary disease, inflammatory bowel disease, multiple sclerosis, and asthma. Autoimmune diseases such as rheumatoid arthritis and systemic lupus erythematosus can also result in a chronic inflammatory state.

As used herein, the term "co-administration" refers to the administration of at least two agent(s) (e.g., benzodiazepines) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the terms "solid phase supports" or "solid supports," are used in their broadest sense to refer to a number of supports that are available and known to those of ordinary skill in the art. Solid phase supports include, but are not limited to, silica gels, resins, derivatized plastic films, glass beads, cotton, plastic beads, alumina gels, and the like. As used herein, "solid supports" also include synthetic antigen-presenting matrices, cells, liposomes, and the like. A suitable solid phase support may be selected on the basis of desired end use and suitability for various protocols. For example, for peptide synthesis, solid phase supports may refer to resins such as polystyrene (e.g., PAM-resin obtained from Bachem, Inc., Peninsula Laboratories, etc.), POLYHIPE) resin (obtained from Aminotech, Canada), polyamide resin (obtained from Peninsula Laboratories), polystyrene resin grafted with polyethylene glycol (TENTAGEL, Rapp Polymere, Tubingen, Germany) or polydimethylacrylamide resin (obtained from Milligen/Biosearch, California).

As used herein, the term "pathogen" refers a biological agent that causes a disease state (e.g., infection, cancer, etc.) in a host. "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. Also included within this term are prokaryotic organisms which are gram negative or gram positive. "Gram negative" and "gram positive" refer to staining patterns with the Gram-staining process which is well known in the art. (See e.g., Finegold and Martin, Diagnostic Microbi-ology, 6th Ed., CV Mosby St. Louis, pp. 13-15 [1982]). "Gram positive bacteria" are bacteria which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the term "microorganism" refers to any species or type of microorganism, including but not limited to, bacteria, archaea, fungi, protozoans, mycoplasma, and parasitic organisms. The present invention contemplates that a number of microorganisms encompassed therein will also be pathogenic to a subject.

As used herein, the term "fungi" is used in reference to eukaryotic organisms such as the molds and yeasts, including dimorphic fungi.

As used herein, the term "virus" refers to minute infectious agents, which with certain exceptions, are not observable by light microscopy, lack independent metabolism, and are able to replicate only within a living host cell. The individual particles (i.e., virions) typically consist of nucleic acid and a protein shell or coat; some virions also have a lipid containing membrane. The term "virus" encompasses all types of viruses, including animal, plant, phage, and other viruses.

The term "sample" as used herein is used in its broadest sense. A sample suspected of indicating a condition characterized by the dysregulation of apoptotic function may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "antigen binding protein" refers to proteins which bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g. diphtheria toxoid, bovine serum albumin (BSA), or keyhole limpet hemocyanin [KLH]). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]).

According to the invention, techniques described for the production of single chain antibodies (U.S. Pat. No. 4,946, 778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g. gel agglutination assays, hemagglutination assays, etc.), complement fixation assays, immunofluorescence assays, protein A assays, and immunoelectrophoresis assays, etc.) etc.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

The term "epitope" as used herein refers to that portion of an antigen that makes contact with a particular immunoglobulin. When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "modulate" refers to the activity of a compound (e.g., benzodiazepine compound) to affect (e.g., to promote or retard) an aspect of cellular function, including, but not limited to, cell growth, proliferation, apoptosis, and the like.

As used herein, the term "competes for binding" is used in reference to a first molecule (e.g., a first benzodiazepine derivative) with an activity that binds to the same substrate (e.g., the oligomycin sensitivity conferring protein in mitochondrial ATP synthase) as does a second molecule (e.g., a second benzodiazepine derivative or other molecule that binds to the oligomycin sensitivity conferring protein in mitochondrial ATP synthase, etc.). The efficiency (e.g., kinetics or thermodynamics) of binding by the first molecule may be the same as, or greater than, or less than, the efficiency of the substrate binding to the second molecule. For example, the equilibrium binding constant ($K_D$) for binding to the substrate may be different for the two molecules.

As used herein, the term "instructions for administering said compound to a subject," and grammatical equivalents thereof, includes instructions for using the compositions contained in a kit for the treatment of conditions characterized by the dysregulation of apoptotic processes in a cell or tissue (e.g., providing dosing, route of administration, decision trees for treating physicians for correlating patient-specific characteristics with therapeutic courses of action). The term also specifically refers to instructions for using the compositions contained in the kit to treat autoimmune disorders (e.g., systemic lupus erythematosus, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes virus, papilloma virus, HIV), and other conditions such as osteoarthritis and atherosclerosis, and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In preferred embodiments, "test compounds" are agents that modulate apoptosis in cells.

As used herein, the term "third party" refers to any entity engaged in selling, warehousing, distributing, or offering for sale a test compound contemplated for administered with a compound for treating conditions characterized by the dysregulation of apoptotic processes.

GENERAL DESCRIPTION OF THE INVENTION

As a class of drugs, benzodiazepine compounds have been widely studied and reported to be effective medicaments for treating a number of disease. For example, U.S. Pat. Nos. 4,076823, 4,110,337, 4,495,101, 4,751,223 and 5,776,946, each incorporated herein by reference in its entirety, report that certain benzodiazepine compounds are effective as analgesic and anti-inflammatory agents. Similarly, U.S. Pat. No. 5,324,726 and U.S. Pat. No. 5,597,915, each incorporated by reference in its entirety, report that certain benzodiazepine compounds are antagonists of cholecystokinin and gastrin and thus might be useful to treat certain gastrointestinal disorders.

Other benzodiazepine compounds have been studied as inhibitors of human neutrophil elastase in the treating of human neutrophil elastase-mediated conditions such as myocardial ischemia, septic shock syndrome, among others (See e.g., U.S. Pat. No. 5,861,380 incorporated herein by reference in its entirety). U.S. Pat. No. 5,041,438, incorporated herein by reference in its entirety, reports that certain benzodiazepine compounds are useful as anti-retroviral agents.

Despite the attention benzodiazepine compounds have drawn, it will become apparent from the description below, that the present invention provides novel benzodiazepine compounds and related compounds and methods of using the novel compounds, as well as known compounds, for treating a variety of diseases.

Benzodiazepine compounds are known to bind to benzodiazepine receptors in the central nervous system (CNS) and thus have been used to treat various CNS disorders including anxiety and epilepsy. Peripheral benzodiazepine receptors have also been identified, which receptors may incidentally also be present in the CNS. The present invention demonstrates that benzodiazepines and related compounds have pro-apoptotic and cytotoxic properties useful in the treatment of transformed cells grown in tissue culture. The route of action of these compounds is not through the previously identified benzodiazepine receptors.

Experiments conducted during the development of the present invention have identified novel biological targets for benzodiazepine compounds and related compounds (some of which are related by their ability to bind cellular target molecules rather than their homology to the overall chemical structure of benzodiazepine compounds). In particular, the present invention provides compounds that interact, directly or indirectly, with particular mitochondrial proteins to elicit the desired biological effects.

Thus, in some embodiments, the present invention provides a number of novel compounds and previously known compounds directed against novel cellular targets to achieve desired biological results. In other embodiments, the present invention provides methods for using such compounds to regulate biological processes. The present invention also provides drug-screening methods to identify and optimize compounds. The present invention further provides diagnostic markers for identifying diseases and conditions, for monitoring treatment regimens, and/or for identifying optimal therapeutic courses of action. These and other research and therapeutic utilities are described below.

DETAILED DESCRIPTION OF THE INVENTION

The present invention provides novel chemical compounds, methods for their discovery, and their therapeutic use. In particular, the present invention provides benzodiazepine derivatives and related compounds and methods of using benzodiazepine derivatives and related compounds as therapeutic agents to treat a number of conditions associated with the faulty regulation of the processes of programmed cell death, autoimmunity, inflammation, and hyperproliferation, and the like.

Exemplary compositions and methods of the present invention are described in more detail in the following sections: I. Modulators of Cell Death; II. Modulators of Cell Growth and Proliferation; III. Expression Analysis of Treated Cells; IV. Exemplary Compounds; V. Pharmaceutical compositions, formulations, and exemplary administration routes and dosing considerations; VI. Drug screens; and VII. Therapeutic Applications.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Modulators of Cell Death

In preferred embodiments, the present invention regulates apoptosis through the exposure of cells to compounds. The effect of compounds can be measured by detecting any number of cellular changes. Cell death may be assayed as described herein and in the art. In preferred embodiments, cell lines are maintained under appropriate cell culturing conditions (e.g., gas ($CO_2$), temperature and media) for an appropriate period of time to attain exponential proliferation without density dependent constraints. Cell number and or viability are measured using standard techniques, such as trypan blue exclusion/hemo-cytometry, or MTT dye conversion assay. Alternatively, the cell may be analyzed for the expression of genes or gene products associated with aberrations in apoptosis or necrosis.

In preferred embodiments, exposing the present invention to a cell induces apoptosis. In some embodiments, the present invention causes an initial increase in cellular ROS levels (e.g., $O_2^-$). In further embodiments, exposure of the compounds of the present invention to a cell causes an increase in cellular $O_2^-$ levels. In still further embodiments, the increase in cellular $O_2^-$ levels resulting from the compounds of the present invention is detectable with a redox-sensitive agent that reacts specifically with $O_2^-$ (e.g., dihyroethedium (DHE)).

In other embodiments, increased cellular $O_2^-$ levels resulting from compounds of the present invention diminish after a period of time (e.g., 10 minutes). In other embodiments, increased cellular $O_2^-$ levels resulting from the compounds of the present invention diminish after a period of time and increase again at a later time (e.g., 10 hours). In further embodiments, increased cellular $O_2^-$ levels resulting from the compounds of the present invention diminish at 1 hour and increase again after 4 hours. In preferred embodiments, an early increase in cellular $O_2^-$ levels, followed by a diminishing in cellular $O_2^-$ levels, followed by another increase in cellular $O_2^-$ levels resulting from the compounds of the present invention is due to different cellular processes (e.g., bimodal cellular mechanisms).

In some embodiments, the present invention causes a collapse of a cell's mitochondrial $\Delta\Psi_m$. In preferred embodiments, a collapse of a cell's mitochondrial $\Delta\Psi_m$ resulting from the present invention is detectable with a mitochondria-selective potentiometric probe (e.g., $DiOC_6$). In further embodiments, a collapse of a cell's mitochondrial $\Delta\Psi_m$ resulting from the present invention occurs after an initial increase in cellular $O_2^-$ levels.

In some embodiments, the present invention enables caspace activation. In other embodiments, the present invention causes the release of cytochrome c from mitochondria. In further embodiments, the present invention alters cystolic cytochrome c levels. In still other embodiments, altered cystolic cytochrome c levels resulting from the present invention are detectable with immunoblotting cytosolic fractions. In preferred embodiments, diminished cystolic cytochrome c levels resulting from the present invention are detectable after a period of time (e.g., 10 hours). In further preferred embodiments, diminished cystolic cytochrome c levels resulting from the present invention are detectable after 5 hours.

In other embodiments, the present invention causes the opening of the mitochondrial PT pore. In preferred embodiments, the cellular release of cytochrome c resulting from the present invention is consistent with a collapse of mitochondrial $\Delta\Psi_m$. In still further preferred embodiments, the present invention causes an increase in cellular $O_2^-$ levels after a mitochondrial $\Delta\Psi_m$ collapse and a release of cytochrome c. In further preferred embodiments, a rise in cellular $O_2^-$ levels is caused by a mitochondrial $\Delta\Psi_m$ collapse and release of cytochrome c resulting from the present invention.

In other embodiments, the present invention causes cellular caspase activation. In preferred embodiments, caspase activation resulting from the present invention is measurable with a pan-caspase sensitive fluorescent substrate (e.g., FAM-VAD-fmk). In still further embodiments, caspase activation resulting from the present invention tracks with a collapse of mitochondrial $\Delta\Psi_m$. In other embodiments, the present invention causes an appearance of hypodiploid DNA. In preferred embodiments, an appearance of hypodiploid DNA resulting from the present invention is slightly delayed with respect to caspase activation.

In some embodiments, the molecular target for the present invention is found within mitochondria. In further embodiments, the molecular target of the present invention involves the mitochondrial ATPase. The primary sources of cellular ROS include redox enzymes and the mitochondrial respiratory chain (hereinafter MRC). In preferred embodiments, cytochrome c oxidase (complex IV of the MRC) inhibitors (e.g., $NaN_3$) preclude a present invention dependent increase in cellular ROS levels. In other preferred embodiments, the ubiquinol-cytochrome c reductase component of MRC complex III inhibitors (e.g., FK506) preclude a present invention dependent increase in ROS levels.

In some embodiments, an increase in cellular ROS levels due to the compounds of the present invention result from the binding of the compounds of the present invention to a target within mitochondria. In preferred embodiments, the compounds of the present invention oxidizes 2',7'-dichlorodihydrofluorescin (hereinafter DCF) diacetate to DCF. DCF is a redox-active species capable of generating ROS. In further embodiments, the rate of DCF production resulting from the present invention increases after a lag period.

Antimycin A generates $O_2^-$ by inhibiting ubiquinol-cytochrome c reductase. In preferred embodiments, the present invention increases the rate of ROS production in an equivalent manner to antimycin A. In further embodiments, the present invention increases the rate of ROS production in an equivalent manner to antimycin A under aerobic conditions supporting state 3 respiration. In further embodiments, the compounds of the present invention do not directly target the MPT pore. In additional embodiments, the compounds of the present invention do not generate substantial ROS in the subcellular S15 fraction (e.g., cytosol; microsomes). In even further embodiments, the compounds of the present invention do not stimulate ROS if mitochondria are in state 4 respiration.

MRC complexes I-III are the primary sources of ROS within mitochondria. In preferred embodiments, the primary source of an increase in cellular ROS levels resulting from the dependent invention emanates from these complexes as a result of inhibiting the mitochondrial $F_1F_0$-ATPase. Indeed, in still further embodiments, the present invention inhibits mitochondrial ATPase activity of bovine sub-mitochondrial particles (hereinafter SMPs). In particularly preferred embodiments, the compounds of the present invention bind to the OSCP component of the mitochondrial $F_1F_0$-ATPase.

In some embodiments, the compounds of the present invention have the structure:

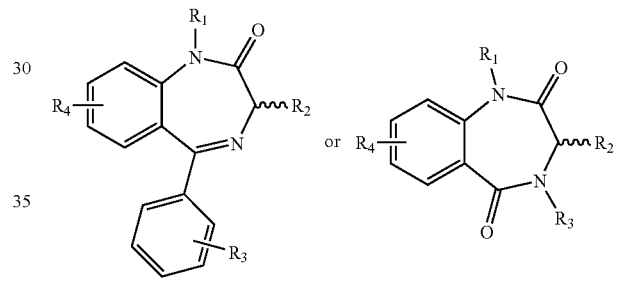

or its enantiomer, wherein, $R_1$ is aliphatic or aryl; $R_2$ is aliphatic, aryl, —$NH_2$, —HC(=O)—$R_5$, or a moiety that participates in hydrogen bond formation, wherein $R_5$ is aryl, heterocyclic, —$R_6$—NH—C(=O)—$R_7$ or —$R_6$—C(=O)—NH—$R_7$, wherein $R_6$ is an aliphatic linker of 1-6 carbons and $R_7$ is aliphatic, aryl, or heterocyclic; and each of $R_3$ and $R_4$ is independently hydrogen, hydroxy, alkoxy, halo, amino, lower-alkyl-substituted-amino, acylamino, hydroxyamino, an aliphatic group having 1-8 carbons and 1-20 hydrogens, aryl, or heteroaryl; or a pharmaceutically acceptable salt, prodrug or derivative thereof. In some preferred embodiments, where R3 is a hydroxyl group, one or more additional positions on the ring containing R3 includes a chemical group (e.g., an alkyl chain) that protects the hydroxyl group from metabolism in vivo.

In certain embodiments, the compounds of the present invention may have a hydroxyl group at the C'4 position and an aromatic ring. In preferred embodiments, compounds of the present invention cause an increase in cellular ROS levels as a result of a hydroxyl group at the C'4 position and an aromatic ring. In further embodiments, the potency of the present invention in cell based assays correlates with ATPase inhibition experiments using SMPs. Indeed, in preferred embodiments, the present invention significantly inhibits mitochondrial ATPase activity in comparison to cytotoxic (80 μM) concentrations of general benzodiazepines and PBR ligands (e.g., PK11195 and 4-chlorodiazepam) that do not significantly inhibit mitochondrial ATPase activity. As such, in preferred embodiments, the molecular target of the present invention is the mitochondrial ATPase.

Oligomycin is a macrolide natural product that binds to the mitochondrial $F_1F_0$-ATPase, induces a state 3 to 4 transition, and as a result, generates ROS (e.g., $O_2^-$). In preferred embodiments, the present invention binds the OSCP component of the mitochondrial $F_1F_0$-ATPase. In certain embodiments, screening assays of the present invention permit detection of binding partners of the OSCP. OSCP is an intrinsically fluorescent protein. In certain embodiments, titrating a solution of test compounds of the present invention into an *E. Coli* sample overexpressed with OSCP results in quenching of the intrinsic OSCP fluorescence. In other embodiments, fluorescent or radioactive test compounds can be used in direct binding assays. In other embodiments, competition binding experiments can be conducted. In this type of assay, test compounds are assessed for their ability to compete with Bz-423 for binding to the OSCP. In some embodiments, the compounds of the present invention cause a reduced increase in cellular ROS levels and reduced apoptosis in cells through regulation of the OSCP gene (e.g., altering expression of the OSCP gene). In further embodiments, the present invention functions by altering the molecular motions of the ATPase motor.

II. Modulators of Cellular Proliferation and Cell Growth

In some embodiments, the compounds and methods of the present invention causes decreased cellular proliferation. In other embodiments, the compounds and methods of the present invention causes decreased cellular proliferation and apoptosis. For example, cell culture cytotoxicity assays conducted during the development of the present invention demonstrated that the compounds and methods of the present invention prevents cell growth after an extended period in culture (e.g., 3 days).

III. Expression Analysis of Treated Cells

In some embodiments, induced cell death is not dependent upon new protein synthesis. Treatment of cells with cyclohexamide inhibits new protein synthesis. In some embodiments, cells treated with cyclohexamide and the compounds of the present invention enter apoptosis.

During the development of the present invention, an expression profile was generated to identify those genes that are differentially expressed in treated and untreated cells. This profile provides a gene expression fingerprint of cells induced by the compounds of the present invention. This fingerprint identifies genes that are upregulated and down-regulated in response to the compounds of the present invention and identifies such genes are diagnostic markers for drug screening and for monitoring therapeutic effects of the compounds. The genes also provide targets for regulation to mimic the effects of the compounds of the present invention. Data from an expression analysis for genes up-regulated in the presence of Bz-423 is presented in FIG. 4A. Data from an expression analysis for genes down-regulated in the presence of Bz-423 is presented in FIG. 4B. Data from an expression analysis for genes up-regulated in the presence of Bz-OMe is presented in FIG. 4C. Data from an expression analysis for genes down-regulated in the presence of Bz-OMe is presented in FIG. 4D.

For example, an analysis of the expression profile provides ornithine decarboxylase antizyme 1 (OAZ1) as a novel therapeutic agent. OAZ1 is an important regulatory protein that controls the synthesis and transport into cells of polyamines, including putrescine, spermidine and spermine. The synthesis of polyamines in cells involves several enzymatic steps, however ornithine decarboxylase is the enzyme that principally regulates this process. By inhibiting the polyamine transporter located in the plasma membrane and by targeting ornithine decarboxylase for proteolytic degradation, OAZ1 reduces polyamine levels in cells. Polyamines are essential for the survival and growth of cells. Abnormal accumulation of polyamines contributes to tumor induction, cancer growth and metastasis. Inhibitors of polyamine biosynthesis, and specifically one molecule identified as difluoromethylornithine (DFMO), are in clinical trials to confirm their anticarcinogenic and therapeutic potential. In preferred embodiments of the present invention, OAZ1 is induced to a level 16-fold above the level of control cells in cells treated with the compounds of the present invention. Any method, direct or indirect, for inducing OAZ1 levels is contemplated by the present invention (e.g., treatment with compounds of the present invention, gene therapy, etc.).

OAZ1 is an important regulator of polyamine metabolism and functions to decrease polyamine levels by acting as an inhibitor of ornithine decarboxylase (ODC), a mitochondrial enzyme that controls the rate-limiting step of polyamine biosynthesis. After inhibition with antizyme, ODC is targeted for proteosomal degradation. Polyamines are intimately involved in cellular stability and required for cell proliferation. Inhibiting polyamine synthesis suppresses proliferation. As such, in still further embodiments, ODC expression or activity is decreased (e.g., using siRNA, antisense oligonucleotides, gene therapy, known or later identified inhibitors, the compounds of the present invention, etc.) to elicit the desired biological effect.

Antizyme 1 expression is regulated transcriptionally and at the post-transcriptional level. Post-transcriptional regulation plays a particularly important role in the regulation of this gene product and occurs by a unique translational frameshift that depends on either polymanes (through a negative-feedback loop) or agmatine, another metabolite of arginine. ODC activity leves may be obtained by quanifying the conversion of ornithine to putrescine using $^3$H-ornithine. In some embodiments, treating cells with the compounds of the present invention significantly reduces ODC activity in a dose-dependant fashion. In still further embodiments, a reduction in ODC activity is paralleled by a decrease in ODC protein levels measured under similar conditions. Cells pre-incubated with MnTBAP decrease ROS levels. In some embodiments, cells pre-incubated with MnTBAP that are exposed to the compounds of the present invention display reversed inhibition of ODC.

In preferred embodiments, cells treated with high levels (e.g., >10 μM) of the compounds of the present invention generate sufficient amounts of ROS that are not detoxified by cellular anti-oxidants, and result in apoptosis within a short time period (e.g., 18 h). In preferred embodiments, cells treated with lower levels (e.g., <10 μM) of the compounds of the present invention induce a reduced ROS response that is insufficient to trigger apoptosis, but is capable of inhibiting ODC or otherwise blocking cellular proliferation. In other embodiments, a derivative of the compounds of the present invention in which the phenolic hydroxyl is replaced by Cl or $OCH_3$ is minimally cytotoxic, generates a small ROS response in cells, binds less tightly to the OSCP, and inhibits ODC activity. In still other embodiments, cells treated with a derivative of the compounds of the present invention in which the phenolic hydroxyl is replaced by Cl experience reduced proliferation to a similar extent as to the unmodified compounds. As such, in preferred embodiments, the antiproliferative effects are obtained using chemical derivatives of the compounds of the present invention that block proliferation without inducing apoptosis.

In response to antigenic or mitogenic stimulation, lymphocytes secrete protein mediators, one of which is named migration inhibitory factor (MIF) for its ability to prevent the migration of macrophages in vitro. MIF may be an anti-tumor agent. In addition, the ability of MIF to prevent the migration of macrophages may be exploited for treating wounds. MIF may alter the immune response to different antigens. MIF links chemical and immunological detoxification systems. MIF was induced approximately 10-fold by Bz-423. Thus, the present invention contemplates the use of MIF as a target of the compounds of the present invention.

Profilin is induced at high levels in cell treated with the present invention. Profilin binds to actin monomers and interacts with several proteins and phosphoinositides, linking signaling pathways to the cytoskeleton. Profilin can sequester actin monomers, increase exchange of ATP for ADP on actin, and increase the rate of actin filament turnover. A comparison between several different tumorigenic cancer cell lines with nontumorigenic lines show consistently lower profilin 1 levels in tumor cells. Transfection of profilin 1 cDNA into CAL51 breast cancer cells raised the profilin 1 level, had a prominent effect on cell growth, and suppressed tumorigenicity of the overexpressing cell clones in nude mice. Therefore, induction of profilin 1 (e.g., by the compounds of the present invention or otherwise) may suppress the tumorigenesis of cancer cells.

Interferon regulatory factor 4 (IRF-4) is induced at higher than normal levels in cells treated with the compounds of the present invention. IRF-4 is a lymphoid/myeloid-restricted member of the IRF transcription factor family that plays an essential role in the homeostasis and function of mature lymphocytes. IRF-4 expression is regulated in resting primary T cells and is transiently induced at the mRNA and protein levels after activation by stimuli such as TCR cross-linking or treatment with phorbol ester and calcium ionophore (PMA/ionomycin). Stable expression of IRF-4 in Jurkat cells leads to a strong enhancement in the synthesis of interleukin (IL)-2, IL-4, IL-10, and IL-13. IRF-4 represents one of the lymphoid-specific components that control the ability of T lymphocytes to produce a distinctive array of cytokines. In Abelson-transformed pro-B cell lines, enforced expression of IRF4 is sufficient to induce germline Igk transcription. The action of the compounds of the present invention to induce IRF4 may account for its affects on autoimmune disease in B and T cell dominant processes as well as for its ability to influence the survival of neoplastic B cell clones.

In preferred embodiments, cell death-regulatory protein GRIM19 is induced at higher than normal levels in cells treated with the compounds of the present invention. The importance of the interferon (IFN) pathway in cell growth suppression is known. Studies have shown that a combination of IFN and all-trans retinoic acid inhibits cell growth in vitro and in vivo more potently than either agent alone. The specific genes that play a role in IFN/RA-induced cell death were identified by an antisense knockout approach, and called GRIM genes. GRIM19 is a novel cell death-associated gene that is not included in any of the known death gene categories. This gene encodes a 144-aa protein that localizes to the nucleus. Overexpression of GRIM19 enhances caspase-9 activity and apoptotic cell death in response to IFN/RA treatment. GRIM19 is located in the 19p13.2 region of the human chromosome essential for prostate tumor suppression, signifying that the protein may be a novel tumor suppressor. The induction of GRIM19 by the compounds of the present invention may result in anti-tumor effects.

IV. Exemplary Compounds

Exemplary compounds of the present invention are provided below.

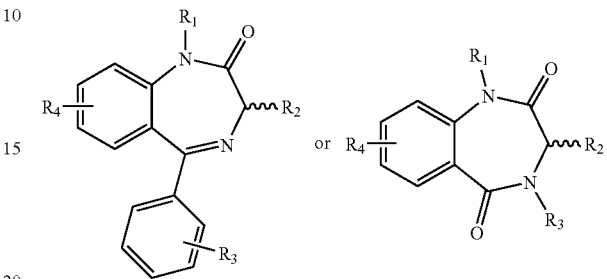

or its enantiomer, wherein, $R_1$ is aliphatic or aryl; $R_2$ is aliphatic, aryl, $-NH_2$, $-NHC(=O)-R_5$; or a moiety that participates in hydrogen bonding, wherein $R_5$ is aryl, heterocyclic, $-R_6-NH-C(=O)-R_7$ or $-R_6-C(=O)-NH-R_7$, wherein $R_6$ is an aliphatic linker of 1-6 carbons and $R_7$ is aliphatic, aryl, or heterocyclic, each of $R_3$ and $R_4$ is independently a hydroxy, alkoxy, halo, amino, lower-alkyl-substituted-amino, acetylamino, hydroxyamino, an aliphatic group having 1-8 carbons and 1-20 hydrogens, aryl, or heterocyclic; or a pharmaceutically acceptable salt, prodrug or derivative thereof.

In the above structures, $R_1$ is a hydrocarbyl group of 1-20 carbons and 1-20 hydrogens. Preferably, $R_1$ has 1-15 carbons, and more preferably, has 1-12 carbons. Preferably, $R_1$ has 1-12 hydrogens, and more preferably, 1-10 hydrogens. Thus $R_1$ can be an aliphatic group or an aryl group.

The term "aliphatic" represents the groups commonly known as alkyl, alkenyl, alkynyl, alicyclic. The term "aryl" as used herein represents a single aromatic ring such as a phenyl ring, or two or more aromatic rings that are connected to each other (e.g., bisphenyl) or fused together (e.g., naphthalene or anthracene). The aryl group can be optionally substituted with a lower aliphatic group (e.g., $C_1$-$C_4$ alkyl, alkenyl, alkynyl, or $C_3$-$C_6$ alicyclic). Additionally, the aliphatic and aryl groups can be further substituted by one or more functional groups such as $-NH_2$, $-NHCOCH_3$, $-OH$, lower alkoxy ($C_1$-$C_4$), halo ($-F$, $-Cl$, $-Br$, or $-I$). It is preferable that $R_1$ is primarily a nonpolar moiety.

In the above structures, $R_2$ can be aliphatic, aryl, $-NH_2$, $-NHC(=O)-R_5$, or a moiety that participates in hydrogen bonding, wherein $R_5$, is aryl, heterocyclic, $R_6-NH-C(=O)-R_7$ or $-R_6-C(=O)-NH-R_7$, wherein $R_6$ is an aliphatic linker of 1-6 carbons and $R_7$ is an aliphatic, aryl, or heterocyclic. The terms "aliphatic" and "aryl" are as defined above.

The term "a moiety that participates in hydrogen bonding" as used herein represents a group that can accept or donate a proton to form a hydrogen bond thereby.

Some specific non-limiting examples of moieties that participate in hydrogen bonding include a fluoro, oxygen-containing and nitrogen-containing groups that are well-known in the art. Some examples of oxygen-containing groups that participate in hydrogen bonding include: hydroxy, lower alkoxy, lower carbonyl, lower carboxyl, lower ethers and phenolic groups. The qualifier "lower" as used herein refers to lower aliphatic groups ($C_1$-$C_4$) to which the respective oxygen-containing functional group is attached.

Thus, for example, the term "lower carbonyl" refers to inter alia, formaldehyde, acetaldehyde.

Some nonlimiting examples of nitrogen-containing groups that participate in hydrogen bond formation include amino and amido groups. Additionally, groups containing both an oxygen and a nitrogen atom can also participate in hydrogen bond formation. Examples of such groups include nitro, N-hydroxy and nitrous groups.

It is also possible that the hydrogen-bond acceptor in the present invention can be the Π electrons of an aromatic ring. However, the hydrogen bond participants of this invention do not include those groups containing metal atoms such as boron.

Further the hydrogen bonds formed within the scope of practicing this invention do not include those formed between two hydrogens, known as "dihydrogen bonds." (See, R. H. Crabtree, Science, 282:2000-2001 [1998], for further description of such dihydrogen bonds).

The term "heterocyclic" represents, for example, a 3-6 membered aromatic or nonaromatic ring containing one or more heteroatoms. The heteroatoms can be the same or different from each other. Preferably, at least one of the heteroatom's is nitrogen. Other heteroatoms that can be present on the heterocyclic ring include oxygen and sulfur.

Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfuir-containing heterocyclic rings include, but are not limited to, thiophene, benzothiophene, and parathiazine.

Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine.

Examples of heterocyclic rings containing two different heteroatoms include, but are not limited to, phenothiazine, morpholine, parathiazine, oxazine, oxazole, thiazine, and thiazole.

The heterocyclic ring is optionally further substituted with one or more groups selected from aliphatic, nitro, acetyl (i.e., —C(═O)—$CH_3$), or aryl groups.

Each of $R_3$ and $R_4$ can be independently a hydroxy, alkoxy, halo, amino, or substituted amino (such as lower-alkyl-substituted-amino, or acetylamino or hydroxyamino), or an aliphatic group having 1-8 carbons and 1-20 hydrogens. When each of $R_3$ and $R_4$ is an aliphatic group, it can be further substituted with one or more functional groups such as a hydroxy, alkoxy, halo, amino or substituted amino groups as described above. The terms "aliphatic" is defined above. Alternatively, each of $R_3$ and $R_4$ can be hydrogen.

It is well-known that many 1,4-benzodiazepines exist as optical isomers due to the chirality introduced into the heterocyclic ring at tile $C_3$ position. The optical isomers are sometimes described as L- or D-isomers in the literature. Alternatively, the isomers are also referred to as R- and S-enantiomorphs. For the sake of simplicity, these isomers are referred to as enantiomorphs or enantiomers. The 1,4-benzodiazepine compounds described herein include their enantiomeric forms as well as racemic mixtures. Thus, the usage "benzodiazepine or its enantiomers" herein refers to the benzodiazepine as described or depicted, including all its enantiomorphs as well as their racemic mixture.

From the above description, it is apparent that many specific examples are represented by the generic formulas presented above. Thus, in one example, $R_1$ is aliphatic, $R_2$ is aliphatic, whereas in another example, $R_1$ is aryl and $R_2$ is a moiety that participates in hydrogen bond formation. Alternatively, $R_1$ can be aliphatic, and $R_2$ can be an —NHC(═O)—$R_5$, or a moiety that participates in hydrogen bonding, wherein $R_5$ is aryl, heterocyclic, —$R_6$—NH—C(═O)—$R_7$ or —$R_6$—C(═O)—NH—$R_7$, wherein $R_6$ is an aliphatic linker of 1-6 carbons and $R_7$ is an aliphatic, aryl, or heterocyclic. A wide variety of sub combinations arising from selecting a particular group at each substituent position are possible and all such combinations are within the scope of this invention.

Further, it should be understood that the numerical ranges given throughout this disclosure should be construed as a flexible range that contemplates any possible subrange within that range. For example, the description of a group having the range of 1-10 carbons would also contemplate a group possessing a subrange of, for example, 1-3, 1-5, 1-8, or 2-3, 2-5, 2-8, 3-4, 3-5, 3-7, 3-9, 3-10, etc., carbons. Thus the range 1-10 should be understood to represent the outer boundaries of the range within which many possible subranges are clearly contemplated. Additional examples contemplating ranges in other contexts can be found throughout this disclosure wherein such ranges include analogous subranges within.

Some specific examples of the benzodiazepine compounds of this invention include:

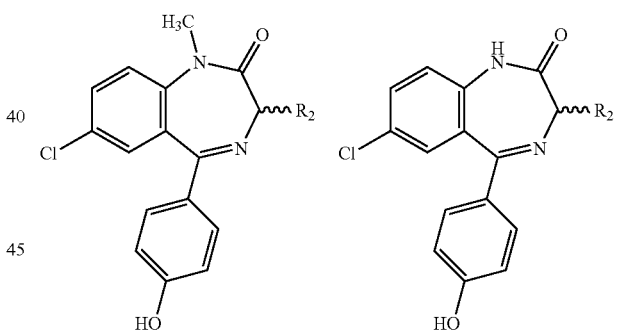

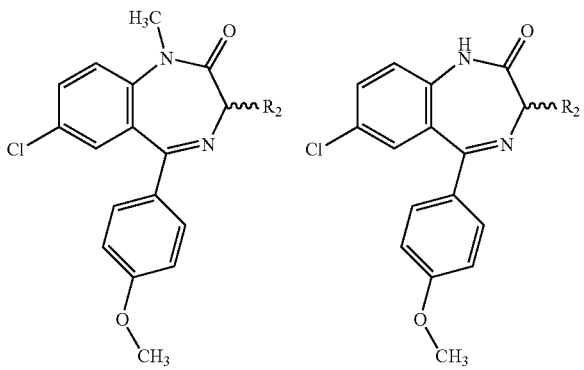

wherein $R_2$ is

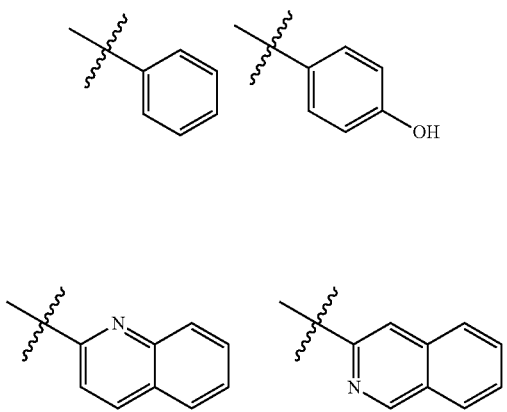

and dimethylphenyl (all isomers) and ditrifluoromethyl (all isomers).

The following compounds are also contemplated:

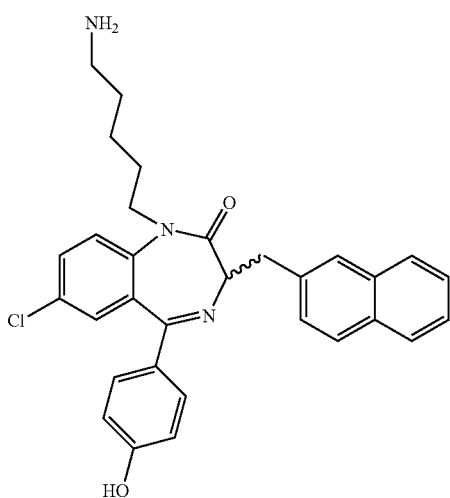

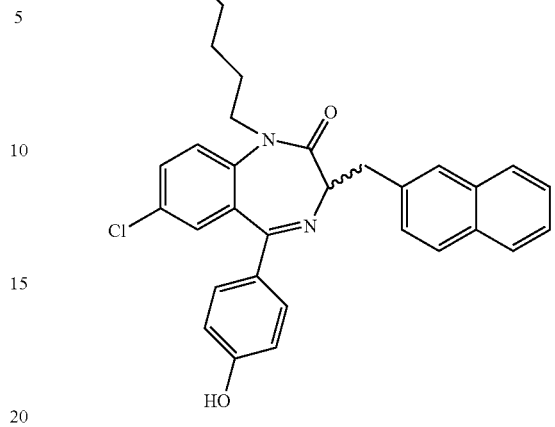

This invention also provides the compound Bz-423.

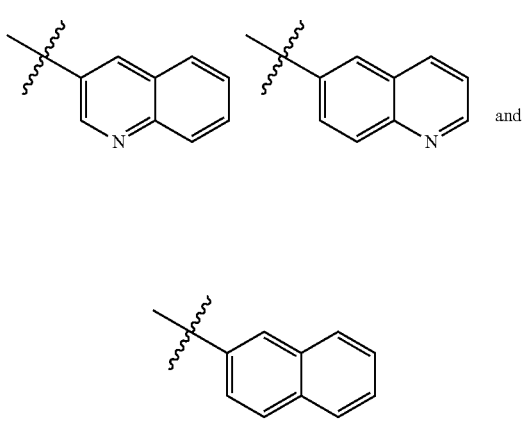

Bz-423 differs from benzodiazepines in clinical use by the presence of a hydrophobic substituent at C-3. This substitution renders binding to the peripheral benzodiazepine receptor ("PBR") weak ($K_d$ ca. 1 µM) and prevents binding to the central benzodiazepine receptor so that Bz-423 is not a sedative.

In some embodiments R2 is any chemical group that permits the compound to bind to OSCP. In some such embodiments, R2 comprises a hydrophobic aromatic group. In preferred embodiments R2 comprises a hydrophobic aromatic group larger than benzene (e.g., a benzene ring with non-hydrogen substituents, a moiety having two or more aromatic rings, a moiety with 7 or more carbon atoms, etc.).

Additional specific benzodiazepine derivative examples of the present invention include the following:

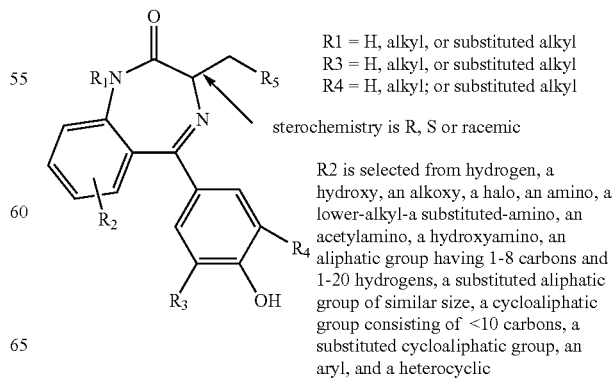

R1 = H, alkyl, or substituted alkyl
R3 = H, alkyl, or substituted alkyl
R4 = H, alkyl; or substituted alkyl sterochemistry is R, S or racemic R2 is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic -continued R5 = 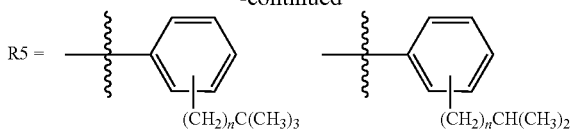

n = 0-5            n = 0-5

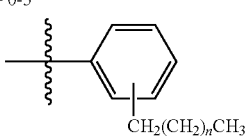

n = 0-5

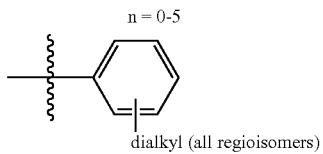

dialkyl (all regioisomers)

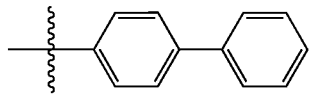

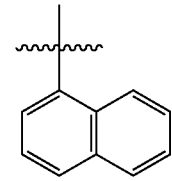

difluoromethyl (all regioisomers)

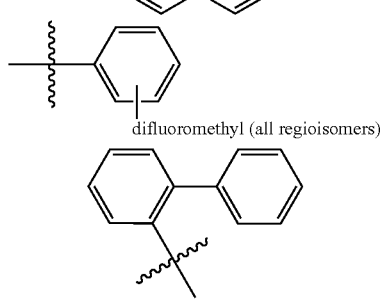

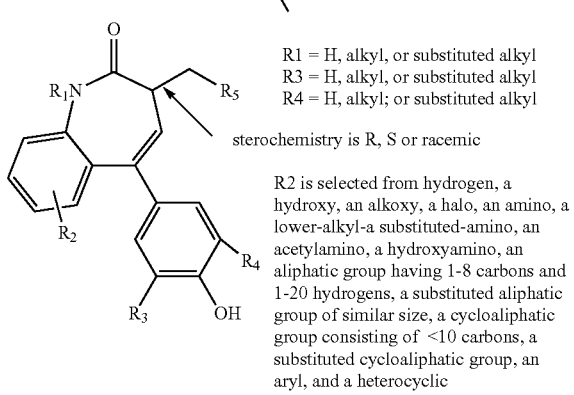

R1 = H, alkyl, or substituted alkyl
R3 = H, alkyl, or substituted alkyl
R4 = H, alkyl; or substituted alkyl sterochemistry is R, S or racemic R2 is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic R5 = 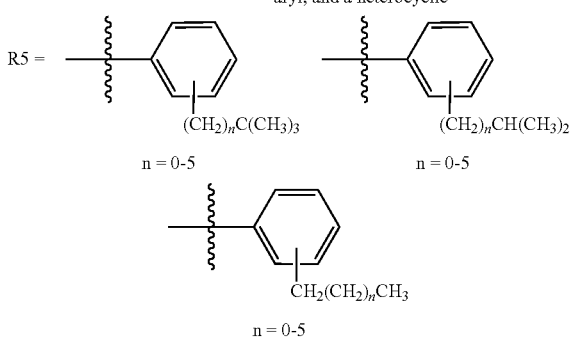

n = 0-5            n = 0-5

-continued

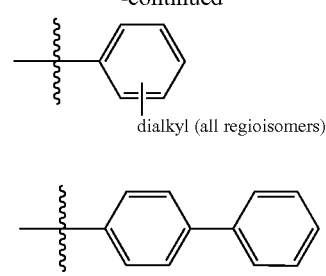

dialkyl (all regioisomers)

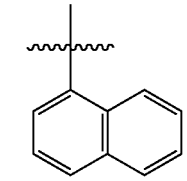

difluoromethyl (all regioisomers)

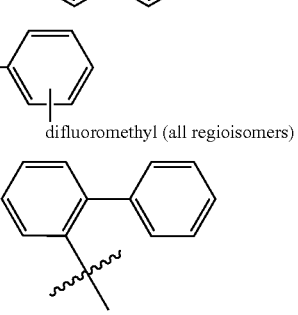

R2 = H, alkyl, or substituted alkyl
R3 = H, alkyl, or substituted alkyl

R1 is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic R4 = 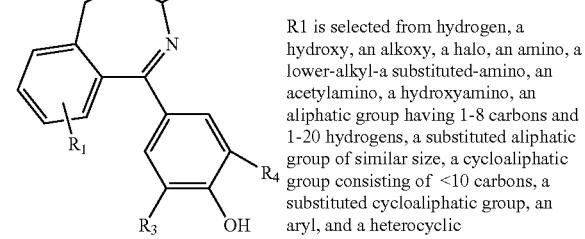

n = 0-5            n = 0-5

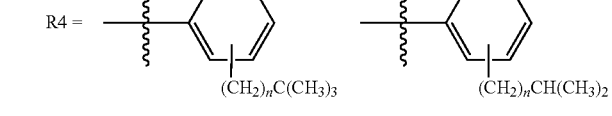

n = 0-5

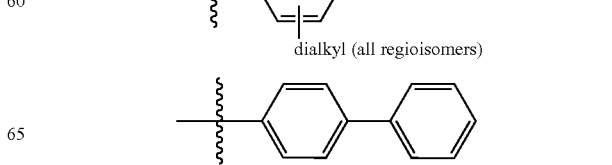

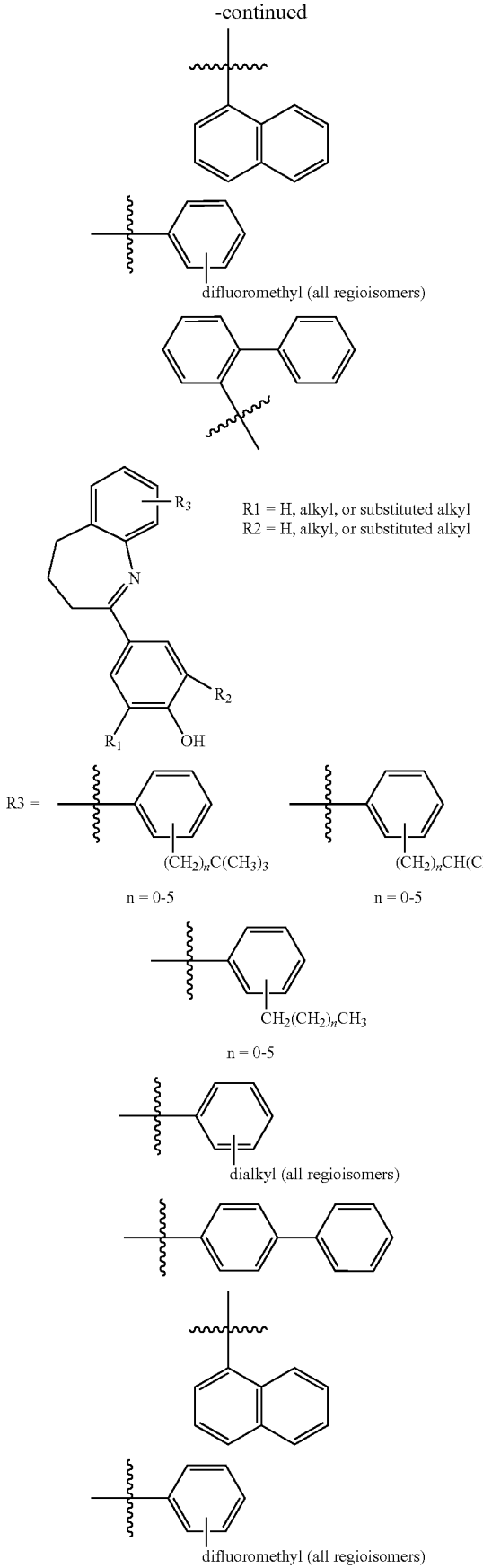
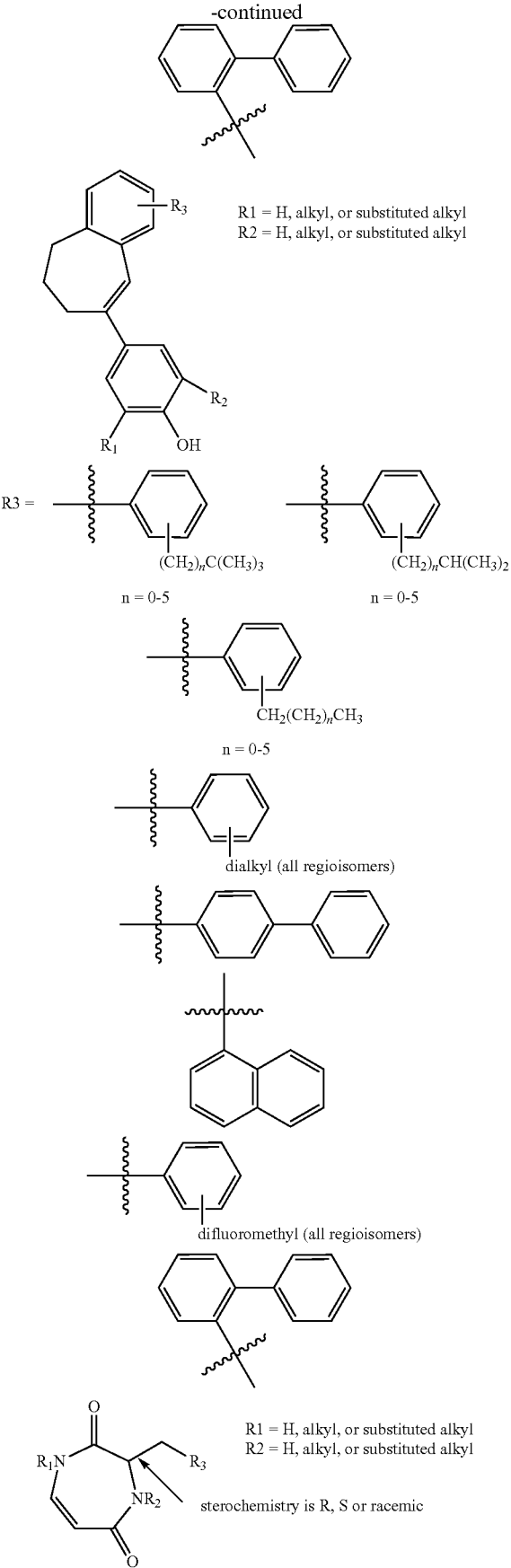

-continued

R3 = 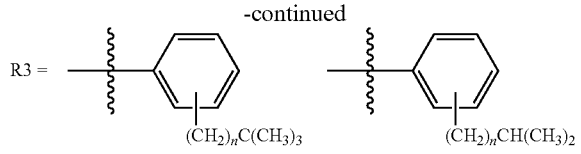

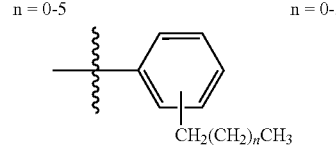

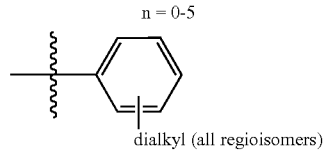
dialkyl (all regioisomers)

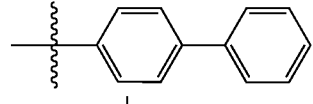

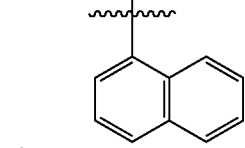
difluoromethyl (all regioisomers)

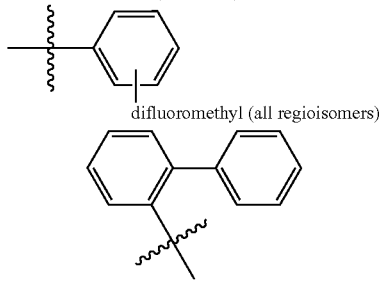

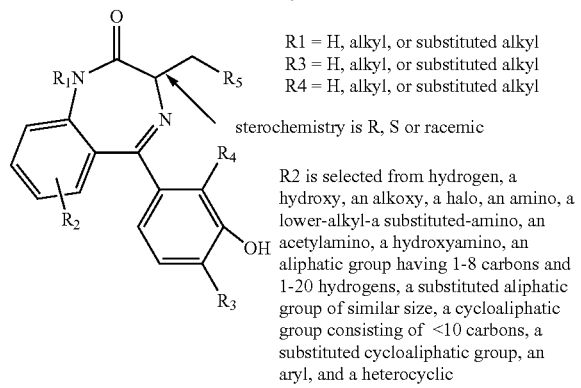

R1 = H, alkyl, or substituted alkyl
R3 = H, alkyl, or substituted alkyl
R4 = H, alkyl, or substituted alkyl sterochemistry is R, S or racemic R2 is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic R5 = 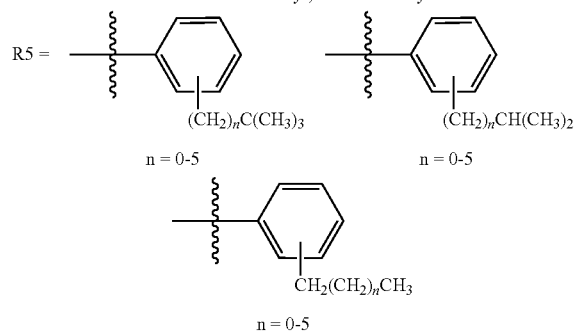

-continued

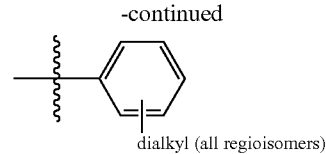

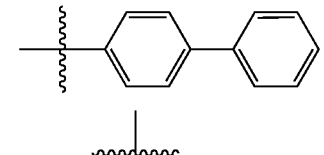
dialkyl (all regioisomers)

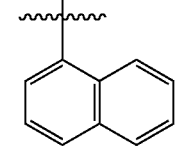

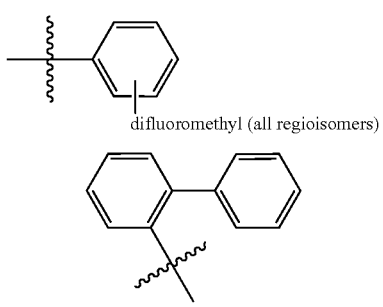
difluoromethyl (all regioisomers)

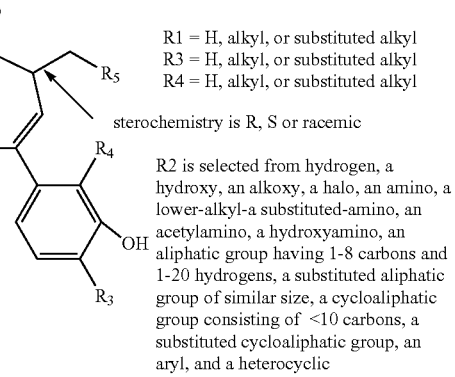

R1 = H, alkyl, or substituted alkyl
R3 = H, alkyl, or substituted alkyl
R4 = H, alkyl, or substituted alkyl sterochemistry is R, S or racemic R2 is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic R5 = 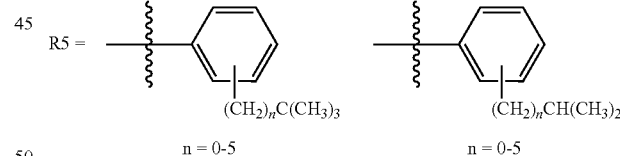

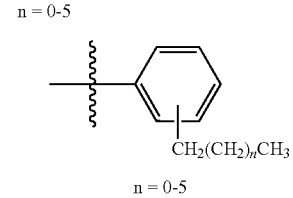

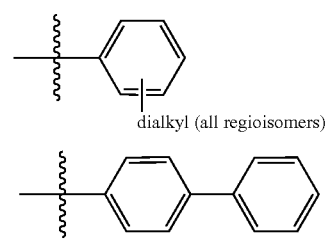

-continued

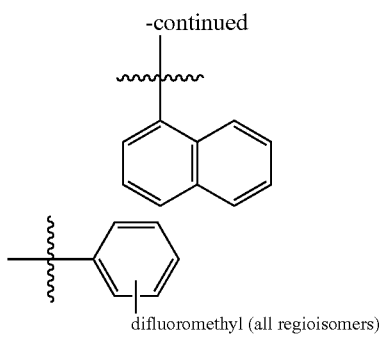

difluoromethyl (all regioisomers)

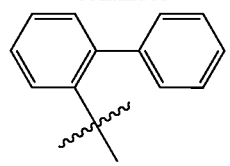

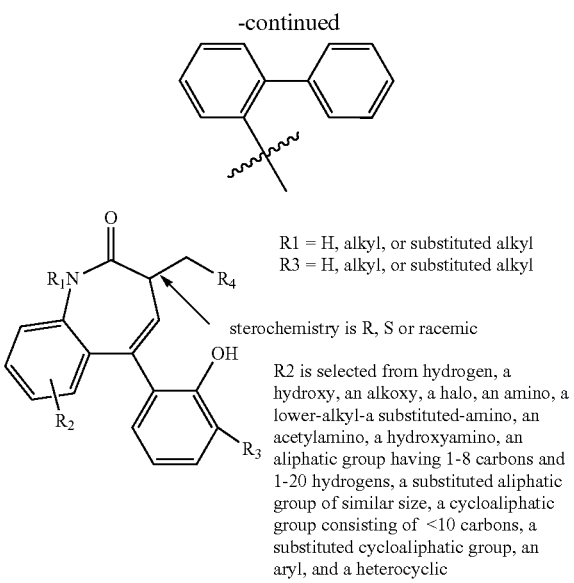

R1 = H, alkyl, or substituted alkyl
R3 = H, alkyl, or substituted alkyl sterochemistry is R, S or racemic R2 is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic

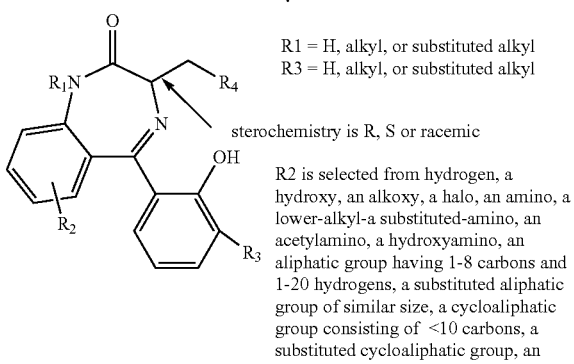

R1 = H, alkyl, or substituted alkyl
R3 = H, alkyl, or substituted alkyl sterochemistry is R, S or racemic R2 is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic R4 = 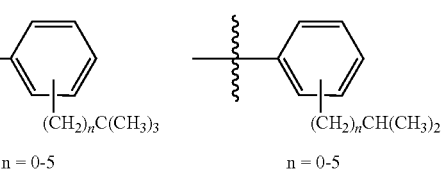

n = 0-5   n = 0-5

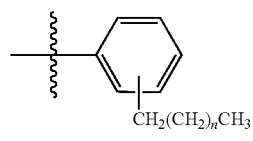

n = 0-5

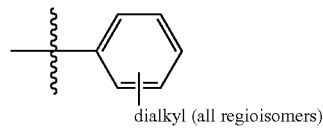

dialkyl (all regioisomers)

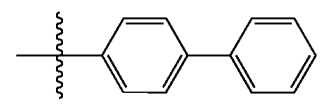

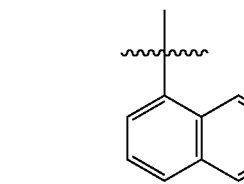

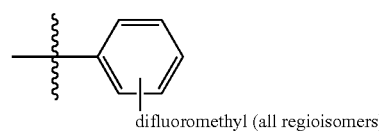

difluoromethyl (all regioisomers)

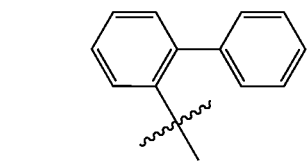

R4 = 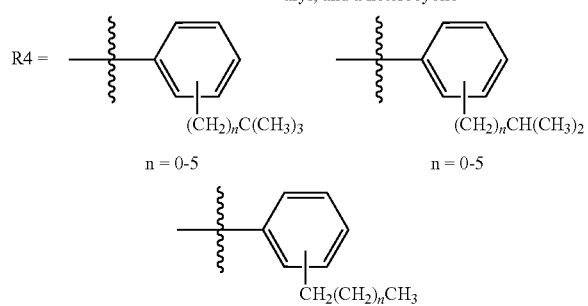

n = 0-5   n = 0-5

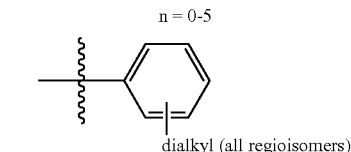

n = 0-5

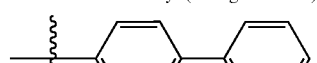

dialkyl (all regioisomers)

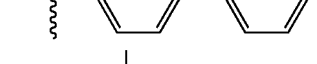

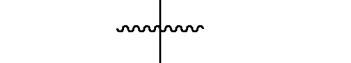

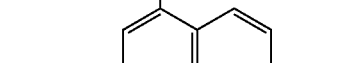

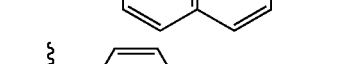

difluoromethyl (all regioisomers)

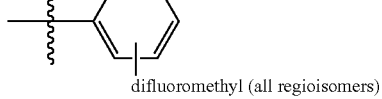

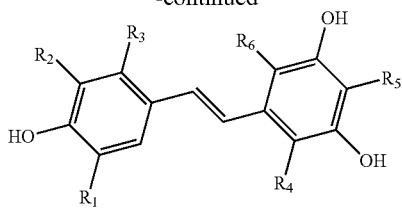

R1 is H or hydroxy
Each of R2 through R6 may be the same or different and is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic

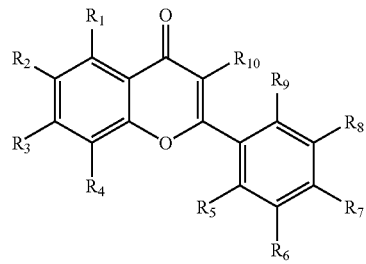

Each of R1 through R10 may be the same or different and is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic

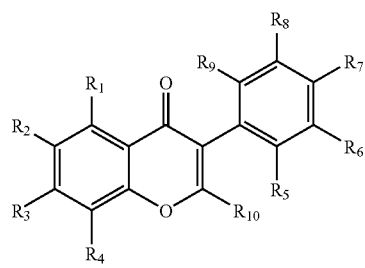

Each of R1 through R10 may be the same or different and is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic

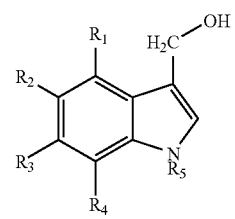

Each of R1 through R10 may be the same or different and is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic

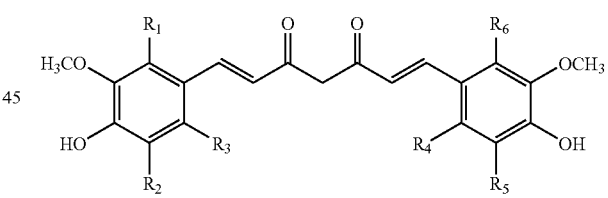

Each of R1 through R6 may be the same or different and is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic

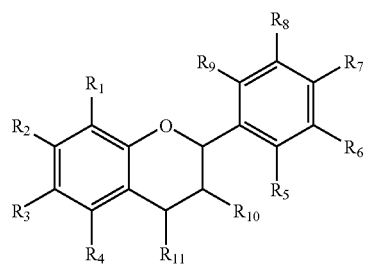

Each of R1 through R11 may be the same or different and is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic lansoprazole 45
-continued radicicol R1 = H, alkyl, or substituted alkyl
R4 = H, alkyl, or substituted alkyl sterochemistry is R, S or racemic R2 is selected from hydrogen, a hydroxy, an alkoxy, a halo, an amino, a lower-alkyl-a substituted-amino, an acetylamino, a hydroxyamino, an aliphatic group having 1-8 carbons and 1-20 hydrogens, a substituted aliphatic group of similar size, a cycloaliphatic group consisting of <10 carbons, a substituted cycloaliphatic group, an aryl, and a heterocyclic

R3 =

$(CH_2)_n C(CH_3)_3$
n = 0-5

$(CH_2)_n CH(CH_3)_2$
n = 0-5

$CH_2(CH_2)_n CH_3$
n = 0-5 dialkyl (all regioisomers)

difluoromethyl (all regioisomers)

46
-continued wherein $R_1$ is selected from napthalalanine; phenol; 1-Napthalenol; 2-Napthalenol;

and quinolines.

A composition comprising the following formula:

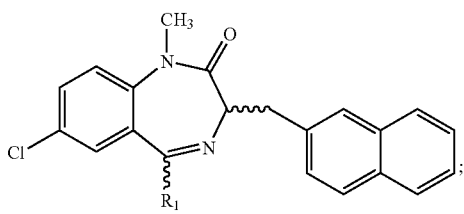

wherein $R_1$ is selected from:

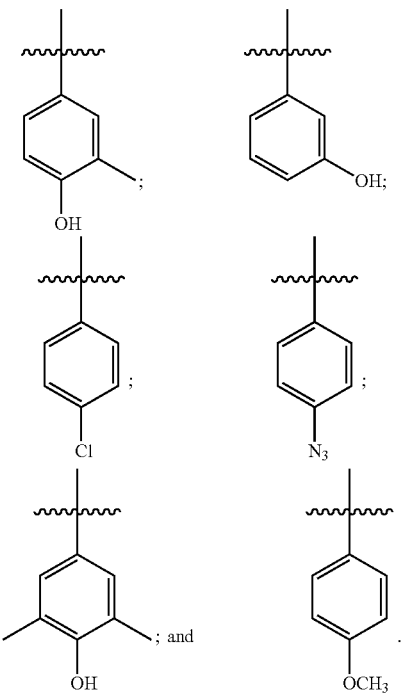

The stereochemistry of all derivatives embodied in the present invention is R, S, or racemic.

In summary, a large number of benzodiazepine compounds and related compounds are presented herein. Any one or more of these compounds can be used to treat a variety of dysregulatory disorders related to cellular death as described elsewhere herein. The above-described compounds can also be used in drug screening assays and other diagnostic methods.

V. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat a variety of conditions associated with dysregulation of cell death, aberrant cell growth and hyperproliferation.

In addition, the compounds are also useful for preparing medicaments for treating other disorders wherein the effectiveness of the compounds are known or predicted. Such disorders include, but are not limited to, neurological (e.g., epilepsy) or neuromuscular disorders. The methods and techniques for preparing medicaments of a compound are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent (e.g., benzodiazepine derivative), as defined above, together with a solid support or alternatively, together with one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In preferred embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g. active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In preferred embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in an known manner. This phase typically comprises an lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer a therapeutic agents (e.g., benzodiazepine derivatives) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified herein as effective for their intended purpose can be administered to subjects or individuals susceptible to or at risk of developing pathological growth of target cells and condition correlated with this. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent. One example of an animal model is MLR/MpJ-lpr/lpr ("MLR-lpr") (available from Jackson Laboratories, Bal Harbor, Me.). MLR-lpr mice develop systemic autoimmune disease. Alternatively, other animal models can be developed by inducing tumor growth, for example, by subcutaneously inoculating nude mice with about $10^5$ to about $10^9$ hyperproliferative, cancer or target cells as defined herein. When the tumor is established, the compounds described herein are administered, for example, by subcutaneous injection around the tumor. Tumor measurements to determine reduction of tumor size are made in two dimensions using venier calipers twice a week. Other animal models may also be employed as appropriate. Such animal models for the above-described diseases and conditions are well-known in the art.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary co-administration routes and dosing considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is cancer, the additional agent can be a chemotherapeutic agent or radiation. When the condition being treated is an autoimmune disorder, the additional agent can be an immunosuppressant or an anti-inflammatory agent. When the condition being treated is chronic inflammation, the additional agent can be an anti-inflammatory agent. The additional agents to be co-administered, such as, anticancer, immunosuppressant, anti-inflammatory, and can be any of the well-known agents in the art, including, but not limited to, those that are currently in clinical use. The determination of appropriate type and dosage of radiation treatment is also within the skill in the art or can be determined with relative ease.

Treatment of the various conditions associated with abnormal apoptosis is generally limited by the following two major factors: (1) the development of drug resistance and (2) the toxicity of known therapeutic agents. In certain cancers, for example, resistance to chemicals and radiation therapy has been shown to be associated with inhibition of apoptosis. Some therapeutic agents have deleterious side effects, including non-specific lymphotoxicity, renal and bone marrow toxicity.

The methods described herein address both these problems. Drug resistance, where increasing dosages are required to achieve therapeutic benefit, is overcome by co-administering the compounds described herein with the known agent. The compounds described herein appear to sensitize target cells to known agents (and vice versa) and, accordingly, less of these agents are needed to achieve a therapeutic benefit.

The sensitizing function of the claimed compounds also addresses the problems associated with toxic effects of known therapeutics. In instances where the known agent is toxic, it is desirable to limit the dosages administered in all cases, and particularly in those cases were drug resistance has increased the requisite dosage. When the claimed compounds are co-administered with the known agent, they reduce the dosage required which, in turn, reduces the deleterious effects. Further, because the claimed compounds are themselves both effective and non-toxic in large doses, co-administration of proportionally more of these compounds than known toxic therapeutics will achieve the desired effects while minimizing toxic effects.

VI. Drug Screens

In preferred embodiments of the present invention, the compounds of the present invention, and other potentially useful compounds, are screened for their binding affinity to the oligomycin sensitivity conferring protein (OSCP) portion of the mitochondrial ATP synthase complex. In particularly preferred embodiments, compounds are selected for use in the methods of the present invention by measuring their biding affinity to recombinant OSCP protein. A number of suitable screens for measuring the binding affinity of drugs and other small molecules to receptors are known in the art. In some embodiments, binding affinity screens are conducted in in vitro systems. In other embodiments, these screens are conducted in in vivo or ex vivo systems. While in some embodiments quantifying the intracellular level of ATP following administration of the compounds of the present invention provides an indication of the efficacy of the methods, preferred embodiments of the present invention do not require intracellular ATP level quantification.

Additional embodiments are directed to measuring levels (e.g., intracellular) of superoxide in cells and/or tissues to measure the effectiveness of particular contemplated methods and compounds of the present invention. In this regard, those skilled in the art will appreciate and be able to provide a number of assays and methods useful for measuring superoxide levels in cells and/or tissues.

In some embodiments, structure-based virtual screening methodologies are contemplated for predicting the binding affinity of compounds of the present invention with OSCP.

Any suitable assay that allows for a measurement of the rate of binding or the affinity of a benzodiazepine or other compound to the OSCP may be utilized. Examples include, but are not limited to, competition binding using Bz-423, surface plasma resonace (SPR) and radio-immunopreciptiation assays (Lowman et al., J. Biol.Chem. 266:10982 [1991]). Surface Plasmon Resonance techniques involve a surface coated with a thin film of a conductive metal, such as gold, silver, chrome or aluminum, in which electromagnetic waves, called Surface Plasmons, can be induced by a beam of light incident on the metal glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed (See e.g., WO 90/05305). There are also several commercially available SPR biosensors (e.g., BiaCore, Uppsala, Sweden).

In some embodiments, copmpounds are screened in cell culture or in vivo (e.g., non-human or human mammals) for their ability to modulate mitochondrial ATP synthase activity. Any suitable assay may be utilized, including, but not limited to, cell proliferation assays (Commercially available from, e.g., Promega, Madison, Wis. and Stratagene, La Jolla, Calif.) and cell based dimerization assays. (See e.g., Fuh et al., Science, 256:1677 [1992]; Colosi et al., J. Biol. Chem., 268: 12617 [1993]). Additional assay formats that find use with the present invention include, but are not limited to, assays for measuring cellular ATP levels, and cellular superoxide levels.

The present invention also provides methods of modifying and derivatizing the compositions of the present invention to increase desirable properties (e.g., binding affinity, activity, and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In other embodiments, rational design methods are used to predict and model in silico ligand-receptor interactions prior to confirming results by routine experimentation.

VII. Therapeutic Application

In particularly preferred embodiments, the compositions (e.g., benzodiazepine derivatives) of the present invention provide therapeutic benefits to patients suffering from any one or more of a number of conditions (e.g., diseases characterized by dysregulation of necrosis and/or apoptosis processes in a cell or tissue, disease characterized by aberrant cell growth and/or hyperproliferation, etc.) by modulating (e.g., inhibiting or promoting) the activity of the mitochondrial ATP synthase (as referred to as mitochondrial $F_0F_1$ ATPase) complexes in affected cells or tissues. In further preferred embodiments, the compositions of the present invention are used to treat autoimmune/chronic inflammatory conditions (e.g., psoriasis).

In particularly preferred embodiments, the compositions of the present invention inhibit the activity of mitochondrial ATP synthase complex by binding to a specific subunit of this multi-subunit protein complex. While the present invention is not limited to any particular mechanism, nor to any understanding of the action of the agents being administered, in some embodiments, the compositions of the present invention bind to the oligomycin sensitivity conferring protein (OSCP) portion of the mitochondrial ATP synthase complex. Likewise, it is further contemplated that when the compositions of the present invention bind to the OSCP the initial affect is overall inhibition of the mitochondrial ATP synthase complex, and that the downstream consequence of binding is a change in ATP level and the production of reactive oxygen species (e.g., $O_2-$). In still other preferred embodiments, while the present invention is not limited to any particular mechanism, nor to any understanding of the action of the agents being administered, it is contemplated that the generation of free radicals ultimately results in cell killing. In yet other embodiments, while the present invention is not limited to any particular mechanism, nor to any understanding of the action of the agents being administered, it is contemplated that the inhibiting mitochondrial ATP synthase complex using the compositions and methods of the present invention provides therapeutically useful inhibition of cell proliferation.

Accordingly, preferred methods embodied in the present invention, provide therapeutic benefits to patients by providing compounds of the present invention that modulate (e.g., inhibiting or promoting) the activity of the mitochondrial ATP synthase complexes in affected cells or tissues via binding to the oligomycin sensitivity conferring protein (OSCP) portion of the mitochondrial ATP synthase complex. Importantly, by itself the OSCP has no biological activity.

Thus, in one broad sense, preferred embodiments of the present invention are directed to the discovery that many diseases characterized by dysregulation of necrosis and/or apoptosis processes in a cell or tissue, or diseases characterized by aberrant cell growth and/or hyperproliferation, etc., can be treated by modulating the activity of the mitochondrial ATP synthase complex including, but not limited to, by binding to the oligomycin sensitivity conferring protein (OSCP) component thereof. The present invention is not intended to be limited, however, to the practice of the compositions and methods explicitly described herein. Indeed, those skilled in the art will appreciate that a number of additional compounds not specifically recited herein (e.g., non-benzodiazepine derivatives) are suitable for use in the methods disclosed herein of modulating the activity of mitochondrial ATP synthase.

The present invention thus specifically contemplates that any number of suitable compounds presently known in the art, or developed later, can optionally find use in the methods of the present invention. For example, compounds including, but not limited to, oligomycin, ossamycin, cytovaricin, apoptolidin, bafilomyxcin, resveratrol, piceatannol, and dicyclohexylcarbodiimide (DCCD), and the like, find use in the methods of the present invention. The present invention is not intended, however, to be limited to the methods or compounds specified above. In one embodiment, that compounds potentially useful in the methods of the present invention may be selected from those suitable as described in the scientific literature. (See e.g., K. B. Wallace and A. A. Starkov, Annu. Rev. Pharmacol. Toxicol., 40:353-388 [2000]; A. R. Solomon et al., Proc. Nat. Acad. Sci. U.S.A., 97(26):14766-14771 [2000]).

In some embodiments, compounds potentially useful in methods of the present invention are screened against the National Cancer Institute's (NCI-60) cancer cell lines for efficacy. (See e.g., A. Monks et al., J. Natl. Cancer Inst., 83:757-766 [1991]; and K. D. Paull et al., J. Natl. Cancer Inst., 81:1088-1092 [1989]). Additional screens suitable screens (e.g., autoimmunity disease models, etc.) are within the skill in the art.

In one aspect, derivatives (e.g., pharmaceutically acceptable salts, analogs, stereoisomers, and the like) of the exemplary compounds or other suitable compounds are also contemplated as being useful in the methods of the present invention.

Those skilled in the art of preparing pharmaceutical compounds and formulations will appreciate that when selecting optional compounds for use in the methods disclosed herein, that suitability considerations include, but are not limited to, the toxicity, safety, efficacy, availability, and cost of the particular compounds.

EXAMPLES

The following examples are provided to demonstrate and further illustrate certain preferred embodiments of the present invention and are not to be construed as limiting the scope thereof.

Example 1

Preparation of Compounds

The benzodiazepine compounds are prepared using either solid-phase or soluble-phase combinatorial synthetic methods as well as on an individual basis from well-established techniques. See, for example, Boojamra, C. G. et al. (1996); Bunin, B. A., et al. (1994); Stevens, S. Y. et al., (1996); Gordon, E. M., et al., (1994); and U.S. Pat. Nos. 4,110,337 and 4,076,823, which are all incorporated by reference herein. For illustration, the following general methodologies are provided.

Preparation of 1,4-benzodiazepine-2-one compounds

Improved solid-phase synthetic methods for the preparation of a variety of 1,4-benzodiazepine-2-one derivatives with very high overall yields have been reported in the literature. (See e.g., Bunin and Ellman, J. Am. Chem. Soc., 114:10997-10998 [1992]). Using these improved methods, the 1,4-benzodiazepine-2-ones is constructed on a solid support from three separate components: 2-aminobenzophenones, α-amino acids, and (optionally) alkylating agents.

Preferred 2-aminobenzophenones include the substituted 2-aminobenzophenones, for example, the halo-, hydroxy-, and halo-hydroxy-substituted 2-aminobenzophenones, such as 4-halo-4'-hydroxy-2-aminobenzophenones. A preferred substituted 2-aminobenzophenone is 4-chloro-4'-hydroxy-2-aminobenzophenone. Preferred α-amino acids include the 20 common naturally occurring α-amino acids as well as α-amino acid mimicking structures, such as homophenylalanine, homotyrosine, and thyroxine.

Alkylating agents include both activated and inactivated electrophiles, of which a wide variety are well known in the art. Preferred alkylating agents include the activated electrophiles p-bromobenzyl bromide and t-butyl-bromoacetate.

In the first step of such a synthesis, the 2-aminobenzophenone derivative is attached to a solid support, such as a polystyrene solid support, through either a hydroxy or carboxylic acid fuinctional group using well known methods and employing an acid-cleavable linker, such as the commercially available [4-(hydroxymethyl)phenoxy]acetic acid, to yield the supported 2-aminobenzophenone. (See e.g., Sheppard and Williams, Intl. J. Peptide Protein Res., 20:451-454 [1982]). The 2-amino group of the aminobenzophenone is preferably protected prior to reaction with the linking reagent, for example, by reaction with FMOC—Cl (9-fluorenylmethyl chloroformate) to yield the protected amino group 2'-NHFMOC.

In the second step, the protected 2-amino group is deprotected (for example, the -NHFMOC group may be deprotected by treatment with piperidine in dimethylformamide (DMF)), and the unprotected 2-aminobenzophenone is then coupled via an amide linkage to an α-amino acid (the amino group of which has itself been protected, for example, as an -NHFMOC group) to yield the intermediate. Standard activation methods used for general solid-phase peptide synthesis are used (such as the use of carbodiimides and hydroxybentzotriazole or pentafluorophenyl active esters) to facilitate coupling. However, a preferred activation method employs treatment of the 2-aminobenzophenone with a methylene chloride solution of the of α-N-FMOC-amino acid fluoride in the presence of the acid scavenger 4-methyl-2,6-di-tert-butylpyridine yields complete coupling via an amide linkage. This preferred coupling method has been found to be effective even for unreactive aminobenzophenone derivatives, yielding essentially complete coupling for derivatives possessing both 4-chloro and 3-carboxy deactivating substituents.

In the third step, the protected amino group (which originated with the amino acid) is first deprotected (e.g., -NHFMOC may be converted to —NH$_2$ with piperidine in DMF), and the deprotected Bz-423s reacted with acid, for example, 5% acetic acid in DMF at 60° C., to yield the supported 1,4-benzodiazepine derivative. Complete cyclization has been reported using this method for a variety of 2-aminobenzophenone derivatives with widely differing steric and electronic properties.

In an optional fourth step, the 1,4-benzodiazepine derivative is alkylated, by reaction with a suitable alkylating agent and a base, to yield the supported fully derivatized 1,4-benzodiazepine. Standard alkylation methods, for example, an excess of a strong base such as LDA (lithium diisopropylamide) or NaH, is used; however, such methods may result in undesired deprotonation of other acidic functionalities and over-alkylation. Preferred bases, which may prevent over-alkylation of the benzodiazepine derivatives (for example, those with ester and carbamate functionalities), are those which are basic enough to completely deprotonate the anilide functional group, but not basic enough to deprotonate amide, carbamate or ester functional groups. An example of such a base is lithiated 5-(phenylmethyl)-2-oxazolidinone, which is reacted with the 1,4-benzodiazepine in tetrahydrofuran (THF) at −78° C. Following deprotonation, a suitable alkylating agent, as described above, is added.

In the final step, the fully derivatized 1,4-benzodiazepine is cleaved from the solid support. This is achieved (along with concomitant removal of acid-labile protecting groups), for example, by exposure to a suitable acid, such as a mixture of trifluoroacetic acid, water, and dimethylsulfide (85:5:10, by volume). Alternatively, the above benzodiazepines is prepared in soluble phase. The synthetic methodology was outlined by Gordon et al., J. Med. Chem., 37:1386-1401 [1994]) which is hereby incorporated by reference. Briefly, the methodology comprises trans-imidating an amino acid resin with appropriately substituted 2-aminobenzophenone imines to form resin-bound imines. These imines are cyclized and tethered by procedures similar to those in solid-phase synthesis described above. The general purity of benzodiazepines prepared using the above methodology is about 90% or higher.

Preparation of 1,4-benzodiazepine-2,5-diones

A general method for the solid-phase synthesis of 1,4-benzodiazepine-2,5-diones has been reported in detail by C. J. Boojamra et al., J. Org. Chem., 62:1240-1256 [1996]). This method is used to prepare the compounds of the present invention.

A Merrifield resin, for example, a (chloromethyl)polystyrene is derivatized by alkylation with 4-hydroxy-2,6-dimethoxybenzaldehyde sodium to provide resin-bound aldehyde. An α-amino ester is then attached to the derivatized support by reductive amination using NaBH(OAc)$_3$ in 1% acetic acid in DMF. This reductive amination results in the formation of a resin-bound secondary amine.

The secondary amine is acylated with a wide variety of unprotected anthranilic acids result in support-bound tertiary amides. Acylation is best achieved by performing the coupling reaction in the presence of a carbodiimide and the hydrochloride salt of a tertiary amine. One good coupling agent is 1-ethyl-8-[8-(dimethylamino)propyl]carbodiimide hydrochloride. The reaction is typically performed in the presence of anhydrous 1-methyl-2-pyrrolidinone. The coupling procedure is typically repeated once more to ensure complete acylation.

Cyclization of the acyl derivative is accomplished through base-catalyzed lactamation through the formation of an anilide anion which would react with an alkylhalide for simultaneous introduction of the substituent at the 1-position on the nitrogen of the heterocyclic ring of the benzodiazepine. The lithium salt of acetanilide is a good base to catalyze the reaction. Thus, the Bz-423s reacted with lithium acetanilide in DMF/THF (1:1) for 30 hours followed by reaction with appropriate alkylating agent provides the fully derivatized support-bound benzodiazepine. The compounds are cleaved from the support in good yield and high purity by using TFA/DMS/H$_2$0 (90:5:5).

Some examples of the α-amino ester starting materials, alkylating agents, and anthranilic acid derivatives that are used in the present invention are listed by Boojamra (1996), supra at 1246. Additional reagents are readily determined and either are commercially obtained or readily prepared by one of ordinary skill in the art to arrive at the novel substituents disclosed in the present invention.

For example, from Boojamra, supra, one realizes that: alkylating agents provide the R$_1$ substituents; α-amino ester starting materials provide the R$_2$ substituents, and anthranilic acids provide the R$_4$ substituents. By employing these starting materials that are appropriately substituted, one arrives at the desired 1,4-benzodiazepine-2,5-dione. The R$_3$ substituent is obtained by appropriately substituting the amine of the α-aminoester starting material. If steric crowding becomes a problem, the R$_3$ substituent is attached through conventional methods after the 1,4-benzodiazepine-2,5-dione is isolated.

Example 2

Chirality

It should be recognized that many of the benzodiazepines of the present invention exist as optical isomers due to chirality wherein the stereocenter is introduced by the α-amino acid and its ester starting materials. The above-described general procedure preserves the chirality of the α-amino acid or ester starting materials. In many cases, such preservation of chirality is desirable. However, when the desired optical isomer of the α-amino acid or ester starting material is unavailable or expensive, a racemic mixture is produced which is separated into the corresponding optical isomers and the desired benzodiazepine enantiomer is isolated.

For example, in the case of the 2,5-dione compounds, Boojamra, supra, discloses that complete racemization is accomplished by preequilibrating the hydrochloride salt of the enantiomerically pure α-amino ester starting material with 0.3 equivalents of i-Pr$_2$EtN and the resin-bound aldehyde for 6 hours before the addition of NaBH(OAc)$_3$. The rest of the above-described synthetic procedure remains the same. Similar steps are employed, if needed, in the case of the 1,4-benzodiazepine-2-dione compounds as well.

Methods to prepare individual benzodiazepines are well-known in the art. (See e.g., U.S. Pat. Nos. 3,415,814; 3,384,635; and 3,261,828, which are hereby incorporated by reference). By selecting the appropriately substituted starting materials in any of the above-described methods, the benzodiazepines of this invention are prepared with relative ease.

Example 3

Reagents

Bz-423 is synthesized as described above. FK506 is obtained from Fujisawa (Osaka, Japan). N-benzoylcarbonyl-Val-Ala-Asp-fluoromethylketone (z-VAD) is obtained from Enzyme Systems (Livermore, Calif.). Dihydroethidium (DHE) and 3,3'-dihexyloxacarbocyanine iodide (DiOC$_6$(3)) are obtained from Molecular Probes (Eugene, Oreg.). FAM-VAD-fmk is obtained from Intergen (Purchase, N.J.). Manganese(III)meso-tetrakis(4-benzoic acid)porphyrin (MnT-BAP) is purchased from Alexis Biochemicals (San Diego, Calif.). Benzodiazepines is synthesized as described (See, B. A. Bunin et al., Proc. Natl. Acad. Sci. U.S.A., 91:4708-4712 [1994]). Other reagents were obtained from Sigma (St. Louis, Mo.).

Example 4

Animals and Drug Delivery

Female NZB/W mice (Jackson Labs, Bar Harbor, Me.) are randomly distributed into treatment and control groups. Control mice receive vehicle (50 µL aqueous DMSO) and treatment mice receive Bz-423 dissolved in vehicle (60 mg/kg) through intraperitoneal injections. Peripheral blood is obtained from the tail veins for the preparation of serum. Samples of the spleen and kidney are preserved in either 10% buffered-formalin or by freezing in OCT. An additional section of spleen from each animal is reserved for the preparation of single cell suspensions.

Example 5

Primary Splenocytes, Cell Lines, and Culture Conditions

Primary splenocytes are obtained from 6 month old mice by mechanical disruption of spleens with isotonic lysis of red blood cells. B cell-rich fractions are prepared by negative selection using magnetic cell sorting with CD4, CD8a and CD11b coated microbeads (Miltenyi Biotec, Auburn, Calif.). The Ramos line is purchased from the ATCC (Monassis, Ga.). Cells are maintained in RPMI supplemented with 10% heat-inactivated fetal bovine serum (FBS), penicillin (100 U/ml), streptomycin (100 µg/ml) and L-glutamine (290 µg/ml). Media for primary cells also contains 2-mercaptoethanol (50 µM). All in vivo studies are performed with 0.5% DMSO and 2% FBS. In vitro experiments are conducted in media containing 2% FBS. Organic compounds are dissolved in media containing 0.5% DMSO.

Example 6

Histology

Formalin-fixed kidney sections were stained with hematoxylin and eosin (H&E) and glomerular immune-complex deposition is detected by direct immunofluorescence using frozen tissue stained with FITC-conjugated goat anti-mouse IgG (Southern Biotechnology, Birmingham, Ala.). Sections are analyzed in a blinded fashion for nephritis and IgG deposition using a 0-4+scale. The degree of lymphoid hyperplasia is scored on a 0-4+ scale using spleen sections stained with H&E. To identify B cells, sections are stained with biotinylated-anti-B220 (Pharmingen; 1 µg/mL) followed by streptavidin-Alexa 594 (Molecular Probes; 5 µg/mL). Frozen spleen sections are analyzed for TUNEL positive cells using an In situ Cell Death Detection kit (Roche) and are evaluated using a 0-4+ scale.

Example 7

TUNEL Staining

Frozen spleen sections are analyzed using an In situ Cell Death Detection kit (Roche Molecular Biochemicals, Indianapolis, Ind.). Sections are blindly evaluated and assigned a score (0-4+) on the basis of the amount of TUNEL-positive staining. B cells are identified by staining with biotinylated-anti-B220 (Pharmingen, San Diego, Calif.; 1 µg/mL, 1 h, 22° C.) followed by streptavidin-Alexa 594 (Molecular Probes, Eugene, Oreg.; 5 µg/mL, 1 h, 22° C.).

Example 8

Flow Cytometric Analysis of Spleen Cells from Treated Animals

Surface markers are detected (15 m, 4° C.) with fluorescent-conjugated anti-Thy 1.2 (Pharmingen, 1 µg/mL) and/or anti-B220 (Pharmingen, 1 µg/mL). To detect outer-membrane phosphatidyl serine, cells are incubated with FITC-conjugated Annexin V and propidium iodide (PI) according to manufacturer protocols (Roche Molecular Biochemicals). Detection of TUNEL-positive cells by flow cytometry uses the APO-BRDU kit (Pharmingen). Superoxide and MPT are assessed by incubation of cells for 30 m at 27 degrees C. with 10 µM dihydroethidium and 2 µM 3,3'-dihexyloxacarbocyanine iodide ($DIOC_6(3)$) (Molecular Probes). Prodidium idodie is used to determine viability and DNA content. Samples are analyzed on a FACSCalibur flow cytometer (Becton Dickinson, San Diego, Calif.).

Example 9

B Cell Stimulation

Ramos cells are activated with soluble goat $Fab_2$ anti-human IgM (Southern Biotechnology Associates, 1 µg/ml) and/or purified anti-human CD40 (Pharmingen, clone 5C3, 2.5 µg/ml). Mouse B cells are activated with affinity purified goat anti-mouse IgM (ICN, Aurora, Ohio; 20 µg/ml) immobilized in culture wells, and/or soluble purified anti-mouse CD40 (Pharmingen, clone HM40-3, 2.5 µg/ml). LPS is used at 10 µml. Bz-423 is added to cultures immediately after stimuli are applied. Inhibitors are added 30 m prior to Bz-423.

Example 10

Statistical Analysis

Statistical analysis is conducted using the SPSS software package. Statistical significance is assessed using the Mann-Whitney U test and correlation between variables is assessed by two-way ANOVA. All p-values reported are one-tailed and data are presented as mean±SEM.

Example 11

Detection of Cell Death and Hypodiploid DNA

Cell viability is assessed by staining with propidium iodide (PI, 1 µg/mL). PI fluorescence is measured using a FACSCalibur flow cytometer (Becton Dickinson, San Diego, Calif.). Measurement of hypodiploid DNA is conducted after incubating cells in DNA-labeling solution (50 µg/mL of PI in PBS containing 0.2% Triton and 10 µg/mL RNAse A) overnight at 4 degrees C. The data is analyzed using the CellQuest software excluding aggregates.

Example 12

Detection of $O_2^-$, $\psi_m$, and Caspase Activation

To detect $O_2^-$, cells are incubated with DHE (10 µM) for 30 min at 37° C. and are analyzed by flow cytometry to measure ethidium fluorescence. Flow analysis of mitochondrial transmembrane potential ($\psi_m$) is conducted by labeling cells with DiOC$_6$(3) (20 nM) for 15 min at 37 degrees C. A positive control for disruption of $\psi_m$ is established using carbonyl cyanide m-chlorophenylhydrazone (CCCP, 50 µM). Caspase activation assays are performed with FAM-VAD-fluoromethylketone. Processing of the substrate is evaluated by flow cytometry.

Example 13

Subcellular Fractionation and Cytochrome c Detection

Ramos cells (250×10$^6$ cells/sample) are treated with Bz-423 (10 µM) or vehicle for 1 to 5 h. Cells are pelleted, re-suspended in buffer (68 mM sucrose, 220 mM mannitol, 10 mM HEPES-NaOH, pH 7.4, 10 mM KCl, 1 mM EDTA, 1 mM EGTA, 10 µg/mL leupeptin, 10 µg/mL aprotinin, 1 mM PMSF), incubated on ice for 10 min, and homogenized. The homogenate is centrifuged twice for 5 min at 4° C. (800 g) to pellet nuclei and debris and for 15 min at 4° C. (16,000 g) to pellet mitochondria. The supernatant is concentrated, electrophoresed on 12% SDS-PAGE gels, and transferred to Hybond ECL membranes (Amersham, Piscataway, N.J.). After blocking (PBS containing 5% dried milk and 0.1% Tween), the membranes are probed with an anti-cytochrome c monoclonal antibody (Pharmingen, San Diego, Calif.; 2 µg/mL) followed by an anti-mouse horseradish peroxidase-conjugated secondary with detection by chemiluminescence (Amersham).

Example 14

ROS Production in Isolated Mitochondria

Male Long Evans rats are starved overnight and sacrificed by decapitation. Liver samples are homogenized in ice cold buffer A (250 mM sucrose, 10 mM Tris, 0.1 mM EGTA, pH 7.4), and nuclei and cellular debris are pelleted (10 min, 830 g, 4° C.). Mitochondria are collected by centrifugation (10 min, 15,000 g, 4° C.), and the supernatant is collected as the S15 fraction. The mitochondrial pellet is washed three times with buffer B (250 mM sucrose, 10 mM Tris, pH 7.4), and re-suspended in buffer B at 20-30 mg/mL. Mitochondria are diluted (0.5 mg/mL) in buffer C (200 mM sucrose, 10 mM Tris, pH 7.4, 1 mM KH$_2$PO$_4$, 10 µM EGTA, 2.5 µM rotenone, 5 mM succinate) containing 2',7'-dichlorodihydrofluorescin diacetate (DCFH-DA, 1 µM). For state 3 measurements, ADP (2 mM) is included in the buffer, and prior to the addition of Bz-423, mitochondria are allowed to charge for 2 min. To induce state 4, oligomycin (10 µM) is added to buffer C. The oxidation of DCFH to 2',7'-dichlorofluorescein (DCF) is monitored at 37° C. with a spectrofluorimeter ($\lambda_{ex}$: 503 nm; $\lambda_{em}$: 522 nm). To detect effects on O$_2^-$ and delta $\psi_m$, mitochondria are incubated for 15 min at 37° C. in buffer C with vehicle, Bz-423, or CCCP containing DHE (5 µM) or DiOC$_6$(3) (20 nM), and aliquots are removed for analysis by fluorescence microscopy.

Example 15

Flow Cytometric Analysis of Splenocytes

Splenocytes are prepared by mechanical disruption and red blood cells removed by isotonic lysis. Cells are stained at 4° C. with fluorescent-conjugated anti-Thy 1.2 (Pharmingen; 1 µg/mL) and/or anti-B220 (Pharmingen; 1 µg/mL) for 15 min. To detect outer-membrane phosphatidyl serine, cells are incubated with FITC-conjugated Annexin V and PI (Roche Molecular Biochemicals, Indianapolis, Ind.; 1 µg/mL).

Example 16

In vivo Determination of ROS

Spleens are removed from 4-mo old NZBIW mice treated with Bz-423 or vehicle and frozen in OCT. ROS production is measured using manganese(II) 3,3,9-diaminobenzidine as described in E. D. Kerver et al. (See, E. D. Kerver et al., Histochem. J., 29:229-237 [1997]).

Example 17

IgG Titers, BUN, and Proteinuria

Anti-DNA and IgG titers are determined by ELISA as described in P. C. Swanson et al. (See, P. C. Swanson et al., Biochemistry, 35:1624-1633 [1996]). Serum BUN is measured by the University of Michigan Hospital's clinical laboratory. Proteinuria is monitored using ChemStrip 6 (Boehringer Mannheim).

Example 18

Benzodiazepine Studies

Benzodiazepine studies on animals are described in U.S. Patent No.: 20010016583, published Aug. 23, 2001, herein incorporated by reference in its entirety.

Example 19

Mediators of Bz-423 Induced Apoptosis

To characterize the death mechanism engaged by Bz-423, intracellular ROS, $\Delta\psi_m$, cytochrome c release, caspase activation, and DNA fragmentation were measured over time (the results presented are for B cells but do characterize the response in many different cell types). The first event detected after exposure to Bz-423 is an increase in the fraction of cells that stain with dihyroethedium (DHE), a redox-sensitive agent that reacts specifically with O$_2^-$.

Levels of O$_2^-$ diminished after an early maximum at 1 hour and then increased again after 4 hours of continued treatment. This bimodal pattern pointed to a cellular mechanism limiting O$_2^-$ and suggested that the "early" and "late" O$_2^-$ maxima resulted from different processes.

Collapse of $\Delta\Psi_m$ was detected using DiOC$_6$(3), a mitochondria-selective potentiometric probe. The gradient change began after the early O$_2^-$ response and was observed in >90% of cells by 5 hours.

Cytochrome c release from mitochondria, a key step enabling caspase activation, was studied by immunoblotting cytosolic fractions. Levels of cytosolic cytochrome c above amounts in cells treated with vehicle were detected by 5 hours. This release was coincident with the disruption of $\Delta\Psi_m$, and together, these results were consistent with opening of the PT pore. Indeed, the late increase in O$_2^-$ tracked with the $\Delta\Psi_m$ collapse and the release of cytochrome c, suggesting that the secondary rise in O$_2^-$ resulted from these processes.

Caspase activation was measured by processing of the pan-caspase sensitive fluorescent substrate FAM-VAD-fmk. Caspase activation tracked with $\Delta\psi_m$, whereas the appearance of hypodiploid DNA was slightly delayed with respect to caspase activation. Collectively, these results indicated that Bz-423 induces a mitochondrial-dependent apoptotic pathway.

Example 20

Bz-423 directly Targets Mitochondria

Since the early $O_2^-$ preceded other cellular events, it was possible that this ROS had a regulatory role. In non-phagocytic cells, redox enzymes, along with the MRC, are the primary sources of ROS. Inhibitors of these systems were assayed for an ability to regulate Bz-423-induced $O_2^-$ in order to determine the basis for this response. Of these reagents, only $NaN_3$, which acts primarily on cytochrome c oxidase (complex IV of the mitochondrial respiratory chain, MRC), and micromolar amounts of FK506, which block the formation of $O_2^-$ by the ubiquinol-cytochrome c reductase component of MRC complex III, modulated Bz-423. These findings suggested that mitochondria are the source of Bz-423-induced $O_2^-$ and that a component of the MRC is involved in the response. Although the inhibition by FK506 may result from binding to either calcineurin or FK506-binding proteins, natural products that bind tightly to these proteins (rapamycin and cyclosporin A, respectively) did not diminish the Bz-423 $O_2^-$ response.

$O_2^-$ production by Bz-423 may result from binding to a protein within mitochondria or a target in another compartment that signals mitochondria to generate ROS. To distinguish between these alternatives, isolated rat liver mitochondria were assayed for ROS production by monitoring the oxidation of 2',7'-dichlorodihydrofluorescin diacetate to of 2',7'-dichlorofluorescin in the presence and absence of Bz-423. In this assay, the rate of DCF production increased after a lag period during which endogenous reducing equivalents were consumed and the acetate moieties on the probe were hydrolyzed to yield 2',7'-dichlorodihydrofluorescin, the redox-active species. Under aerobic conditions supporting state 3 respiration, both antimycin A, which generates $O_2^-$ by inhibiting ubiquinol-cytochrome c reductase, and Bz-423 increased the rate of ROS production nearly two-fold after the induction phase, based on comparing the slopes of each curve to control. Swelling was not observed, demonstrating that Bz-423 does not directly target the MPT pore. Neither Bz-423 nor antimycin A generated substantial ROS in the subcellular S15 fraction (cytosol and microsomes), and Bz-423 does not stimulate ROS if mitochondria are in state 4, even though antimycin A is active under these conditions. Together, these experiments demonstrate that mitochondria contain a molecular target for Bz-423, and state 3 respiration is required for the $O_2^-$ response.

Example 21

Bz-423-Induced ROS Comes from Mitochondria

MRC complexes I and III are the primary sources of ROS within mitochondria. Evidence presented above suggests that Bz-423-induced ROS comes from mitochondria. To test this hypothesis, MRC function was knocked out the resulting cells were examined for ROS in response to Bz-423. Complexes I-IV in the MRC are partially encoded by mitochondrial DNA (mtDNA). Culturing cells over extended periods of time in the presence of ethidium bromide removed mtDNA, suggesting that mtDNA encoded proteins are not produced and electron transport along the MRC does not occur (cells devoid of mtDNA and associated proteins are often termed $\rho^0$ cells). Because ethidium bromide is toxic to Ramos cells, these experiments were conducted with Namalwa B cells, another mature B cell line. Treating Namalwa $\rho^0$ cells with Bz-423 did not result in an ROS response, as was observed in both Ramos and Namalwa $\rho^+$ cells.

Since the early ROS is critical to Bz-423 induced apoptosis, results detected with the Namalwa $\rho^0$ cells would seemingly predict that these cells would be protected from the toxic effects of Bz-423. However, after 6 hours, the MPT was triggered and Namalwa $\rho^0$ cells underwent apoptosis in response to Bz-423. In $\rho^+$ cells, proton pumping by the MRC maintained the mitochondrial gradient $\Delta\psi_m$. Since a functional MRC is not present in $\rho^0$ cells, $\Delta\psi_m$ is supported by complex V (the $F_1F_0$-ATPase) functioning as an ATPase (deletion of subunits 6 and b in $\rho^0$ cells abolishes the synthase activity of this enzyme). In this case, inhibition of complex V ATPase would cause collapse of the gradient and subsequent cell death.

Example 22

Bz-423 Targets the Mitochondrial $F_1F_0$-ATPase

Oligomycin, a macrolide natural product that binds to the mitochondrial $F_1F_0$-ATPase, induces a state 3 to 4 transition and generates $O_2^-$ like Bz-423. Based on these similarities, it is possible that the $F_1F_0$-ATPase is also the molecular target for Bz-423. To test this hypothesis, the effect of Bz-423 on ATPase activity in sub-mitochondrial particles (SMPs) was examined. Indeed, Bz-423 inhibited the mitochondrial ATPase activity of bovine SMPs with an ED 50 ca. 5 µM.

>40 derivatives of Bz-423 were developed to determine the elements on this novel agent required for biological activity. Assessing these compounds in whole cell apoptosis assays revealed that a hydroxyl group at the C'4 position and an aromatic ring roughly the size of the napthyl moiety were useful. The potency of these analogues in cell based assays correlated with the $ED_{50}$ values in ATPase inhibition experiments using SMPs. These observations indicated that the mitochondrial ATPase is the molecular target of Bz-423. At concentrations where these derivatives are cytotoxic (80 µM), other benzodiazepines and PBR ligands (e.g., PK111195 and 4-chlorodiazepam) do not significantly inhibit mitochondrial ATPase activity, suggesting that the molecular target of Bz-423 is distinct from the molecular target(s) of these other compounds.

Example 23

Bz-423 Binds to the OSCP

As part an early group of mechanistic studies of Bz-423, a biotinylated analogue was synthesized by replacing the N-methyl group with a hexylaminolinker to which biotin was covalently attached (this modification did not alter the activity of Bz-423). This molecule was used to probe a display library of human breast cancer cDNAs (Invitrogen) that are expressed as fusion proteins on the tip of T7 phage. Following the screening methods described by Austin and co-workers using biotinylated version of KF506 to identify new FK506 binding proteins, the OSCP component of the mitochondrial $F_1F_0$-ATPase was identified as a binding protein for Bz-423 (FIG. 1).

To determine if Bz-423 indeed binds to the OSCP and the affinity of the interaction, human OSCP was overexpressed in E. coli. Titrating a solution of Bz-423 into the OSCP resulted in quenching of the intrinsic protein fluorescence and afforded a $K_d$ of 200±40 nM (FIG. 2). The binding of several Bz-423 analogues was also measured and it was found that their affinity for the OSCP paralleled their potency in both whole cell cytotoxicity assays as well as ATPase inhibition experiments using SMP. These data provided cogent evidence that Bz-423 binds to the OSCP on the mitochondrial ATPase. Bz-423 is the only known inhibitor of the ATPase that functions through binding to the OSCP. Since the OSCP does not contain the ATP binding site and it does not comprise the proton channel, it is possible that Bz-423 functions by altering the molecular motions of the ATPase motor.

Example 24

RNAi Knockouts of the OSCP Protect Against Bz-423 Induced Cell Death

To complement the chemical and biochemical target identification and validation studies described above, experiments were conducted to knockout the OSCP in whole cells. In vitro, removing the OSCP from the ATPase abolishes synthase function without altering the hydrolytic activity of the enzyme. In yeast, OSCP knockouts are not lethal; in these cells, hydrolysis of ATP provides the chemical potential to support $\Delta\Psi_m$ thereby maintaining mitochondrial integrity. Since yeast OSCP has limited sequence homology to the mammalian protein (~30%), these experiments were conducted in cell lines from human origin.

Since the OSCP is nuclear encoded, RNA interference (RNAi), a technique that can achieve post-transcriptional gene silencing, was employed to knockout this protein. For these experiments, HEK 293 cells were transfected with each of three chemically synthesized small interfering RNA molecules (siRNA) specific for the OSCP sequence using oligofectamine. These cells are transfected in a highly efficient (90%) manner by oligofectamine. OSCP expression was analyzed by immunoblot at 24 h, 48 h, 72 h and 96 h after transfection. The maximum silencing of OSCP expression (64%) occurred at 72 h after transfection (FIG. 3). OSCP siRNA transfected HEK 293 cells had a reduced Bz—ROS and apoptosis in response to Bz-423 relative to cells transfected with a scrambled sequence control siRNA. These results indicated that siRNA is effective at reducing OSCP and suggested that Bz-423 mediated cell death signaling involves the OSCP.

Example 25

Effect of Bz-423 on Cellular Proliferation

Like most 1,4-benzodiazepines, Bz-423 binds strongly to bovine serum albumin (BSA), which reduces the effective concentration of drug free in solution. For example, in tissue culture media containing 10% (v/v) fetal bovine serum (FBS), ca. 99% of the drug is bound to BSA. Therefore, cell culture cytotoxicity assays are conducted in media with 2% FBS to reduce binding to BSA and increase the free [Bz-423]. Under these conditions, the dose response-curve is quite sharp such that there is a limited concentration range at which Bz-423 is only partly effective. Since some benzodiazepines are known to have anti-proliferative properties, the effect of Bz-423 at concentrations <$ED_{50}$ were carefully analyzed and observed that in addition to inducing apoptosis, Bz-423 prevented cell growth after 3 d in culture. In these low serum conditions, the cytotoxic and anti-proliferative effects overlapped making it difficult to study each effect independently. However, by increasing the [BSA] or increasing FBS to 10%, the dose-response curve flattened (and the cytotoxicity $ED_{50}$ increased) and Bz-423 induced cytotoxicicty could be clearly distinguished from effects on proliferation. At lower amounts of drug (e.g., 10-15 µM), Bz-423 had minimal cytotoxicity whereas at concentrations >20 µM only apoptosis was observed (the death pathway described above including a bimodal ROS response, and was also observed in media containing 10% FBS). While higher amounts of drug may also block proliferation, it caused apoptosis well before the effects on proliferation could be observed. Dose response curves were similar in experiments where BSA was added to media containing 2% FBS to simulate media containing 10% FBS, which demonstrated that antiproliferation and cytotoxicity were not affected by other constituents of serum.

To confirm the decrease in cell number relative to control cells after 3 d of treatment is due to decreased proliferation and not cell death balanced by proliferation, in addition to cell counting, cell divisions were studied. PKH-67 is a fluorescent probe that binds irreversibly to cell membranes and upon cell division is partitioned equally between the daughter cells, making it possible to quantify cell division by flow cytometry. Ramos cells stained with PKH67 and treated with Bz-423 had fewer cell divisions at sub-cytotoxic concentrations which confirmed that the decrease in cell number was due to anti-proliferative affects and not cell death. To determine if Bz-423 induced anti-proliferation was specific to Ramos cells, cell counting and cell cycle experiments were done in other B cell lines and cell lines derived from solid tumors. As seen in Table 3, the effects on blocking proliferation were not unique to lymphoid cells which suggested a target, common to multiple tissue types, mediated the block in proliferation.

TABLE 3

$ED_{50}$ (µM) for antiproliferation of cells treated for 72 h in media with 10% FBS. Cells for study included Ramos cells and clones transfected to overexpress Bcl-2 and Bcl-$x_L$, ovarian cells with null p53 (SKOV3); neuroblastoma cell lines (IMR-32, Lan-1, SHEP-1); and malignant B cell lines.

| Ramos | Bcl-2 | Bcl-$X_L$ | SKOV3 | IMR-32 | Lan-1 | SHEP-1 | CA46 | Raji |
|---|---|---|---|---|---|---|---|---|
| 10.7 | 11.9 | 13.7 | 18.2 | 18.0 | 13.7 | 15.9 | 13.4 | 12.9 |

Example 26

Gene Profiling Cells Treated with Bz-423

Gene profiling experiments were conducted to probe the mechanism by which Bz-423 blocks cellular proliferation. In studies using cyclohexamide as an inhibitor of protein synthesis, it was found that Bz-423-induced cell death did not depend on new protein synthesis. Therefore, changes in gene expression were more likely relevant only to the mechanism of anti-proliferation. To increase the likelihood of detecting changes involved in signal-response coupling rather than down-stream effects, cells were profiled that were treated with Bz-423 for 3 h. This is the point just after the ROS early maximum, but before other cellular changes occur, including opening of the mitochondria permeability pore.

The discovery of the pro-apoptotic, cytotoxic and growth inhibitory properties of Bz-423 against pathogenic cell types identified the potential for this class of agents to be therapeutic against autoimmune diseases, cancers and other neoplastic diseases. Further experimental evidence from an analysis of the changes in gene expression induced by this agent expanded the mechanistic understanding of this compound's action and added to the collection of therapeutic effects it modulates.

In vitro testing with Ramos cells to determine the changes in gene expression (at the level of mRNA) induced by Bz-423 was performed by culturing cells at a density of 500,000 cells per ml. Solvent control (DMSO, final concentration 0.1% V/V]), Bz-423, or Bz-OMe (10 µM) was added to cells. After 4 h, cells were harvested and RNA prepared using Trizol Reagent (#15596-018, Life Technologies, Rockville, Md.) and the RNeasy Maxi Kit (#75162, Qiagen, Valencia, Calif.) according to manufacturers protocols. Single stranded cDNA was synthesized by reverse transcription using poly (A) RNA present in the starting total RNA sample. Single stranded cDNA was converted into double stranded cDNA and then in vitro transcription carried out in the presence of biotinylated UTP and CTP to produce biotin-labeled cRNA. cRNA was fragmented in the presence of Mg2+, and hybridized to the human genome U133A Genechip array (Affymetrix). Hybridization results were quantified using a GeneArray scanner and analysis carried out according to the instructions provided by Affymetrix.

Expression profiling using RNA isolated from cells treated with Bz-423, Bz-OMe, or vehicle control was done with the HGU133A Affymetrix gene chip, which represents about 22,000 human genes. Using criteria that include p<0.01, 16 genes are expressed 8-fold or more over control cells. As expected based on the molecular target of Bz-423, many of these genes were involved in glycolysis.

The data were analyzed to detect genes changes Bz treatment according to the criteria that the log-transformed mean signal changed at least four-fold in treated compared to vehicle control samples and that the coefficient of variance for control values (n=4) was less than 10%. These genes represent targets that may mediate therapeutic responses.

The gene expression results for Bz-423 and Bz-OMe each provide a unique fingerprint of information. The structure of Bz-OMe is as follows:

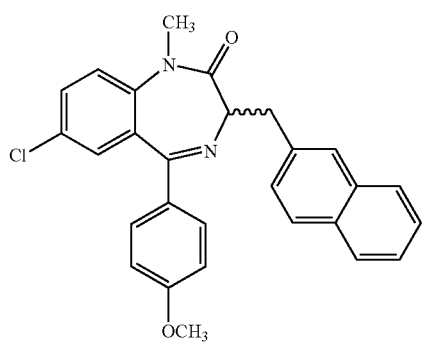 [SMILES: COc1ccc(C2=NC(Cc3ccc4ccccc4c3)C(=O)N(C)c3ccc(Cl)cc32)cc1]

Expression of some genes change similarly after exposure to both Bz-423 and Bz-OMe. Thus, the genes that are commonly regulated between the two compounds are particularly relevant for understanding gene regulation through a more general class of compounds. FIG. 4 presents data showing gene expression profiles of cells treated by Bz-423 and Bz-OMe.

Example 27

Effect of Bz-423 on ODC Levels and Activity

To determine whether ODC activity and polyamine metabolism is affected by Bz-423, as suggested by RNA profiling data, ODC activity in cells treated with Bz-423 was directly measured in comparison with a vehicle control. In these experiments, the conversion of ornithine to putrescine was quantified using $^3$H-ornithine. For comparisons, control cells were treated with vehicle control or difluoromethyl ornithine (DFMO), a potent inhibitor of ornithine decarboxylase (like Bz-423, DFMO is a potent anti-proliferative agent). As seen in FIG. 3, treating cells for 4 h with Bz-423 significantly reduced ODC activity in a dose-dependant fashion, which is consistent with among other things, an incrrease in antizyme 1, as suggested by RNA profiling. The reduction in ODC activity was paralleled by a decrease in ODC protein levels measured under the same conditions.

As described above, Bz-423 induced apoptosis was signaled by an ROS response that arose from MRC complex III as a result of the state 3 to 4 transition. It was next sought to determine if the ROS response, critical for apoptosis, also mediated these effects on ODC. If the ROS was required for the decrease in ODC activity, it would likewise be implicated as potentially part of the anti-proliferative response to Bz-423. To test this, Ramos cells were treated with Bz-423, DFMO, or vehicle control for 4 h. In parallel, a second group of cells was pre-incubated with MnTBAP to limit the ROS and then cultured with Bz-423, DFMO, and vehicle control. MnTBAP significantly reversed inhibition of ODC by Bz-423.

Collectively these data suggested the possible interpretation that high [Bz-423] (e.g. >10 µM) generate sufficient amounts of ROS that could not be detoxified by cellular anti-oxidants, and resulted in apoptosis within 18 h. Lower [Bz-423] induced a proportionally smaller ROS response that was insufficient to trigger apoptosis. In this case, however, the ROS may be capable of inhibiting ODC or otherwise blocking cellular proliferation.

Consistent with this hypothesis, a compound in which the phenolic hydroxyl is replaced by Cl (designated Bz-Cl) was minimally cytotoxic (activity decreased by ca 80% compared to Bz-423) and generated a small ROS response in cells, while also binding less tightly to the OSCP ($K_d \approx 5$ µM). This compound also inhibited ODC activity (FIG. 3), as predicted by the above hypothesis. Given the proposed role and nature of Bz-423 induced ROS in mediating growth arrest, Bz-Cl was tested against the panel of cells in Table 2 and found that after 3 d it reduced proliferation to a similar extent as Bz-423, with comparable $ED_{50}$ values. These results demonstrated that the antiproliferative effects of these compounds could be obtained using chemical analogues of Bz-423 that block proliferation without inducing apoptosis.

Example 28

Structure Activity Studies of Novel Cytotoxic Benzodiazepines

Based on these properties of Bz-423, a range of Bz-423 derivatives were synthesizedto probe structural elements of this novel compound important for binding and activity. Replacing the N-methyl group or chlorine with a hydrogen had little effect on lymphotoxic activity against immortalized Ramos B cells or Jurkat T cells in culture. Similarly, both enantiomers of Bz-423 were equipotent, which indicates that the interaction between Bz-423 and its molecular target involves two-point binding. In contrast to these data, removing a naphthalalanine (see Table 1). The present invention is not limited to a particular mechanism, and an understanding of a mechanism is not necessary to practice the present invention, nonetheless, it is contemplated that moiety or replacing the phenolic hydroxyl group with hydrogen abolished all cytotoxic activity (Table 1). Based on these observations changes to the C'3 and C'4 positions were investigated. Replacing 1-naphthol with 2-naphtho has little effect on cell killing. Similarly, replacing the napthylalanine with other hydrophobic groups of comparable size had little effect on cytotoxic properties of Bz-423. By contrast, quinolines 7-9 were each less potent than Bz-423. The present invention is not limited to a particular mechanism, and an understanding of a mechanism is not necessary to practice the present invention, nonetheless, it is contemplated that theses data suggest a preference for a hydrophobic substituent within the binding site for Bz-423. Smaller C3 substituents were only somewhat less potent than Bz-423 whereas compounds with aromatic groups containing oxygen were significantly less cytotoxic. These data clearly indicate that a bulky hydrophobic aromatic substituent is useful for optimal activity.

TABLE 1

Potency of Bz-423 derivatives. Cell death was assessed by culturing Ramos B cells in the presence of each compound in a dose-response fashion. Cell viability was measured after 24 h propidium iodide exclusion using flow cytometry.
In this assay, the $EC_{50}$ for PK11195, diazepam, and 4-Cl-diazepam is >80 μM.

| Compound | | $EC_{50}$ (μM)[a] |
|---|---|---|
| -naphthalAla | 1 | >80 |
| -phenol | 2 | >80 |
| 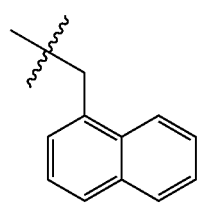 [SMILES: *Cc1cccc2ccccc12] | 3 | 5 |
| 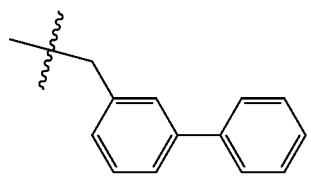 [SMILES: *Cc1cccc(-c2ccccc2)c1] | 4 | 4 |
| 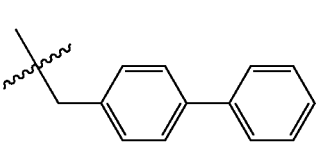 [SMILES: *Cc1ccc(-c2ccccc2)cc1] | 5 | 7 |

TABLE 1-continued

Potency of Bz-423 derivatives. Cell death was assessed by culturing Ramos B cells in the presence of each compound in a dose-response fashion. Cell viability was measured after 24 h propidium iodide exclusion using flow cytometry.
In this assay, the $EC_{50}$ for PK11195, diazepam, and 4-Cl-diazepam is >80 μM.

| Compound | | $EC_{50}$ (μM)[a] |
|---|---|---|
| 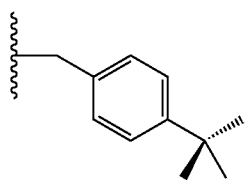 | 6 | 4 |
| 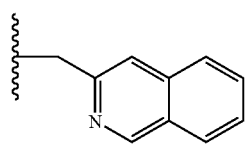 [SMILES: *Cc1cc2ccccc2cn1] | 7 | 11 |
| 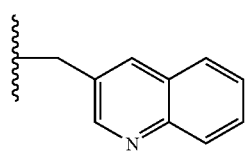 [SMILES: *Cc1cnc2ccccc2c1] | 8 | 12 |
| 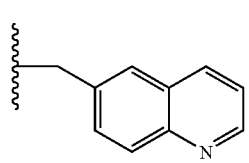 [SMILES: *Cc1ccc2ncccc2c1] | 9 | 15 |
| 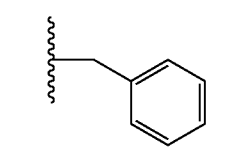 [SMILES: *Cc1ccccc1] | 10 | 12 |

TABLE 1-continued

Potency of Bz-423 derivatives. Cell death was assessed by culturing Ramos B cells in the presence of each compound in a dose-response fashion. Cell viability was measured after 24 h propidium iodide exclusion using flow cytometry.
In this assay, the $EC_{50}$ for PK11195, diazepam, and 4-Cl-diazepam is >80 µM.

| Compound | | $EC_{50}$ (µM)[a] |
|---|---|---|
| 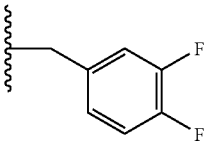 [SMILES: *Cc1ccc(F)c(F)c1] | 11 | 10 |
| 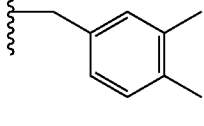 | 12 | 6 |
| 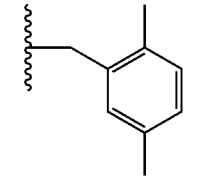 [SMILES: *Cc1cc(C)ccc1C] | 13 | 7 |
| 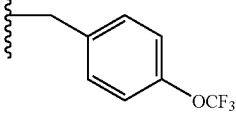 | 14 | 35 |
| 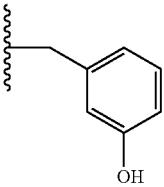 [SMILES: *Cc1cccc(O)c1] | 15 | 25 |

[a]Each EC50 value was determined twice in triplicate and has an error of ±5%.

Placing a methyl group ortho to the hydroxyl (16) does not alter the activity of Bz-423 whereas moving the hydroxyl to the C'4 (17) position decreased potency 2-fold (Table 2). By contrast, replacing the hydroxyl with chlorine or azide, or methylating the phenol effectively abolishes the cytotoxic activity of Bz-423. The present invention is not limited to a particular mechanism, and an understanding of the mechanism is not necessary to practice the present invention, nonetheless, it is contemplated that these data indicate that a hydroxyl group positioned at the C'4 carbon is required for optimal activity, possibly by making a critical contact upon target binding. However, molecules possessing a phenolic substructure can also act as alternate electron carriers within the MRC. Such agents accept an electron from MRC enzymes and transfer it back to the chain at point of higher reducing potential. This type of 'redox cycling' consumes endogenous reducing equivalents (e.g., glutathione) along with pyrimidine nucleotides and results in cell death. To distinguish between these alternatives, it was determined whether Bz-423 redox cycles in the presence of sub-mitochondrial particles using standard NADH and NAD(P)H oxidation assays. Unlike the positive controls (doxorubicin and menadione), Bz-423 does not lead to substrate oxidation which strongly suggests that it does not redox cycle. The present invention is not limited to a particular mechanism, and an understanding of the mechanism is not necessary to practice the present invention, nonetheless, it is contemplated that collectively, the data indicate that the decreased activity of compounds 18-20 results from removing an interaction that mediates binding of Bz-423 to its target protein.

TABLE 2

Potency of Bz-423 derivatives. Cell death was assessed as described in Table 1

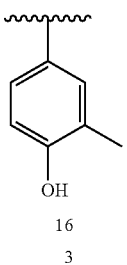 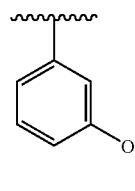 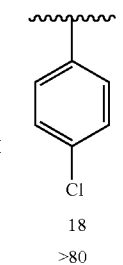 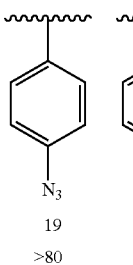 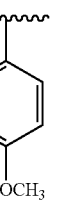

| Compound | 16 | 17 | 18 | 19 | 20 |
|---|---|---|---|---|---|
| $EC_{50}$ | 3 | 6 | >80 | >80 | >80 |

Cells rapidly produce $O_2^-$ in response to Bz-423 and blocking this signal (e.g., by inhibiting ubiquinol cytochrome c reductase, which is the enzyme that produces $O_2^-$ in response to Bz-423) prevents apoptosis. To determine if the Bz-423 derivatives kill cells in manner analogous to Bz-423 (presumably as a result of binding to a common molecular target), the ability of FK506 was examined, micromolar amounts of which effectively inhibit ubiquinol cytochrome c reductase, to protect against cell death. Inhibition by FK506 (≈ 60%) was only observed for 3-6, 12, 13, 16, and 17, which are the compounds with hydrophobic C3 side chains larger than benzene. Cell death induced by each of these compounds (including Bz-423) was also inhibited (to ≈ 60%) by pre-treating cells with either 18, 19, or 20 (at >40 μM). Compounds 18, 19, and 20 had no effect on blocking the cytotoxic activity (inhibition of ≈ 20%) of the other benzodiazepines listed in Table 2. The present invention is not limited to a particular mechanism, and an understanding of the mechanism is not necessary to practice the present invention, nonetheless, it is contemplated that these data strongly suggest that Bz-423 along with 3-6, 12, 13, 16, and 17 bind the same site within the target protein and induce apoptosis through a common mechanism. The other compounds do not bind at this site and induce a death response through a different pathway.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for inhibiting proliferation of cells comprising: exposing proliferating target cells having mitochondria to a benzodiazepine compound of Formula I to inhibit proliferation of said cells, wherein Formula I is represented by:

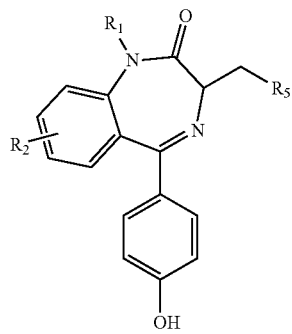

(I)

or a pharmaceutically acceptable salt, R enantiomer, S enantiomer, or a racemic mixture thereof; wherein:

$R_1$ is alkyl;
$R_2$ is halogen;
$R_5$ is one of the following:

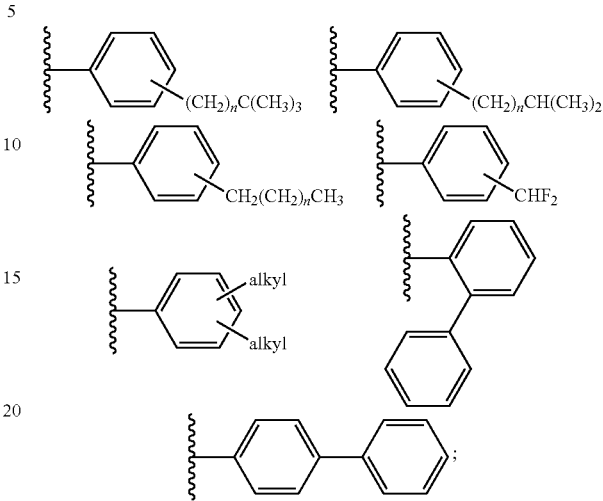

and
n is 0-5.

2. The method of claim 1, wherein said benzodiazepine compound binds to oligomycin sensitivity conferring protein.

3. The method of claim 1, wherein said target cells are in vitro cells.

4. The method of claim 1, wherein said target cells are in vivo cells.

5. The method of claim 1, wherein said target cells are ex vivo cells.

6. The method of claim 1, wherein said target cells are cancer cells.

7. The method of claim 1, wherein said target cells are selected from the group consisting of B cells, T cells, and granulocytes.

8. The method of claim 1, wherein $R_5$ is

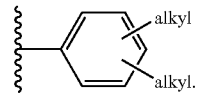

9. The method of claim 7, wherein $R_5$ is

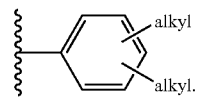

* * * * *

UNITED STATES PATENT AND TRADEMARK OFFICE
CERTIFICATE OF CORRECTION

PATENT NO. : 8,415,343 B2  
APPLICATION NO. : 11/643614  
DATED : April 9, 2013  
INVENTOR(S) : Glick et al.

Page 1 of 1

It is certified that error appears in the above-identified patent and that said Letters Patent is hereby corrected as shown below:

In the Specification:

Col. 6, line 56    After "Specifically," please delete "far" and insert --for-- therefor.

In the Claims:

Col. 10, line 41, Claim 12    After "being" please delete "connect" and insert --connected-- therefor.

Signed and Sealed this  
Thirtieth Day of July, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,415,343 B2
APPLICATION NO. : 11/643614
DATED : April 9, 2013
INVENTOR(S) : Gary D. Glick et al.

It is certified that error appears in the above-identified patent and that said Letters Patent is hereby corrected as shown below:

This certificate supersedes the Certificate of Correction issued July 30, 2013. The certificate is vacated since no Certificate of Correction was granted for this patent number. The errors appearing on the Certificate of Correction does not correspond to text in the printed patent. The patent number was erroneously mentioned and the Certificate of Correction should not have been issued.

Signed and Sealed this
Twenty-fourth Day of December, 2013

Margaret A. Focarino
*Commissioner for Patents of the United States Patent and Trademark Office*